United States Patent
Wu et al.

(10) Patent No.: US 11,098,046 B2
(45) Date of Patent: Aug. 24, 2021

(54) MACROCYCLIC COMPOUNDS AS TRK KINASE INHIBITORS AND USES THEREOF

(71) Applicant: ANGEX PHARMACEUTICAL, INC., North Brunswick, NJ (US)

(72) Inventors: Wen-Lian Wu, Green Brook, NJ (US); Zhiqiang Yang, Westfield, NJ (US); Francis Lee, Yardley, PA (US); John Qiang Tan, North Brunswick, NJ (US)

(73) Assignee: ANGEX PHARMACEUTICAL, INC., North Brunswick, NJ (US)

( * ) Notice: Subject to any disclaimer, the term of this patent is extended or adjusted under 35 U.S.C. 154(b) by 0 days.

(21) Appl. No.: 16/760,790

(22) PCT Filed: Oct. 11, 2018

(86) PCT No.: PCT/US2018/055358
§ 371 (c)(1),
(2) Date: Apr. 30, 2020

(87) PCT Pub. No.: WO2019/094143
PCT Pub. Date: May 16, 2019

(65) Prior Publication Data
US 2020/0385386 A1 Dec. 10, 2020

Related U.S. Application Data

(60) Provisional application No. 62/677,391, filed on May 29, 2018, provisional application No. 62/584,466, filed on Nov. 10, 2017.

(51) Int. Cl.
| | | |
|---|---|---|
| C07D 213/02 | (2006.01) |
| C07D 213/04 | (2006.01) |
| C07D 231/00 | (2006.01) |
| A61K 31/495 | (2006.01) |
| A61K 31/505 | (2006.01) |
| A61K 31/519 | (2006.01) |
| C07D 471/22 | (2006.01) |
| C07D 487/22 | (2006.01) |
| C07D 498/22 | (2006.01) |

(52) U.S. Cl.
CPC ......... *C07D 471/22* (2013.01); *C07D 487/22* (2013.01); *C07D 498/22* (2013.01)

(58) Field of Classification Search
CPC .. C07D 213/02; C07D 213/04; C07D 231/00; A61K 31/495; A61K 31/505; A61K 31/519
See application file for complete search history.

(56) References Cited

U.S. PATENT DOCUMENTS

| | | |
|---|---|---|
| 2011/0195948 A1 | 8/2011 | Haas et al. |
| 2013/0203776 A1 | 8/2013 | Andrews et al. |
| 2020/0291042 A1 | 9/2020 | Dai et al. |

FOREIGN PATENT DOCUMENTS

| | | |
|---|---|---|
| WO | 2011146336 A1 | 11/2011 |
| WO | 2012034095 A1 | 3/2012 |
| WO | 2015112806 A2 | 7/2015 |
| WO | 2017004342 A1 | 1/2017 |
| WO | 2017015367 A1 | 1/2017 |
| WO | 2017075107 A1 | 5/2017 |
| WO | 2017075107 A9 | 5/2017 |
| WO | 2018170381 A1 | 9/2018 |
| WO | 2019184955 A1 | 10/2019 |

OTHER PUBLICATIONS

International Search Report and Written Opinion of the International Searching Authority dated Jan. 24, 2019, corresponding to international patent application No. PCT/US2018/055358.
International Preliminary Report on Patentability from the International Bureau dated May 22, 2020, corresponding to international patent application No. PCT/US2018/055358.

*Primary Examiner* — Bruck Kifle
(74) *Attorney, Agent, or Firm* — Maschoff Brennan; Brent A. Johnson; Yuefen Zhou

(57) ABSTRACT

The present disclosure describes novel TRK kinase inhibitors and methods for preparing them. The pharmaceutical compositions comprising such TRK kinase inhibitors and methods of using them for treating cancer, infectious diseases, and other disorders are also described.

21 Claims, No Drawings

MACROCYCLIC COMPOUNDS AS TRK KINASE INHIBITORS AND USES THEREOF

CROSS-REFERENCE TO RELATED APPLICATIONS

This application is a national phase of the International Patent Application No. PCT/US2018/055358, filed Oct. 11, 2018; which claims the benefit of U.S. Provisional Application Nos. 62/584,466, filed Nov. 10, 2017, and 62/677,391, filed May 29, 2018; all of which are incorporated by reference by their entirety.

FIELD

The present disclosure relates to macrocyclic compounds, such as (R, $1^3E,1^4E$)-$3^5$-fluoro-6-methyl-7-aza-1(5,3)-pyrazolo[1,5-a]pyrimidine-3(3,2)-pyridina-2(1,2)-pyrazalidina-cyclo-octaphan-8-one (compound 1-8) analogs as TRK kinase inhibitors, and pharmaceutical compositions containing such compounds. The present disclosure also relates to the use of the compounds and compositions to treat cancer, chronic pain, infectious diseases, neurodegenerative diseases, and certain infectious disorders.

BACKGROUND

TRK family of neurotrophin receptors, TRKA, TRKB, and TRKC (encoded by NTRK1, NTRK2, and NTRK3 genes, respectively) and their neurotrophin ligands regulate growth, differentiation and survival of neurons. Translocations involving the NTRK kinase domain, mutations involving the TRK ligand-binding site, amplifications of NTRK, TRK splice variants, and autocrine/paracrine signaling are described in a diverse number of tumor types and may contribute to tumorigenesis. In particular, genomic rearrangement is the most common mechanism of oncogenic activation for this family of receptors, resulting in sustained cancer cell proliferation through activation of MAPK and AKT downstream pathways. Rearrangements of the NTRK1, NTRK2, and NTRK3 genes occur across different tumors, including lung and colorectal cancers, among others. In pediatric malignancies, NTRK gene fusions either occur at high frequency in very rare tumors, or occur at low frequency in more common tumors. Pharmacologic inhibition of oncogenic TRKA, TRKB or TRKC kinases have demonstrated relevant clinical antitumor activity.

In addition, the TRK pathway have been shown to be associated with pain, inflammatory diseases, neurodegenerative diseases, infectious diseases, and bone disorders.

Accordingly, the identification and development of small molecules that inhibit the activity of TRK kinase family will serve as an effective therapeutic approach for the treatment of a variety of TRK kinase related diseases or disorders, such as cancers.

SUMMARY

This disclosure relates to certain optionally substituted macrocyclic compounds comprising at least two rings within the macrocyclic ring system, such as certain optionally substituted ($1^3E,1^4E$)-7-aza-1(5,3)-pyrazolo[1,5-a]pyrimidina-3(3,2)-pyridina-2(1,2)-pyrazolidinacyclooctaphan-8-one. For example, some embodiments include a compound, or a pharmaceutically acceptable salt thereof, wherein the compound is: optionally substituted ($1^3E,1^4E$)-$3^5$-fluoro-6-methyl-7-aza-1(5,3)-pyrazolo[1,5-a]pyrimidina-3(3,2)-pyridina-2(1,2)-pyrazolidinacyclooctaphan-8-one, optionally substituted (R,$1^3E,1^4E$)-$3^5$-fluoro-6-methyl-7-aza-1(5,3)-pyrazolo[1,5-a]pyrimidina-3(3,2)-pyridina-2(1,2)-pyrazolidinacyclooctaphan-8-one, or optionally substituted (S,$1^3E,1^4E$)-$3^5$-fluoro-6-methyl-7-aza-1(5,3)-pyrazolo[1,5-a]pyrimidina-3(3,2)-pyridina-2(1,2)-pyrazolidinacyclooctaphan-8-one.

Some embodiments include a compound represented by Formula 1:

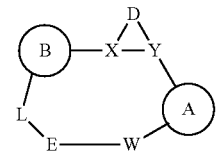

(Formula 1)

or a pharmaceutically acceptable salt thereof; wherein Ⓐ (Ring A) is optionally substituted 6-membered aromatic all carbon ring, or an optionally substituted 5-membered heteroaryl ring having 1, 2, or 3 heteroatoms independently selected from N, O and S, or optionally substituted 6-membered heteroaryl ring having 1 or 2 ring nitrogen atoms; Ⓑ (Ring B) is an optionally substituted fused bicyclic heteroaromatic ring system having 1, 2, 3, or 4 ring nitrogen atoms; X and Y are independently N or $CR^{A1}$, and X, Y, and D together form a ring system of

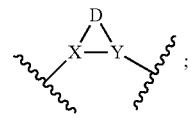

D is $C_{2-3}$ alkylene having, as chemically appropriate, 0, 1, 2, 3, 4, 5, or 6 substituents, wherein the substituents of D are independently F, C, Br, I, OH, =O, $C_{1-6}$ alkyl or $C_{1-6}$ cycloalkyl, wherein one or two of the substituents of D together with the parent ring of

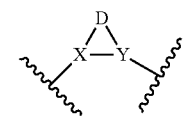

may form a fused ring system or a spiro ring system, wherein the fused ring system or the spiro ring system can be optionally substituted; L is —C(O)$NR^A$— or —$NR^A$(CO)—; E is $C_{1-3}$ alkylene having, as chemically appropriate, 0, 1, 2, 3, 4, 5, or 6 substituents, wherein the substituents of E are independently F, Cl, Br, I, OH, =O, $C_{1-6}$ alkyl or $C_{1-6}$ cycloalkyl, wherein two of the substituents of E may connect to form a ring; W is a covalent bond, O, $NR^A$, $CR^{A1}R^{B1}$, $CR^{A1}$=$CR^{B1}$, or C=$CR^{A1}R^{B1}$; $R^{A1}$ and $R^{B1}$ are independently H, F, Cl, Br, I, or $C_{1-6}$ hydrocarbyl; and $R^A$ is H or $C_{1-6}$ hydrocarbyl.

Some embodiments include a method of treating cancer and other TRK kinase related diseases or disorders comprising administering a compound described herein, or a pharmaceutically acceptable salt thereof, to a patient in need thereof.

Some embodiments include use of a compound described herein, or a pharmaceutically acceptable salt thereof, in the manufacture of a medicament for the treatment of cancer and other TRK kinase related diseases or disorders.

Some embodiments include a pharmaceutical composition comprising a therapeutically effective amount of a compound described herein, or a pharmaceutically acceptable salt thereof, in combination with at least one pharmaceutically acceptable carrier.

Some embodiments include a method of treating cancer and other TRK kinase related diseases or disorders comprising administering a pharmaceutical composition comprising a therapeutically effective amount of a compound described herein, or a pharmaceutically acceptable salt thereof, in combination with at least one pharmaceutically acceptable carrier, to a patient in need thereof.

Some embodiments include a process for making a pharmaceutical composition comprising combining a compound described herein, or a pharmaceutically acceptable salt thereof, and at least one pharmaceutically acceptable carrier.

DETAILED DESCRIPTION

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, a name or structural depiction described herein includes any stereoisomer or any mixture of stereoisomers.

In some embodiments, a compound of Formula 1 is an R-enantiomer. In some embodiments, a compound of Formula 1 is an S-enantiomer.

A hydrogen atom in any position of a compound of Formula 1 may be replaced by a deuterium. In some embodiments, a compound of Formula 1 contains a deuterium atom. In some embodiment, a compound of Formula 1 contains multiple deuterium atoms. In some embodiments, a composition comprises a compound of Formula 1 containing deuterium at greater than natural abundance, e.g. at least 10% or at least 50% greater than natural abundance.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" is broad, and includes a moiety that occupies a position normally occupied by one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, P, Si, F, C, Br, or I; provided that the substituent includes one C, N, O, S, P, Si, F, Cl, Br, or I atom, wherein N or S can be oxidized. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, phosphonic acid, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or substituted with a substituent that may independently be in any position normally occupied by a hydrogen atom when the structure is unsubstituted. Unless a point of attachment is indicated by –|, attachment may occur at any position normally occupied by a hydrogen atom.

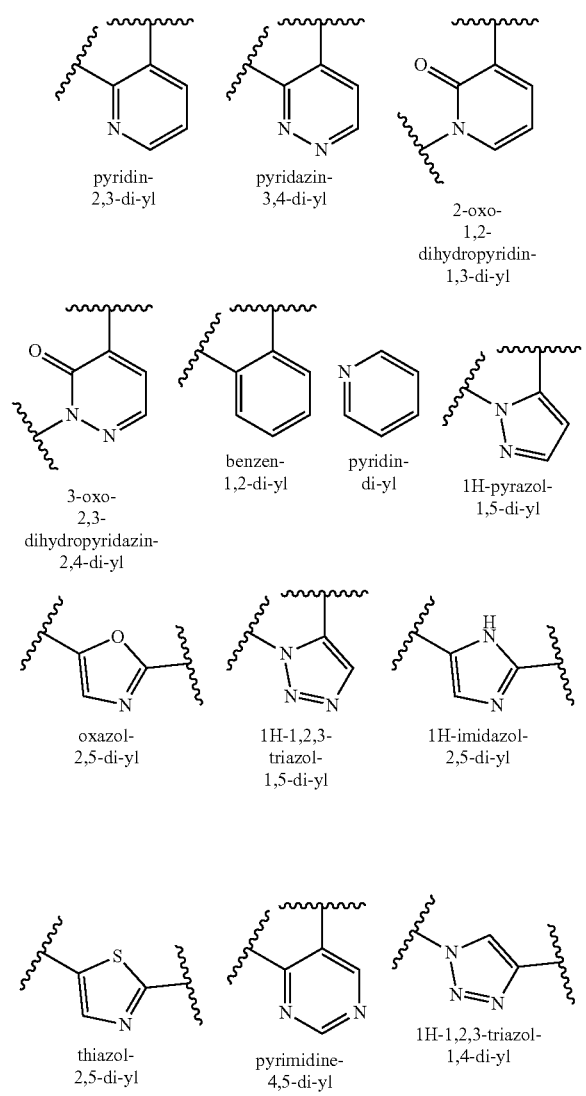

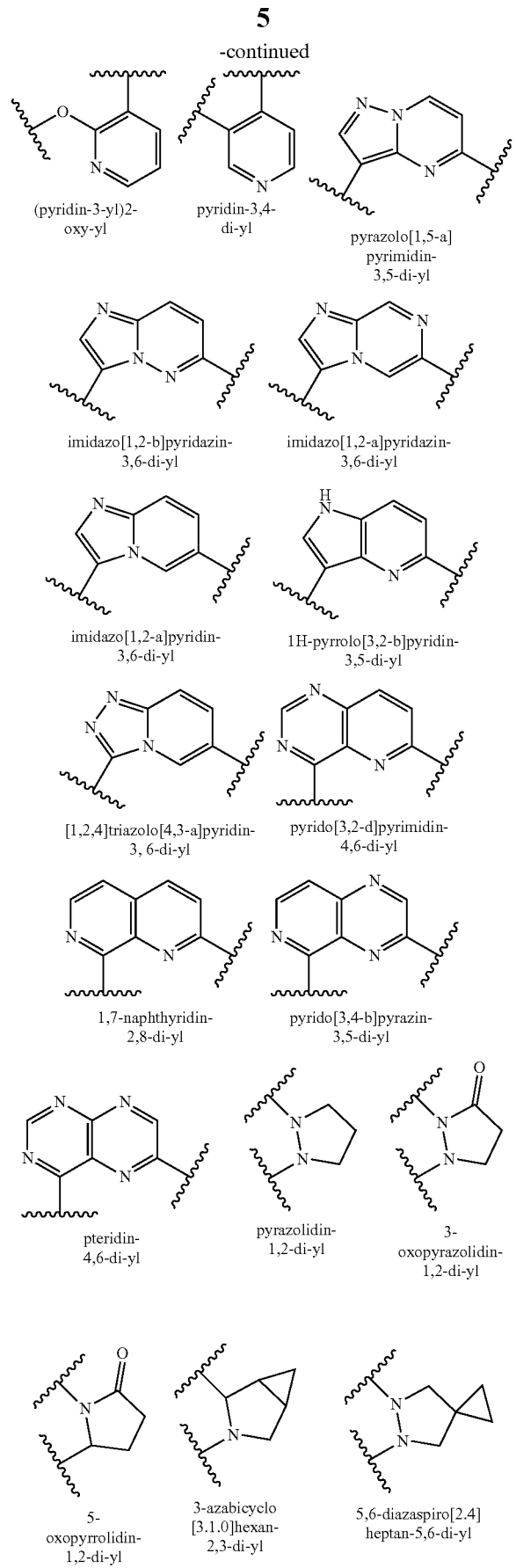
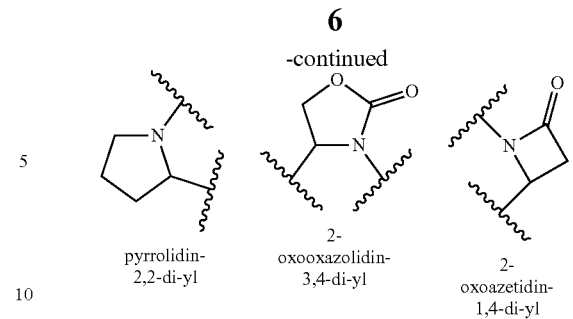

With respect to any relevant structural representation, such as Formula 1, Ring A is optionally substituted 6-membered aromatic all carbon ring; or an optionally substituted 5-membered heteroaryl ring having 1, 2, or 3 heteroatoms independently selected from N, O and S, or optionally substituted 6-membered heteroaryl ring having 1 or 2 ring nitrogen atoms. In some embodiments, any or each of the substituents of Ring A may have a molecular weight of 15 g/mol to 50 g/mol, 100 g/mol, or 300 g/mol. Potential substituents of Ring A may include halo, such as F, C, Br, I; hydrocarbyl, such as methyl, $C_2$ alkyl, $C_2$ alkenyl, $C_2$ alkynyl, $C_3$ alkyl, $C_3$ cycloalkyl, $C_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, $C_6$ alkyl, $C_6$ cycloalkyl, $C_6$ alkenyl, $C_6$ alkynyl, phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$; $C_4N_{0-1}O_{0-3}F_{0-9}H_{0-10}$; $C_5N_{0-1}O_{0-3}F_{0-11}H_{0-12}$; $C_6N_{0-1}O_{0-3}F_{0-13}H_{0-14}$; etc. In some embodiments, Ring A is optionally substituted pyridin-di-yl having 0, 1, 2, or 3 substituents, such as pyridin-2,3-di-yl substituted with F, Cl, Br, $C_{1-6}$ alkyl, —$CO_2H$, —CN, —CO—$C_{1-6}$-alkyl, —C(O)O—$C_{1-6}$-alkyl, —$C_{1-6}$ alkyl-OH, OH, $NH_2$, etc. In some embodiments, Ring A is optionally substituted pyridin-di-yl. In some embodiments, Ring A is optionally substituted pyridin-2,6-di-yl. In some embodiments, Ring A is optionally substituted pyridin-2,3-di-yl. In some embodiments, Ring A is unsubstituted pyridin-2,3-di-yl. In some embodiments, Ring A is pyridin-2,3-di-yl having 2 substituents. In some embodiments, Ring A is pyridin-2,3-di-yl having 1 substituent. In some embodiments, Ring A is 5-fluoro-pyridine-2,3-di-yl. In some embodiments, Ring A is optionally substituted 2-oxo-1,2-dihydropyridin-1,3-di-yl. In some embodiments, W-A is optionally substituted (pyridin-3-yl)2-oxy-yl.

With respect to Formula 1, in some embodiments, Ring A is represented by Formula A1, A2, A3, A4, A5, A6, A7, A8, A9, A10, A11, A12, or A14:

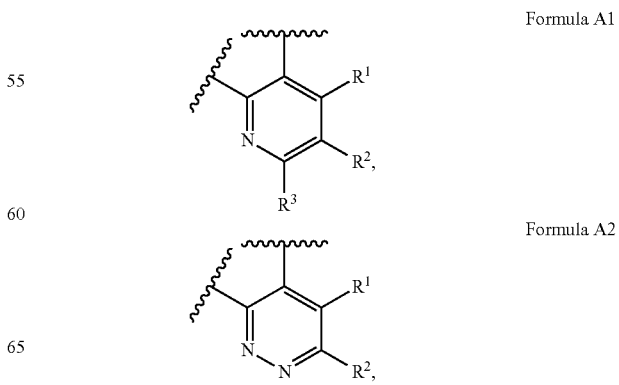

Formula A1

Formula A2

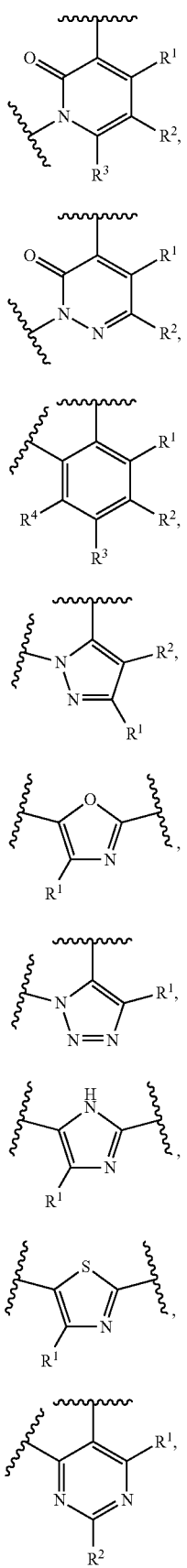

Formula A3

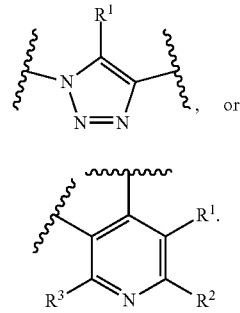, or

Formula A4

Formula A14

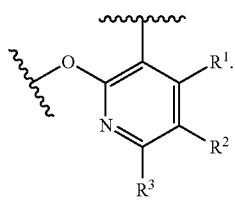

Formula A5

In some embodiments, Ring A is represented by Formula A1. In some embodiments, Ring A is represented by Formula A3.

With respect to Formula 1, in some embodiments,

Formula A6

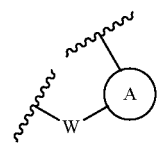

is represented by Formula A13:

Formula A7

Formula A13

[structure as shown]

Formula A8

With respect to any relevant structural representation, such as Formula A1, A2, A3, A4 A5, A6, A7, A8, A9, A10, A11, A12, A13, or A14, $R^1$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. Some of the structures with attachment points are shown below. In some embodiments, $R^1$ may be H; F; Cl; CN; $CF_3$; OH; $NH_2$; $C_{1-6}$ alkyl, such as methyl, ethyl, any one of the propyl isomers (e.g. n-propyl and isopropyl), cyclopropyl, any one of the butyl isomers, any one of the cyclobutyl isomers (e.g. cyclobutyl and methylcyclopropyl), any one of the pentyl isomers, any one of the cyclopentyl isomers, any one of the hexyl isomers, and any one of the cyclohexyl isomers, etc.; or $C_{1-6}$ alkoxy, such as —O-methyl, —O-ethyl, any one of the isomers of —O-propyl, —O-cyclopropyl, any one of the isomers of —O-butyl, any one of the isomers of —O-cyclobutyl, any one of the isomers of —O-pentyl, any one of the isomers of —O-cyclopentyl, any one of the isomers of —O-hexyl, any one of the isomers of —O-cyclohexyl, etc. In some embodiments, $R^1$ may be H, F, or Cl. In some embodiments, $R^1$ may be H. In some embodiments, $R^1$ is F.

Formula A9

Formula A10

Formula A11

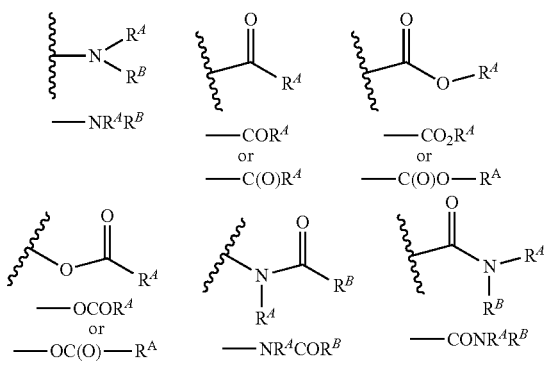

With respect to any relevant structural representation, each $R^A$ may independently be H, or $C_{1-12}$ hydrocarbyl, such as $C_{1-12}$ alkyl, $C_{1-12}$ alkenyl, $C_{1-12}$ alkynyl, phenyl, etc., including: linear or branched alkyl having a formula $C_aH_{2a+1}$, or cycloalkyl having a formula $C_aH_{2a-1}$, wherein a is 1, 2, 3, 4, 5, 6, 7, 8, 9, 10, 11, or 12, such as linear or branched alkyl with a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl with a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

With respect to any relevant structural representation, each $R^B$ may independently be H, or $C_{1-12}$ hydrocarbyl, such as $C_{1-12}$ alkyl, $C_{1-12}$ alkenyl, $C_{1-12}$ alkynyl, phenyl, etc., including: linear or branched alkyl having a formula $C_aH_{2a+1}$, or cycloalkyl having a formula $C_aH_{2a-1}$, wherein a is 1, 2, 3, 4, 5, 6, 7, 8, 9, 10, 11, or 12, such as linear or branched alkyl with a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl with a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to any relevant structural representation, such as Formula A1, A2, A3, A4 A5, A6, A13, or A14, $R^2$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^A$-$COR^B$, or —$CONR^AR^B$, etc. In some embodiments, $R^2$ may be H, F, Cl, CN, $CF_3$, OH, $NH_2$, $C_{1-6}$ alkyl, or $C_{1-6}$ alkoxy. In some embodiments, $R^2$ may be H, F, or Cl. In some embodiments, $R^2$ may be H. In some embodiments, $R^2$ is F.

With respect to any relevant structural representation, such as Formula A1, A3, A5, A13, or A14, $R^3$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^3$ may be H, F, Cl, CN, $CF_3$, OH, $NH_2$, $C_{1-6}$ alkyl, or $C_{1-6}$ alkoxy. In some embodiments, $R^3$ may be H, F, or Cl. In some embodiments, $R^3$ may be Cl. In some embodiments, $R^3$ is F.

With respect to any relevant structural representation, such as Formula A5, $R^4$ is H or any substituent, such as $R^A$, F, Cl, CN, —$OR^A$, $CF_3$, —$NO_2$, —$NR^AR^B$, —$COR^A$, $CO_2R^A$, —$OCOR^A$, $NR^ACOR^B$, or $CONR^AR^B$, etc. In some embodiments, $R^4$ may be H, F, Cl, CN, $CF_3$, OH, $NH_2$, $C_{1-6}$ alkyl, or $C_{1-6}$ alkoxy. In some embodiments, $R^4$ may be H. In some embodiments, $R^4$ is F.

With respect to any relevant structural representation, such as Formula A1, in some embodiments, $R^2$ is F. In some embodiments, $R^1$ and $R^3$ are both H. In some embodiments, $R^1$ is H, $R^3$ is H, and $R^2$ is F.

With respect to any relevant structural representation, such as Formula 1, Ring B is an optionally substituted fused bicyclic heteroaromatic ring system having 1, 2, 3, or 4 ring nitrogen atoms. In some embodiments, any or each of the substituents of Ring B may have a molecular weight of 15 g/mol to 50 g/mol, 100 g/mol, or 300 g/mol. Potential substituents of Ring B may include halo, such as F, Cl, Br, or I; hydrocarbyl, such as methyl, $C_2$ alkyl, $C_2$ alkenyl, $C_2$ alkynyl, $C_3$ alkyl, $C_3$ cycloalkyl, $C_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, $C_6$ alkyl, $C_6$ cycloalkyl, $C_6$ alkenyl, $C_6$ alkynyl, or phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$; $C_4N_{0-1}O_{0-3}F_{0-9}H_{0-10}$; $C_5N_{0-1}O_{0-3}F_{0-11}H_{0-12}$; or $C_6N_{0-1}O_{0-3}F_{0-13}H_{0-14}$; etc. In some embodiments, Ring B is optionally substituted pyrazolo[1,5-a]pyrimidin-3,5-di-yl having 0, 1, 2, or 3 substituents, such as pyrazolo[1,5-a]pyrimidin-3,5-di-yl substituted with F, Cl, Br, $C_{1-6}$ alkyl, —$CO_2H$, —CN, —CO—$C_{1-6}$-alkyl, —C(O)O—$C_{1-6}$-alkyl, —$C_{1-6}$ alkyl-OH, OH, $NH_2$, etc. In some embodiments, Ring B is pyrazolo[1,5-a]pyrimidin-3,5-di-yl having 2 substituents. In some embodiments, Ring B is pyrazolo[1,5-a]pyrimidin-3,5-di-yl having 1 substituent. In some embodiments, Ring B is unsubstituted pyrazolo[1,5-a]pyrimidin-3,5-di-yl. In some embodiments, Ring B is unsubstituted pyrazolo[1,5-a]pyrimidin-3,5-di-yl, and the pyrazole ring of the Ring B is attached to L. In some embodiments, Ring B is imidazo[1,2-b]pyridazin-3,6-di-yl having 2 substituents. In some embodiments, Ring B is imidazo[1,2-b]pyridazin-3,6-di-yl having 1 substituent. In some embodiments, Ring B is unsubstituted imidazo[1,2-b]pyridazin-3,6-di-yl. In some embodiments, Ring B is unsubstituted imidazo[1,2-b]pyridazin-3,6-di-yl, and the imidazole ring of the Ring B is attached to L.

In some embodiments, Ring B is represented by formula B1, B2, B3, B4, B5, B6, B7, B8, B9, or B10:

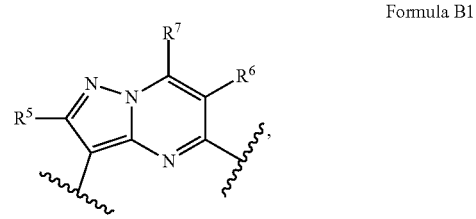

Formula B1

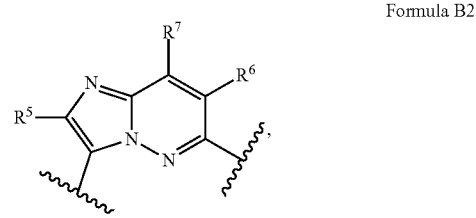

Formula B2

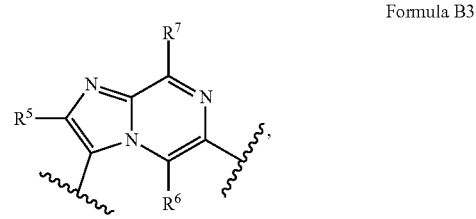

Formula B3

-continued

Formula B4
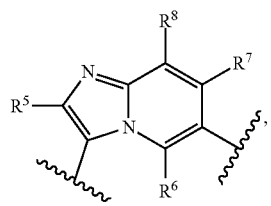

Formula B5
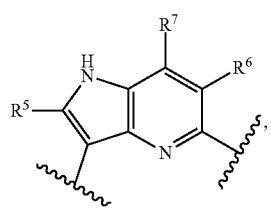

Formula B6
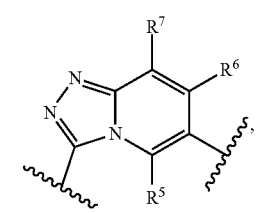

Formula B7
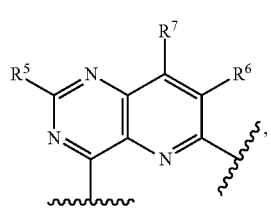

Formula B8
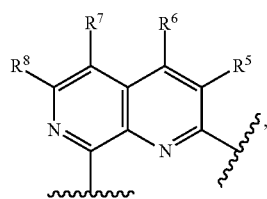

Formula B9
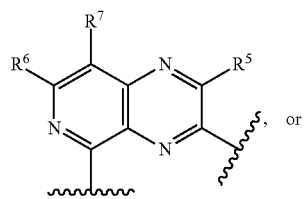

or

Formula B10
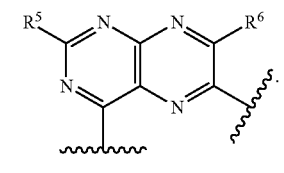

In some embodiments, B is represented by Formula B1. In some embodiments, B is represented by Formula B2.

With respect to any relevant structural representation, such as Formula B1, B2, B3, B4, B5, B6, B7, B8, B9, or B10, $R^5$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^5$ may be H, F, Cl, CN, $CF_3$, OH, $NH_2$, $C_{1-6}$ alkyl, or $C_{1-6}$ alkoxy. In some embodiments, $R^5$ may be H, F, or Cl. In some embodiments, $R^5$ may be H. In some embodiments, $R^5$ is F.

With respect to any relevant structural representation, such as Formula B1, B2, B3, B4, B5, B6, B7, B8, B9, or B10, $R^6$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^6$ may be H, F, Cl, CN, $CF_3$, OH, $NH_2$, $C_{1-6}$ alkyl, or $C_{1-6}$ alkoxy. In some embodiments, $R^6$ may be H, F, or Cl. In some embodiments, $R^6$ may be H. In some embodiments, $R^6$ is F.

With respect to any relevant structural representation, such as Formula B1, B2, B3, B4, B5, B6, B7, B8, or B9, $R^7$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^7$ may be H, F, Cl, CN, $CF_3$, OH, $NH_2$, $C_{1-6}$ alkyl, or $C_{1-6}$ alkoxy. In some embodiments, $R^7$ may be H, F, or Cl. In some embodiments, $R^7$ may be H. In some embodiments, $R^7$ is F.

With respect to any relevant structural representation, such as Formula B4 or B10, $R^8$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^8$ may be H, F, Cl, CN, $CF_3$, OH, $NH_2$, $C_{1-6}$ alkyl, or $C_{1-6}$ alkoxy. In some embodiments, $R^8$ may be H, F, or Cl. In some embodiments, $R^8$ may be H. In some embodiments, $R^8$ is F.

With respect to any relevant structural representation, such as Formula 1, X and Y are independently N or $CR^A$, and X, Y, and D together form a ring system of

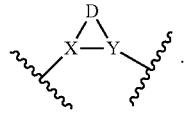

In some embodiments, X is N. In some embodiments, Y is N. In some embodiments, X is $CR^A$. In some embodiments, Y is $CR^A$. In some embodiments, X and Y are both N. In some embodiment, X is N and Y is CH.

With respect to any relevant structural representation, such as Formula 1, D is $C_{2-3}$ alkylene having, as chemically appropriate, 0, 1, 2, 3, 4, 5, or 6 substituents, wherein the substituents of D are independently F, Cl, Br, I, OH, =O, $C_{1-6}$ alkyl or $C_{1-6}$ cycloalkyl, wherein one or two of the substituents of D together with the parent ring of

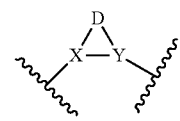

may form a fused ring system or a spiro ring system, wherein the fused ring system or the spiro ring system is optionally substituted.

In some embodiments,

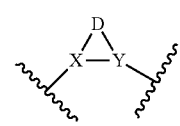

is represented by formula C1, C2, C3, C4, C5, C6, or C7:

Formula C1
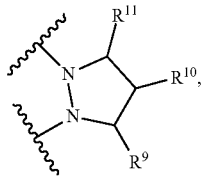

Formula C2
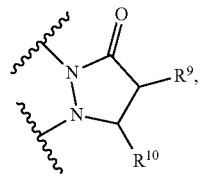

Formula C3
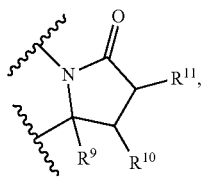

Formula C4
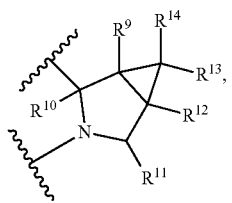

Formula C5
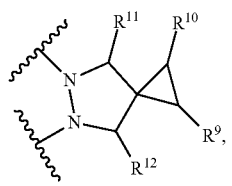

Formula C6
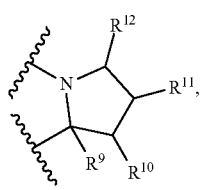

Formula C7
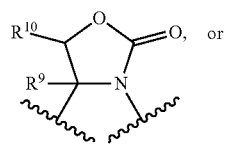

Formula C8
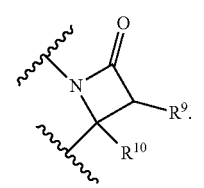

In some embodiments,

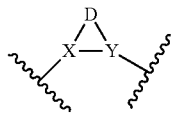

is represented by Formula C4. In some embodiments,

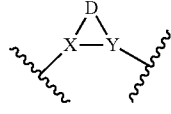

is represented by formula C1. In some embodiments,

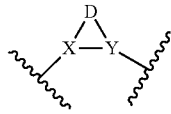

is represented by formula C5. In some embodiments,

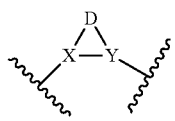

is represented by formula C6. With respect to any relevant structural representation, such as Formula C1, C2, C3, C4, C5, C6, C7, or C8, $R^9$ is H or any substituent, such as $R^A$, F, Cl, CN, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^9$ may be H, F, Cl, CN, $CF_3$, OH, $NH_2$, $C_{1-6}$ alkyl, or $C_{1-6}$ alkoxy. In some embodiments, $R^9$ may be H. In some embodiments, $R^9$ is F.

With respect to Formula C1, C2, C3, C4, C5, C6, C7, or C8, $R^{10}$ is H or any substituent, such as $R^A$, F, Cl, CN, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^{10}$ may be H, F, Cl, CN, $CF_3$, OH, $NH_2$, $C_{1-6}$ alkyl, or $C_{1-6}$ alkoxy. In some embodiments, $R^{10}$ may be H. In some embodiments, $R^{10}$ is F.

With respect to Formula C1, C3, C4, C5, or C6, $R^{11}$ is H or any substituent, such as $R^A$, F, Cl, CN, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^{11}$ may be H, F, Cl, CN, $CF_3$, OH, $NH_2$, $C_{1-6}$ alkyl, or $C_{1-6}$ alkoxy. In some embodiments, $R^{11}$ may be H. In some embodiments, $R^{11}$ is F.

With respect to Formula C4, C5, or C6, $R^{12}$ is H or any substituent, such as $R^A$, F, Cl, CN, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^{12}$ may be H, F, Cl, CN, $CF_3$, OH, $NH_2$, $C_{1-6}$ alkyl, or $C_{1-6}$ alkoxy. In some embodiments, $R^{12}$ may be H. In some embodiments, $R^{12}$ is F.

With respect to Formula C4, $R^{13}$ is H or any substituent, such as $R^A$, F, Cl, CN, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^{13}$ may be H, F, Cl, CN, $CF_3$, OH, $NH_2$, $C_{1-6}$ alkyl, or $C_{1-6}$ alkoxy. In some embodiments, $R^{13}$ may be H. In some embodiments, $R^{13}$ is F. In some embodiments, $R^{14}$ is methyl. In some embodiments, both $R^{13}$ and $R^{14}$ are methyl.

With respect to Formula C4, $R^{14}$ is H or any substituent, such as $R^A$, F, Cl, CN, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^{14}$ may be H, F, Cl, CN, $CF_3$, OH, $NH_2$, $C_{1-6}$ alkyl, or $C_{1-6}$ alkoxy. In some embodiments, $R^{14}$ may be H. In some embodiments, $R^{14}$ is F. In some embodiments, $R^{14}$ is methyl. In some embodiments, both $R^{13}$ and $R^{14}$ are methyl.

With respect to any relevant structural representation, the substituent such as $R^9$ in Formula C1 may represent a single substituent, or may represent two substituents, e.g. $R^{9'}$ and $R^{9''}$. $R^{9'}$ and $R^{9''}$ may be the same, e.g. $R^{9'}$ may be methyl and $R^{9''}$ may be a second methyl. Alternatively, $R^{9'}$ and $R^{9''}$ may be different, e.g. $R^{9'}$ may be methyl and $R^{9''}$ may be F. Similarly, $R^{10}$, or $R^{11}$ in Formula C1, $R^9$ or $R^{10}$ in formula C2, $R^{10}$ or $R^{11}$ in Formula C3, $R^{11}$ in Formula C4, $R^9$, $R^{10}$, $R^{11}$ or $R^{12}$ in Formula C5, $R^{10}$, $R^{11}$, or $R^{12}$ in Formula C6, $R^{10}$ in Formula C7, or $R^9$ in Formula C8 may represent $R^{9'}$ and $R^{9''}$, $R^{10'}$ and $R^{10''}$, $R^{11'}$ and $R^{11''}$, or $R^{12'}$ and $R^{12''}$. The substituent of $R^{9'}$, $R^{9''}$, $R^{10'}$, $R^{10''}$, $R^{11'}$, $R^{11''}$, $R^{12'}$, or $R^{12''}$ is any substituent, such as $R^A$, F, Cl, CN, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^{9'}$, $R^{9''}$, $R^{10'}$, $R^{10''}$, $R^{11'}$, $R^{11''}$, $R^{12'}$, or $R^{12''}$ may be F, Cl, CN, $CF_3$, OH, $NH_2$, $C_{1-6}$ alkyl, or $C_{1-6}$ alkoxy. In some embodiments, $R^{9'}$, $R^{9''}$, $R^{10'}$, $R^{10''}$, $R^{11'}$, $R^{11''}$, $R^{12'}$, or $R^{12''}$ is F. In some embodiments, $R^{9'}$, $R^{9''}$, $R^{10'}$, $R^{10''}$, $R^{11'}$, $R^{11''}$, $R^{12'}$, or $R^{12''}$ is methyl.

With respect to any relevant structural representation, such as Formula 1, in some embodiments, when Ring B is pyrazolo[1,5-a]pyrimidin-3,5-di-yl, L is —C(O)$NR^A$—, wherein the C atom of L is attached to Ring B, and Ring A is optionally substituted pyridin-2,3-di-yl, optionally substituted benzen-1,2-di-yl, optionally substituted 2-oxo-1,2-dihydropyridin-1,3-di-yl, or optionally substituted pyridine-2,6-di-yl,

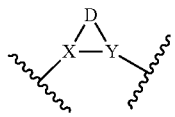

is not non-fused pyrrolidin-1,2-di-yl, or 2 oxooxazolidin-3,4-di-yl, or pyrrolidin-1,2-di-yl when X is N. In some embodiments,

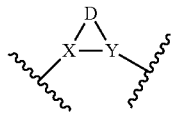

is not non-fused pyrrolidin-1,2-di-yl. In some embodiments,

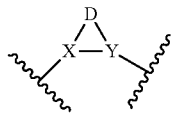

is not 2 oxooxazolidin-3,4-di-yl. In some embodiments,

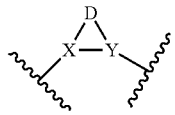

is not pyrrolidin-1,2-di-yl when X is N.

In some embodiments,

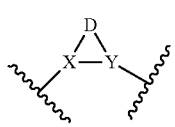

is 5,6-diazaspiro[2.4]heptan-5,6-di-yl. In some embodiments,

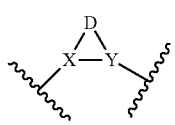

is 3-azabicyclo[3.1.0]hexan-2,3-di-yl. In some embodiments,

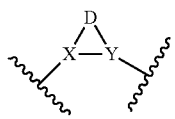

is pyrrolidin-1,2-di-yl. In some embodiments, is 6,6-dimethyl-3-azabicyclo[3.1.0]hexan-2,3-di-yl.

With respect to any relevant structural representation, such as Formula 1, L is —C(O)$NR^A$— or —$NR^A$(CO)—. In some embodiments, L is —$NR^A$(CO)—. In some embodiments, L is —C(O)$NR^A$—. In some embodiments, L is —C(O)$NR^A$—, wherein the C atom of L is directly attached to Ring B. In some embodiments, L is —C(O)NH—, wherein the C atom is directly attached to Ring B. In some embodiments, L is —NHC(O)—, wherein the N atom is directly attached to Ring B.

With respect to Formula 1, E is $C_{1-3}$ alkylene having, as chemically appropriate, 0, 1, 2, 3, 4, 5, or 6 substituents, wherein the substituents of E are independently F, Cl, Br, I, OH, $C_{1-6}$ alkyl or $C_{1-6}$ cycloalkyl, wherein two of the substituents of E may connect to form a ring. In some embodiments, E is optionally substituted $C_1$ alkylene, with 0, 1 or 2 substituents. In some embodiments, E is optionally substituted $C_2$ alkylene, with 0, 1, 2, 3, or 4 substituents. In some embodiments, E is optionally substituted $C_3$ alkylene, with 0, 1, 2, 3, 4, 5, or 6 substituents. In some embodiments, E is unsubstituted $C_{1-3}$ alkylene. In some embodiments, E has an optionally substituted cyclopropyl substituent. In some embodiments, E is optionally substituted cyclopropylmethylene. In some embodiments, E is cyclopropylmethylene. In some embodiments, E is optionally substituted cyclopropylethylene. In some embodiments, E is cyclopropylethylene. In some embodiments, E has two substituents. In some embodiments, E has 1 substituent. In some embodiments, E has 1 substituent, and wherein the substituent is methyl.

With respect of Formula 1, W is a covalent bond, O, $NR^A$, $CR^{A1}R^{B1}$, or $CR^{A1}=CR^{B1}$, wherein $R^{A1}$ and $R^{B1}$ are independently H, F, Cl, Br, I, or $C_{1-6}$ hydrocarbyl. In some embodiments, W is a covalent bond. In some embodiments, W is O. In some embodiments, W is $NR^A$. In some embodiments, W is $CR^{A1}R^{B1}$. In some embodiments, W is $CR^{A1}=CR^{B1}$. In some embodiments, W is —$CH_2$—. In some embodiments, W is —$CH(CH_3)$—. In some embodiments, W is C=$CH_2$. In some embodiments, E-W is:

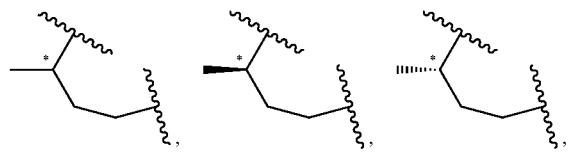

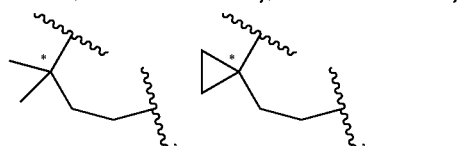

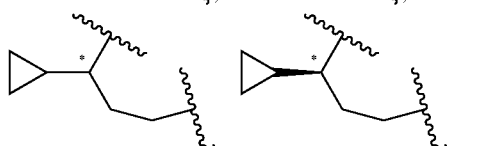

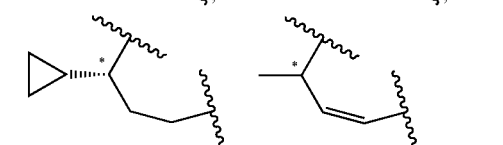

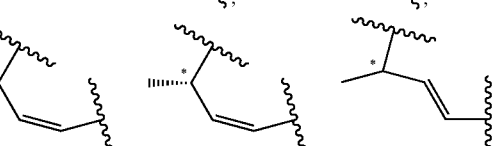

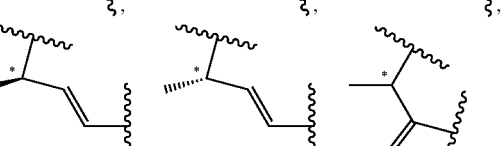

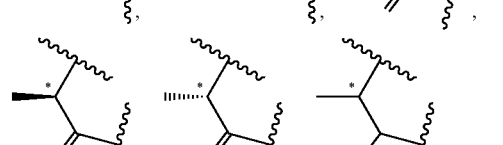

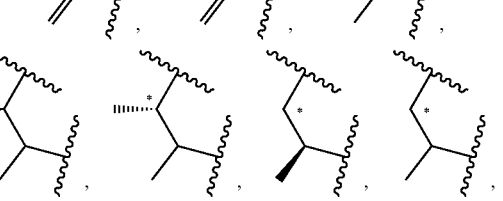

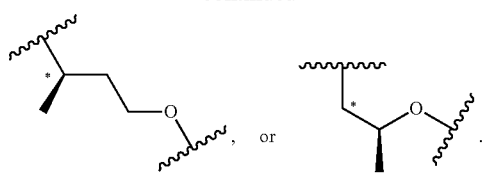

wherein the asterisk indicates the point of attachment of C atom to L. In some embodiments, E-W is:

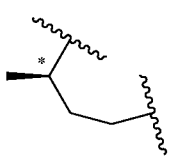

In some embodiments, E-W is:

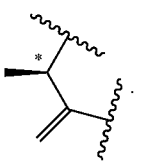 [SMILES: *C(=C)[C@H](*)C]

In some embodiments, E-W is:

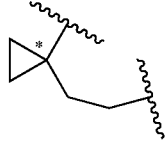

In some embodiments, E-W is:

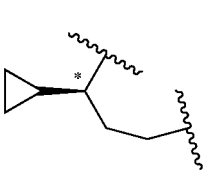

In some embodiments, E-W is:

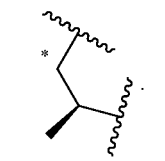

In some embodiments, E-W is:

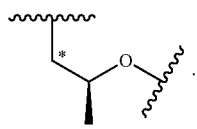 [SMILES: *C[C@H](C)O*]

Some embodiments include optionally substituted (1³E, 1⁴E)-7-aza-1(5,3)-pyrazolo[1,5-a]pyrimidina-3(3,2)-pyridina-2(1,2)-pyrazolidinacyclooctaphan-8-one, optionally substituted (2²R,E)-7-aza-1(6,3)-imidazo[1,2-b]pyridazina-3(5,4)-pyrimidina-2(1,2)-pyrrolidinacyclooctaphan-8-one, optionally substituted (1³E,1⁴E)-7-aza-1(5,3)-pyrazolo[1,5-a]pyrimidina-2(1,2)-pyrazolidina-3(1,2)-benzenacyclooctaphan-8-one, optionally substituted (2²S,E)-7-aza-1(6,3)-imidazo[1,2-b]pyridazina-3(5,4)-pyrimidina-2(1,2)-pyrrolidinacyclooctaphan-8-one, optionally substituted (1³E,1⁴E)-3¹,3²-dihydro-7-aza-1(5,3)-pyrazolo[1,5-a]pyrimidina-3(3,1)-pyridina-2(1,2)-pyrazolidinacyclooctaphane-3²,8-dione, optionally substituted (1³E,1⁴E,2²R,3⁴Z)-3¹H-7-aza-1(5,3)-pyrazolo[1,5-a]pyrimidina-3(4,1)-triazola-2(1,2)-pyrrolidinacyclooctaphan-8-one, optionally substituted (1³E,1⁴E)-4-oxa-8-aza-1(5,3)-pyrazolo[1,5-a]pyrimidina-3(3,2)-pyridina-2(1,2)-pyrazolidinacyclononaphan-9-one, optionally substituted (1³E,1⁴E,2²S,3⁴Z)-3¹H-7-aza-1(5,3)-pyrazolo[1,5-a]pyrimidina-3(4,1)-triazola-2(1,2)-pyrrolidinacyclooctaphan-8-one, optionally substituted (1³E,1⁴E)-7-aza-1(5,3)-pyrazolo[1,5-a]pyrimidina-3(3,2)-pyridina-2(1,2)-pyrazolidinacyclooctaphane-2⁵,8-dione, optionally substituted (R,1³E,1⁴E)-3¹H-7-aza-1(5,3)-pyrazolo[1,5-a]pyrimidina-3(5,1)-triazola-2(1,2)-pyrrolidinacyclooctaphan-8-one, optionally substituted (3'E,4'E)-spiro[cyclopropane-1,4'-7-aza-1(5,3)-pyrazolo[1,5-a]pyrimidina-3(3,2)-pyridina-2(1,2)-pyrazolidinacyclooctaphan]-8'-one, optionally substituted (S,1³E,1⁴E)-7-aza-1(5,3)-pyrazolo[1,5-a]pyrimidina-3(3,2)-pyridina-2(2,1)-pyrrolidinacyclooctaphan-8-one, optionally substituted (2²R,E)-7-aza-1(6,3)-imidazo[1,2-b]pyridazina-3(3,2)-pyridina-2(1,2)-pyrrolidinacyclooctaphan-8-one, optionally substituted (R,1³E,1⁴E)-7-aza-1(5,3)-pyrazolo[1,5-a]pyrimidina-3(3,2)-pyridina-2(2,1)-pyrrolidinacyclooctaphan-8-one, optionally substituted (2²S,E)-7-aza-1(6,3)-imidazo[1,2-b]pyridazina-3(3,2)-pyridina-2(1,2)-pyrrolidinacyclooctaphan-8-one, optionally substituted (1³E,1⁴E,2²R)-2³,7-diaza-1(5,3)-pyrazolo[1,5-a]pyrimidina-3(3,2)-pyridina-2(3,2)-bicyclo[3.1.0]hexanacyclooctaphan-8-one, optionally substituted (1³E,1⁴E)-8-aza-1(5,3)-pyrazolo[1,5-a]pyrimidina-3(3,2)-pyridina-2(1,2)-pyrrolidinacyclooctaphan-7-one, optionally substituted (1³E,1⁴E,2²S)-2³,7-diaza-1(5,3)-pyrazolo[1,5-a]pyrimidina-3(3,2)-pyridina-2(3,2)-bicyclo[3.1.0]hexanacyclooctaphan-8-one, optionally substituted (R,1³E,1⁴E,4E)-7-aza-1(5,3)-pyrazolo[1,5-a]pyrimidina-3(3,2)-pyridina-2(1,2)-pyrrolidinacyclooctaphan-4-en-8-one, optionally substituted (S,1³E,1⁴E,4E)-7-aza-1(5,3)-pyrazolo[1,5-a]pyrimidina-3(3,2)-pyridina-2(1,2)-pyrrolidinacyclooctaphan-4-en-8-one, optionally substituted (R,1³E,1⁴E,4Z)-7-aza-1(5,3)-pyrazolo[1,5-a]pyrimidina-3(3,2)-pyridina-2(1,2)-pyrrolidinacyclooctaphan-4-en-8-one, optionally substituted (S,1³E,1⁴E,4Z)-7-aza-1(5,3)-pyrazolo[1,5-a]pyrimidina-3(3,2)-pyridina-2(1,2)-pyrrolidinacyclooctaphan-4-en-8-one, optionally substituted (R,1³E,1⁴E)-4-methylene-6-aza-1(5,3)-pyrazolo[1,5-a]pyrimidina-3(3,2)-pyridina-2(1,2)-pyrrolidinacycloheptaphan-7-one, optionally substituted (S,1³E, 1⁴E)-4-methylene-6-aza-1(5,3)-pyrazolo[1,5-a]pyrimidina-3(3,2)-pyridina-2(1,2)-pyrrolidinacycloheptaphan-7-one, optionally substituted (R,1³E,1⁴E)-6-aza-1(5,3)-pyrazolo[1,5-a]pyrimidina-3(3,2)-pyridina-2(1,2)-pyrrolidinacycloheptaphan-7-one, optionally substituted (E)-7-aza-1(6,3)-imidazo[1,2-b]pyridazina-3(4,3)-pyridina-2(1,2)-pyrrolidinacyclooctaphan-8-one, optionally substituted (1³E,1⁴E,2¹R,2²R,2⁵S)-4-methylene-2³,6-diaza-1(5,3)-pyrazolo[1,5-a]pyrimidina-3(3,2)-pyridina-2(3,2)-bicyclo[3.1.0]hexanacycloheptaphan-7-one, optionally substituted, (1³E,1⁴E,2¹R,2⁴S,2⁵S)-4-methylene-2³,6-diaza-1(5,3)-pyrazolo[1,5-a]pyrimidina-3(3,2)-pyridina-2(3,4)-bicyclo[3.1.0]hexanacycloheptaphan-7-one, optionally substituted (1³E,1⁴E,2¹R,2²R,2⁵S)-4-oxa-2³,7-diaza-1(5,3)-pyrazolo[1,5-a]pyrimidina-3(3,2)-pyridina-2(3,2)-bicyclo[3.1.0]hexanacyclooctaphan-8-one, optionally substituted (1³E, 1⁴E,2¹R,2⁴S,2⁵S)-4-oxa-2³,7-diaza-1(5,3)-pyrazolo[1,5-a]pyrimidina-3(3,2)-pyridina-2(3,4)-bicyclo[3.1.0]hexanacyclooctaphan-8-one, optionally substituted (1³E, 1⁴E,2¹R,2²R,2⁵S)-3¹,3²-dihydro-2³,6-diaza-1(5,3)-pyrazolo[1,5-a]pyrimidina-3(3,1)-pyridina-2(3,2)-bicyclo[3.1.0]hexanacycloheptaphane-3²,7-dione, optionally substituted (1³E,1⁴E,2¹R,2⁴S,2⁵S)-3¹,3²-dihydro-2³,6-diaza-1(5,3)-pyrazolo[1,5-a]pyrimidina-3(3,1)-pyridina-2(3,4)-bicyclo[3.1.0]hexanacycloheptaphane-3²,7-dione, optionally substituted (1³E,1⁴E,2¹R,2²R,2⁵S)-2³,7-diaza-1(5,3)-pyrazolo[1,5-a]pyrimidina-3(3,2)-pyridina-2(3,2)-bicyclo[3.1.0]hexanacyclooctaphan-8-one, or optionally substituted (1³E, 1⁴E,2¹S,2⁴S,2⁵R)-2⁶,2⁶-dimethyl-2³,7-diaza-1(5,3)-pyrazolo[1,5-a]pyrimidina-3(3,2)-pyridina-2(3,4)-bicyclo[3.1.0]hexanacyclooctaphan-8-one.

Some embodiments include one of the compounds listed in Table 1 below, wherein each structure can be optionally substituted:

TABLE 1

Compound structures and their ID numbers

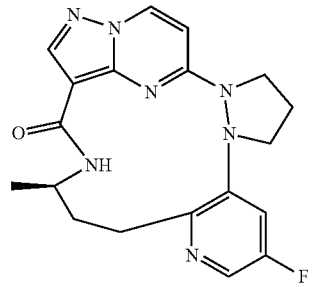 [SMILES: C[C@@H]1CCc2ncc(F)cc2N2CCCN2c2ccn3ncc(c3n2)C(=O)N1]

1-8

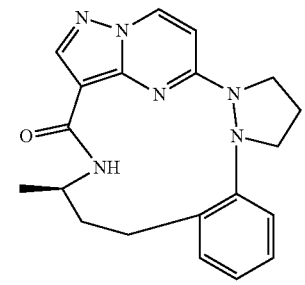 [SMILES: C[C@@H]1CCc2ccccc2N2CCCN2c2ccn3ncc(c3n2)C(=O)N1]

1-17

TABLE 1-continued
Compound structures and their ID numbers
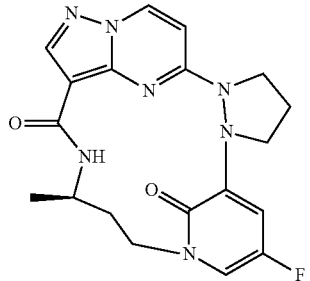 [SMILES: C[C@@H]1CCn2cc(F)cc(c2=O)N2CCCN2c2ccn3ncc(c3n2)C(=O)N1] 3-3
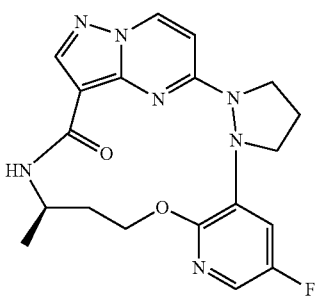 [SMILES: C[C@@H]1CCOc2ncc(F)cc2N2CCCN2c2ccn3ncc(c3n2)C(=O)N1] 4-3
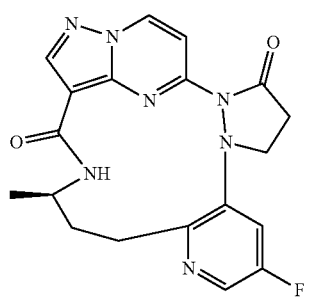 [SMILES: C[C@@H]1CCc2ncc(F)cc2N2CCC(=O)N2c2ccn3ncc(c3n2)C(=O)N1] 5-6
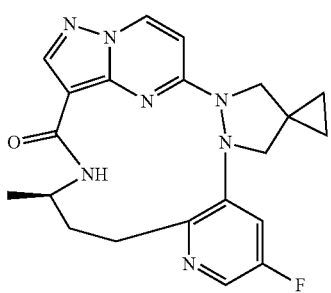 [SMILES: C[C@@H]1CCc2ncc(F)cc2N2CC3(CC3)CN2c2ccn3ncc(c3n2)C(=O)N1] 6-10
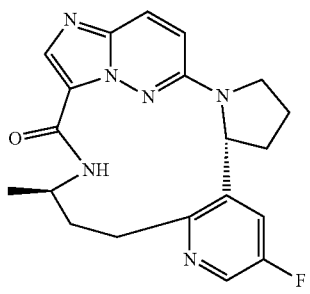 [SMILES: C[C@@H]1CCc2ncc(F)cc2[C@H]2CCCN2c2ccc3ncc(n3n2)C(=O)N1] 7-11
TABLE 1-continued
Compound structures and their ID numbers
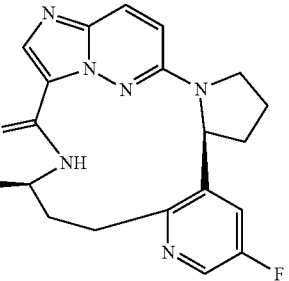 7-12
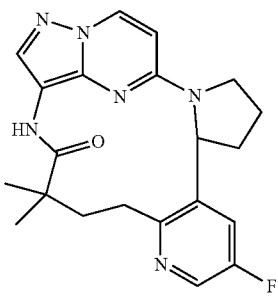 [SMILES: CC1(C)CCc2ncc(F)cc2C2CCCN2c2ccn3ncc(c3n2)NC1=O] 8-8
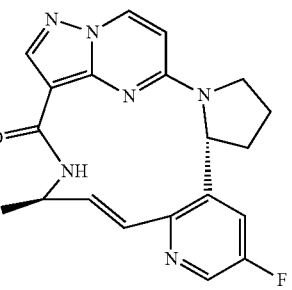 9-7
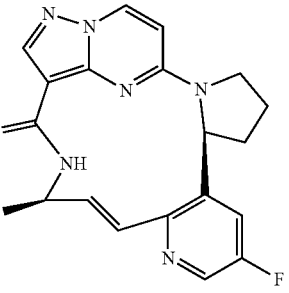 9-8
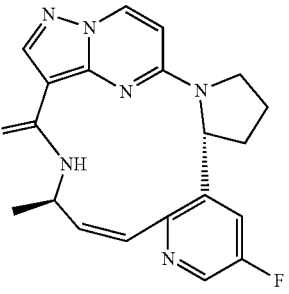 10-5

TABLE 1-continued
Compound structures and their ID numbers
10-6
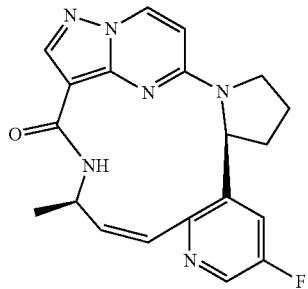 [SMILES: C[C@@H]1/C=C\c2ncc(F)cc2[C@@H]2CCCN2c2ccn3ncc(c3n2)C(=O)N1]
11-4
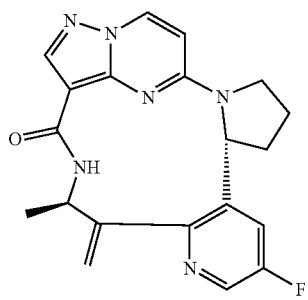 [SMILES: C=C1c2ncc(F)cc2[C@H]2CCCN2c2ccn3ncc(c3n2)C(=O)N[C@@H]1C]
11-5
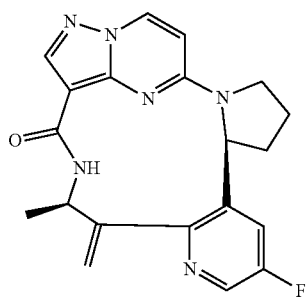 [SMILES: C=C1c2ncc(F)cc2[C@@H]2CCCN2c2ccn3ncc(c3n2)C(=O)N[C@@H]1C]
11-6
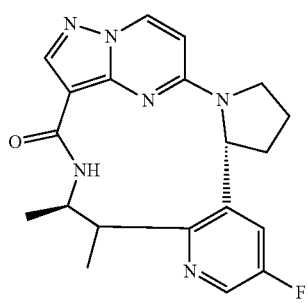 [SMILES: CC1c2ncc(F)cc2[C@H]2CCCN2c2ccn3ncc(c3n2)C(=O)N[C@@H]1C]
12-12
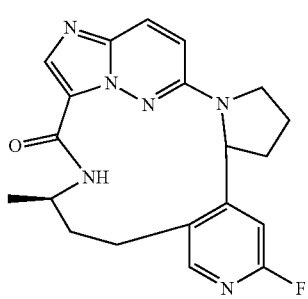 [SMILES: C[C@@H]1CCc2cnc(F)cc2C2CCCN2c2ccc3ncc(n3n2)C(=O)N1]
TABLE 1-continued
Compound structures and their ID numbers
13-11
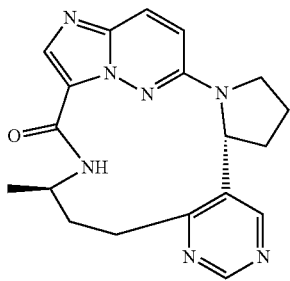 [SMILES: C[C@@H]1CCc2ncncc2[C@H]2CCCN2c2ccc3ncc(n3n2)C(=O)N1]
13-12
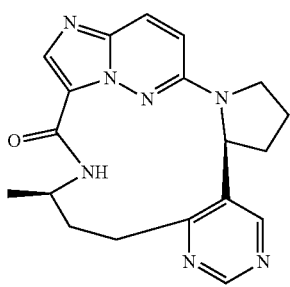 [SMILES: C[C@@H]1CCc2ncncc2[C@@H]2CCCN2c2ccc3ncc(n3n2)C(=O)N1]
14-6
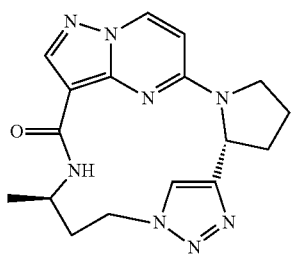 [SMILES: C[C@@H]1CCn2cc(nn2)[C@H]2CCCN2c2ccn3ncc(c3n2)C(=O)N1]
14-7
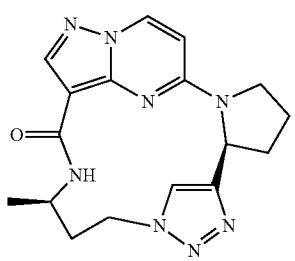 [SMILES: C[C@@H]1CCn2cc(nn2)[C@@H]2CCCN2c2ccn3ncc(c3n2)C(=O)N1]
15-10
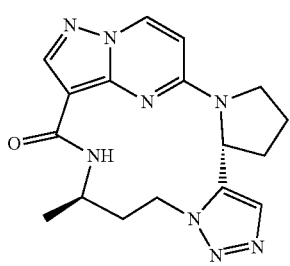 [SMILES: C[C@@H]1CCn2nncc2[C@H]2CCCN2c2ccn3ncc(c3n2)C(=O)N1]

TABLE 1-continued
Compound structures and their ID numbers
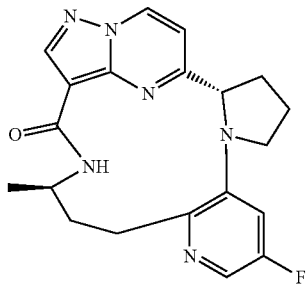 [SMILES: C[C@@H]1CCc2ncc(F)cc2N2CCC[C@H]2c2ccn3ncc(c3n2)C(=O)N1] 16-10
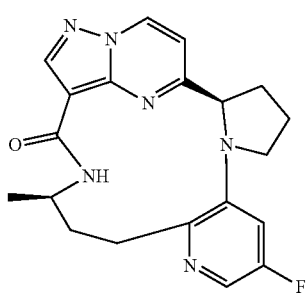 [SMILES: C[C@@H]1CCc2ncc(F)cc2N2CCC[C@@H]2c2ccn3ncc(c3n2)C(=O)N1] 16-11
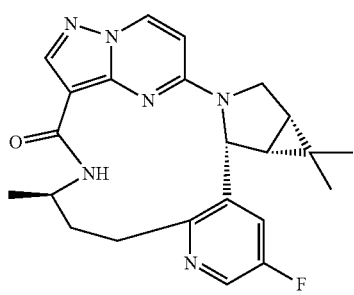 17-12
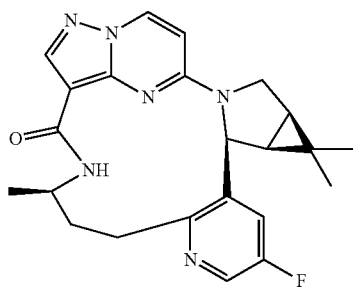 17-13
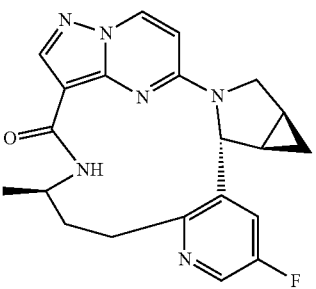 [SMILES: C[C@@H]1CCc2ncc(F)cc2[C@H]2[C@@H]3C[C@@H]3CN2c2ccn3ncc(c3n2)C(=O)N1] 18-11
TABLE 1-continued
Compound structures and their ID numbers
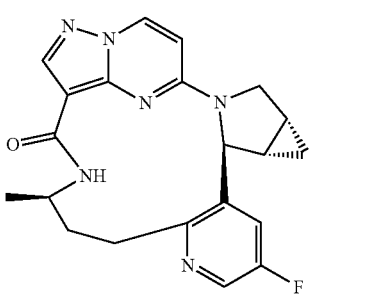 [SMILES: C[C@@H]1CCc2ncc(F)cc2[C@@H]2[C@H]3C[C@H]3CN2c2ccn3ncc(c3n2)C(=O)N1] 18-12
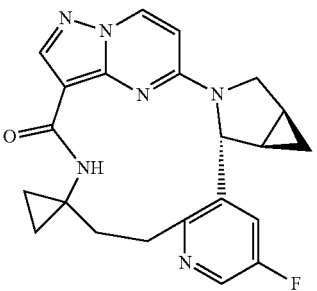 [SMILES: O=C1NC2(CCc3ncc(F)cc3[C@H]3[C@@H]4C[C@@H]4CN3c3ccn4ncc1c4n3)CC2] 19-5
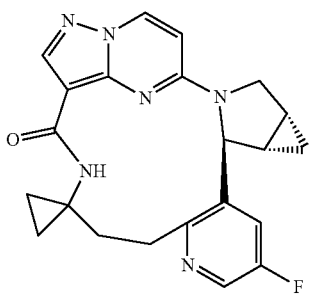 [SMILES: O=C1NC2(CCc3ncc(F)cc3[C@@H]3[C@H]4C[C@H]4CN3c3ccn4ncc1c4n3)CC2] 19-6
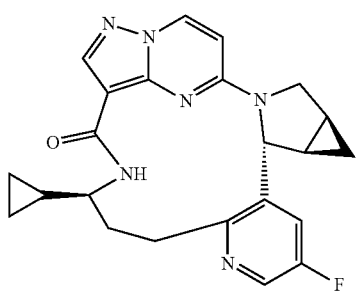 [SMILES: O=C1N[C@H](C2CC2)CCc2ncc(F)cc2[C@H]2[C@@H]3C[C@@H]3CN2c2ccn3ncc1c3n2] 20-5
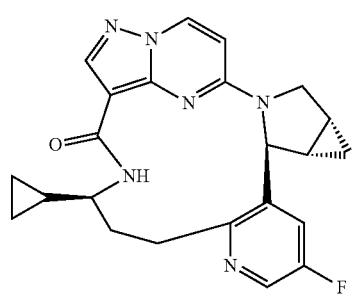 [SMILES: O=C1N[C@H](C2CC2)CCc2ncc(F)cc2[C@@H]2[C@H]3C[C@H]3CN2c2ccn3ncc1c3n2] 20-6

TABLE 1-continued

Compound structures and their ID numbers

| ID |
|---|
| 21-4 |
| 21-5 |
| 22-6 |
| 22-7 |
| 23-3 |
| 23-4 |
| 24-10 |
| 24-11 |

Some embodiments include an optionally substituted compound or core structure from Table 1. A core structure is a compound of Table 1 with the substituents of $CH_3$ and F groups removed.

A pharmaceutical composition comprising a compound described herein, such as a compound of Formula 1, for example optionally substituted ($1^3E,1^4E$)-7-aza-1(5,3)-pyrazolo[1,5-a]pyrimidina-3(3,2)-pyridina-2(1,2)-pyrazolidinacyclooctaphan-8-one, optionally substituted ($2^2R,E$)-7-aza-1(6,3)-imidazo[1,2-b]pyridazina-3(5,4)-pyrimidina-2(1,2)-pyrrolidinacyclooctaphan-8-one, optionally substituted ($1^3E,1^4E$)-7-aza-1(5,3)-pyrazolo[1,5-a]pyrimidina-2(1,2)-pyrazolidina-3(1,2)-benzenacyclooctaphan-8-one, optionally substituted ($2^2S,E$)-7-aza-1(6,3)-imidazo[1,2-b]pyridazina-3(5,4)-pyrimidina-2(1,2)-pyrrolidinacyclooctaphan-8-one, optionally substituted ($1^3E,1^4E$)-$3^1,3^2$-dihydro-7-aza-1(5,3)-pyrazolo[1,5-a]pyrimidina-3(3,1)-pyridina-2(1,2)-pyrazolidinacyclooctaphane-32,8-dione, optionally substituted ($1^3E,1^4E,2^2R,3^4Z$)-$3^1H$-7-aza-1(5,3)-pyrazolo[1,5-a]pyrimidina-3(4,1)-triazola-2(1,2)-pyrrolidinacyclooctaphan-8-one, optionally substituted ($1^3E,1^4E$)-4-oxa-8-aza-1(5,3)-pyrazolo[1,5-a]pyrimidina-3(3,2)-pyridina-2(1,2)-pyrazolidinacyclononaphan-9-one, optionally substituted ($1^3E,1^4E,2^2S,3^4Z$)-$3^1H$-7-aza-1(5,3)-pyrazolo[1,5-a]pyrimidina-3(4,1)-triazola-2(1,2)-pyrrolidinacyclooctaphan-8-one, optionally substituted ($1^3E,1^4E$)-7-aza-1(5,3)-pyrazolo[1,5-a]pyrimidina-3(3,2)- pyridina-2(1,2)-pyrazolidinacyclooctaphane-$2^5$,8-dione, optionally substituted (R,$1^3$E,$1^4$E)-$3^1$H-7-aza-1(5,3)-pyrazolo[1,5-a]pyrimidina-3(5,1)-triazola-2(1,2)-pyrrolidinacyclooctaphan-8-one, optionally substituted (3'E,4'E)-spiro [cyclopropane-1,4'-7-aza-1(5,3)-pyrazolo[1,5-a]pyrimidina-3(3,2)-pyridina-2(1,2)-pyrazolidinacyclooctaphan]-8'-one, optionally substituted (S,$1^3$E,$1^4$E)-7-aza-1(5,3)-pyrazolo[1,5-a]pyrimidina-3(3,2)-pyridina-2(2,1)-pyrrolidinacyclooctaphan-8-one, optionally substituted ($2^2$R,E)-7-aza-1(6,3)-imidazo[1,2-b]pyridazina-3(3,2)-pyridina-2(1,2)-pyrrolidinacyclooctaphan-8-one, optionally substituted (R,$1^3$E,$1^4$E)-7-aza-1(5,3)-pyrazolo[1,5-a]pyrimidina-3(3,2)-pyridina-2(2,1)-pyrrolidinacyclooctaphan-8-one, optionally substituted ($2^2$S,E)-7-aza-1(6,3)-imidazo[1,2-b]pyridazina-3(3,2)-pyridina-2(1,2)-pyrrolidinacyclooctaphan-8-one, optionally substituted ($1^3$E,$1^4$E,$2^2$R)-$2^3$,7-diaza-1(5,3)-pyrazolo[1,5-a]pyrimidina-3(3,2)-pyridina-2(3,2)-bicyclo[3.1.0]hexanacyclooctaphan-8-one, optionally substituted ($1^3$E,$1^4$E)-8-aza-1(5,3)-pyrazolo[1,5-a]pyrimidina-3(3,2)-pyridina-2(1,2)-pyrrolidinacyclooctaphan-7-one, optionally substituted ($1^3$E,$1^4$E,$2^2$S)-$2^3$,7-diaza-1(5,3)-pyrazolo[1,5-a]pyrimidina-3(3,2)-pyridina-2(3,2)-bicyclo[3.1.0]hexanacyclooctaphan-8-one, optionally substituted (R,$1^3$E,$1^4$E,4E)-7-aza-1(5,3)-pyrazolo[1,5-a]pyrimidina-3(3,2)-pyridina-2(1,2)-pyrrolidinacyclooctaphan-4-en-8-one, optionally substituted (S,$1^3$E,$1^4$E,4E)-7-aza-1(5,3)-pyrazolo[1,5-a]pyrimidina-3(3,2)-pyridina-2(1,2)-pyrrolidinacyclooctaphan-4-en-8-one, optionally substituted (R,$1^3$E,$1^4$E,4Z)-7-aza-1(5,3)-pyrazolo[1,5-a]pyrimidina-3(3,2)-pyridina-2(1,2)-pyrrolidinacyclooctaphan-4-en-8-one, optionally substituted (S,$1^3$E,$1^4$E,4Z)-7-aza-1(5,3)-pyrazolo[1,5-a]pyrimidina-3(3,2)-pyridina-2(1,2)-pyrrolidinacyclooctaphan-4-en-8-one, optionally substituted (R,$1^3$E,$1^4$E)-4-methylene-6-aza-1(5,3)-pyrazolo[1,5-a]pyrimidina-3(3,2)-pyridina-2(1,2)-pyrrolidinacycloheptaphan-7-one, optionally substituted (S,$1^3$E,$1^4$E)-4-methylene-6-aza-1(5,3)-pyrazolo[1,5-a]pyrimidina-3(3,2)-pyridina-2(1,2)-pyrrolidinacycloheptaphan-7-one, optionally substituted (R,$1^3$E,$1^4$E)-6-aza-1(5,3)-pyrazolo[1,5-a]pyrimidina-3(3,2)-pyridina-2(1,2)-pyrrolidinacycloheptaphan-7-one, optionally substituted (E)-7-aza-1(6,3)-imidazo[1,2-b]pyridazina-3(4,3)-pyridina-2(1,2)-pyrrolidinacyclooctaphan-8-one, optionally substituted ($1^3$E,$1^4$E,$2^1$R,$2^2$R,$2^5$S)-4-methylene-$2^3$,6-diaza-1(5,3)-pyrazolo[1,5-a]pyrimidina-3(3,2)-pyridina-2(3,2)-bicyclo[3.1.0]hexanacycloheptaphan-7-one, optionally substituted ($1^3$E,$1^4$E,$2^1$R,$2^4$S,$2^5$S)-4-methylene-$2^3$,6-diaza-1(5,3)-pyrazolo[1,5-a]pyrimidina-3(3,2)-pyridina-2(3,4)-bicyclo[3.1.0]hexanacycloheptaphan-7-one, optionally substituted ($1^3$E,$1^4$E,$2^1$R,$2^2$R,$2^5$S)-4-oxa-$2^3$,7-diaza-1(5,3)-pyrazolo[1,5-a]pyrimidina-3(3,2)-pyridina-2(3,2)-bicyclo[3.1.0]hexanacyclooctaphan-8-one, optionally substituted ($1^3$E,$1^4$E,$2^1$R,$2^4$S,$2^5$S)-4-oxa-$2^3$,7-diaza-1(5,3)-pyrazolo[1,5-a]pyrimidina-3(3,2)-pyridina-2(3,4)-bicyclo[3.1.0]hexanacyclooctaphan-8-one, optionally substituted ($1^3$E,$1^4$E,$2^1$R,$2^2$R,$2^5$S)-$3^1$,$3^2$-dihydro-$2^3$,6-diaza-1(5,3)-pyrazolo[1,5-a]pyrimidina-3(3,1)-pyridina-2(3,2)-bicyclo[3.1.0]hexanacycloheptaphane-$3^2$,7-dione, optionally substituted ($1^3$E,$1^4$E,$2^1$R,$2^4$S,$2^5$S)-$3^1$,$3^2$-dihydro-$2^3$,6-diaza-1(5,3)-pyrazolo[1,5-a]pyrimidina-3(3,1)-pyridina-2(3,4)-bicyclo[3.1.0]hexanacycloheptaphane-$3^2$,7-dione, optionally substituted ($1^3$E,$1^4$E,$2^1$R,$2^2$R,$2^5$S)-$2^3$,7-diaza-1(5,3)-pyrazolo[1,5-a]pyrimidina-3(3,2)-pyridina-2(3,2)-bicyclo[3.1.0]hexanacyclooctaphan-8-one, or optionally substituted ($1^3$E,$1^4$E,$2^1$S,$2^4$S,$2^5$R)-$2^6$,$2^6$-dimethyl-$2^3$,7-diaza-1(5,3)-pyrazolo[1,5-a]pyrimidina-3(3,2)-pyridina-2(3,4)-bicyclo[3.1.0]hexanacyclooctaphan-8-one, or a pharmaceutically acceptable salt thereof (Referred to herein as a "subject compound"), may be adapted for oral, or parental, such as intravenous, intramuscular, topical, intraperitoneal, nasal, buccal, sublingual, or subcutaneous administration, or for administration via respiratory tract in the form of, for example, an aerosol or an air-suspended fine powder. The dosage of a subject compound may vary depending on the route of administration, body weight, age, the type and condition of the disease being treated. A pharmaceutical composition provided herein may optionally comprise two or more subject compounds without an additional therapeutic agent, or may comprise an additional therapeutic agent (i.e., a therapeutic agent other than a compound provided herein). For example, the compounds of the disclosure can be used in combination with at least one other therapeutic agent. Therapeutic agents include, but are not limited to antibiotics, antiemetic agents, antidepressants, and antifungal agents, antiinflammatory agents, antiviral agents, and anticancer agents that are known in the art. The pharmaceutical composition may be used for the treatment of cancer, chronic pain, infectious diseases, neurodegenerative diseases, and certain infectious disorders in patients. The term "patient" herein means a mammal (e.g., a human or an animal). In some embodiments, the patient has cancer.

The pharmaceutical composition described herein can be prepared by combining a subject compound, with at least one pharmaceutical acceptable inert ingredient, such as a carrier, excipient, filler, lubricant, flavoring agent, buffer, etc., selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

Some embodiments include a method of treating a disease or disorder associated with TRK kinase, such as cancers comprising administering of a therapeutically effective amount of a subject compound or a pharmaceutical composition comprising a subject compound to a patient in need thereof. The term a "therapeutically effective amount" herein refers to an amount of a compound or a pharmaceutical composition of the present disclosure provided herein sufficient to be effective in inhibiting TRK kinase enzyme and thus providing a benefit in the treatment of cancer, infectious diseases and other TRK kinase associated disorders, to delay or minimize symptoms associated with cancer, infectious diseases and other TRK kinase associated disorders, or to ameliorate a disease or infection or cause thereof. In some embodiments, about 0.01-1000 mg of a subject compound may be a therapeutically effective amount. The term "treatment" refers to causing a therapeutically beneficial effect, such as ameliorating existing symptoms, ameliorating the underlying causes of symptoms, postponing, preventing the further development of a disorder, or reducing the severity of symptoms that are otherwise expected to develop without treatment.

Experimental Section:

Preparation of Compounds

The compounds of the disclosure can be made using procedures known in the art. The following reaction schemes show typical procedures, but those skilled in the art will recognize that other procedures can also be suitable for using to prepare these compounds. For examples in Formula I, wherein $R^A$, $R^B$, or $R^C$ is not hydrogen, those skilled in the art will recognize that changes to the requisite reagents can be made at the appropriate steps in the synthetic methods outlined below. Reactions may involve monitoring for consumption of starting materials, and there are many methods for the monitoring, including but not limited to thin layer chromatography (TLC), liquid chromatography mass spectrometry (LCMS), and Nuclear magnetic resonance spectroscopy (NMR). Those skilled in the art will recognize that any synthetic method specified in the examples shown below can be substituted by other non-limiting methods when suitable.

Some of the techniques, solvents and reagents can be referred to by their abbreviations as follows:
Acetonitrile: MeCN or ACN
Aqueous: aq.
Benzotriazol-1-yloxytris(dimethylamino)phosphonium hexafluorophosphate: BOP
Benzyl: Bn
Bis(pinacolato)diboron: $B_2(pin)_2$
Copper(II) triflate: $Cu(OTf)_2$
1-[Bis(dimethylamino)methylene]-1H-1,2,3-triazolo[4,5-b]pyridinium 3-oxid hexafluorophosphate: HATU
[1,1'-Bis(diphenylphosphino)ferrocene]-dichloropalladium (II): $Pd(dppf)Cl_2$
1,8-Diazabicyclo(5.4.0)undec-7-ene: DBU
Dichloromethane: DCM
Diethyl azodicarboxylate: DEAD
Diisopropylethylamine: DIPEA, DIEA or $iPr_2Net$
Dimethylaminopyridine: DMAP
Dimethoxyethane: DME
Dimethylformamide: DMF
Dimethylsulfoxide: DMSO
Diphenylphosphoryl azide: DPPA
Di-tert-butyl dicarbonate: $(Boc)_2O$
4,4'-Di-tert-butyl-2,2'-dipyridyl: dtbbpy
1-Ethyl-3-(3-dimethylaminopropyl)carbodiimide: EDCI
Equivalents: equiv.
Ether or diethyl ether: $Et_2O$
Ethyl acetate: AcOEt or EtOAc
Ethyl magnesium bromide: EtMgBr
Example: Ex. or ex.
Pentafluorophenyl diphenylphosphinate: FDPP
Grams: g
High performance liquid chromatography: HPLC
1-Hydroxy-7-azabenzotriazole: HOAT
1-Hydroxybenzotriazole: HOBT or HOBt
Inhibition: Inh.
Liquid chromatography mass spectrometry: LCMS
Lithium aluminum hydride: LAH
Methansulfonyl chloride: $MeSO_2Cl$
Methyl iodide: MeI
Methanol: MeOH
Microliter: μl
Micrometer: μm
Milligram: mg
Milliliter: mL
Millimole: mmol
n-Butyllithium: n-BuLi
s-Butyllithium: s-BuLi
Nuclear magnetic resonance spectroscopy: NMR
Palladium (II) acetate: $Pd(OAc)_2$
Palladium on activated carbon: Pd/C
Palladium tetra-triphenylphosphine: $Pd(PPh_3)_4$
Tris(dibenzylideneacetone) dipalladium: $Pd_2(dba)_3$
N-Phenyl bis(trifluoromethanwsulfonimide): $PhNTf_2$
p-Toluenesulfonic acid: PTSA
Preparative HPLC: Prep-HPLC
Retention time: $t_R$
Rhodium on activated carbon: Rh/C
Room temperature (ambient, ~25° C.): rt or RT
Supercritical Fluid Chromatography: SFC
Tert-butyl methyl ether: TBME
Temperature: temp.
Tetrahydrofuran: THF
Thin layer chromatography: TLC
Triethylamine: $Et_3N$
Trifluoroacetic acid: TFA
Triflic anhydride: $(Tf)_2O$
4,5-Bis(diphenylphosphino)-9,9-dimethylxanthene: Xantphos
2-Dicyclohexylphosphino-2',4',6'-triisopropylbiphenyl: X-phos
[4,4'-Bis(1,1-dimethylethyl)-2,2'-bipyridine-N1,N1']bis[3,5-difluoro-2-[5-(trifluoromethyl)-2 pyridinyl-N]phenyl-C]Iridium(III) hexafluorophosphate: $[Ir\{dF(CF_3)ppy\}_2(dtbpy)]PF_6$ In the synthetic schemes described below, unless otherwise indicated all temperatures are set forth in degrees Celsius and all parts and percentages are by weight. Reagents and solvents were purchased from commercial suppliers such as Aldrich Chemical Company and were used without further purification unless otherwise indicated. Tetrahydrofuran (THF) and N,N-dimethylformamide (DMF) were purchased from commercial sources in Sure Seal bottles and used as received.

The reactions set forth below were done generally under a positive pressure of argon or nitrogen at an ambient temperature (unless otherwise stated) in anhydrous solvents. Glassware was oven dried and/or heat dried. The reactions were assayed by TLC and/or analyzed by LC-MS and terminated as judged by the consumption of starting material. Analytical thin layer chromatography (TLC) was performed on glass plates pre-coated with silica gel 60 F254 0.25 mm plates (EM Science), and visualized with UV light (254 nm) and/or heating with commercial ethanolic phosphomolybdic acid. Preparative thin layer chromatography (TLC) was performed on glass-plates pre-coated with silica gel 60 F254 0.5 mm plates (20×20 cm, from commercial sources) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and sometimes noted as solvents removed in vacuo. Column chromatography was completed under positive pressure using 230-400 mesh silica gel.

One of the typical synthetic methods is described below.

Method 1A:

Synthesis of (R,1³E,1⁴E)-3⁵-fluoro-6-methyl-7-aza-1(5,3)-pyrazolo[1,5-a]pyrimidine-3(3,2)-pyridina-2(1,2)-pyrazalidinacyclooctaphan-8-one (Compound 1-8)

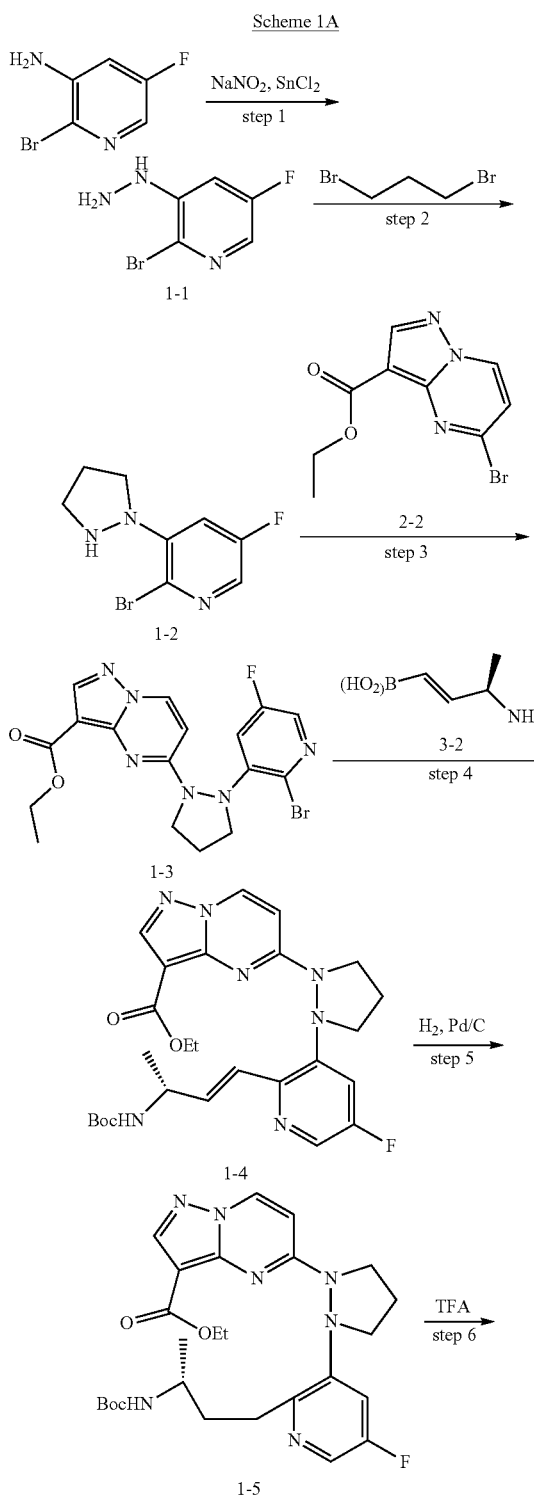

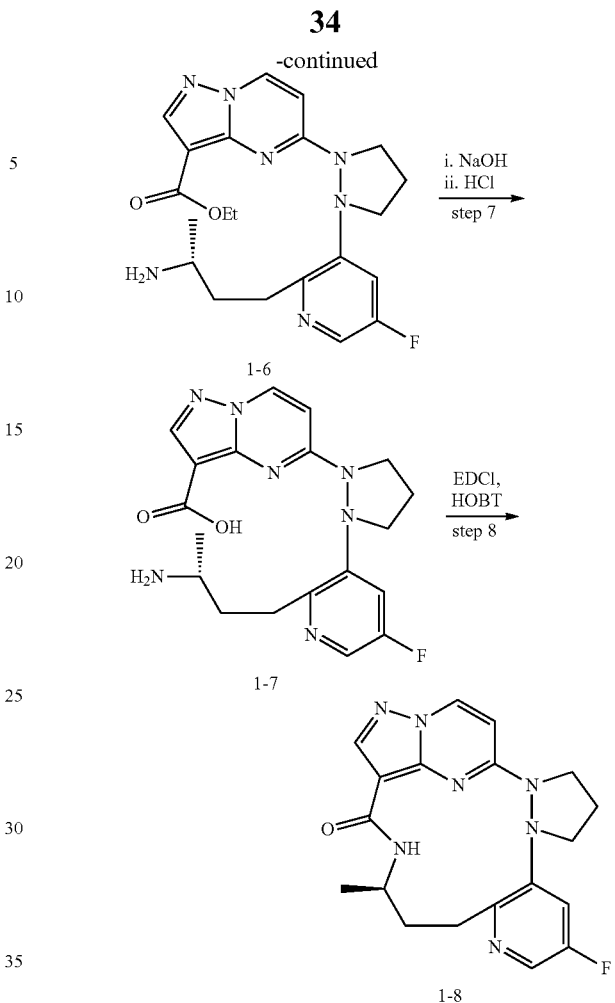

Step 1: synthesis of 2-bromo-5-fluoro-3-hydrazinylpyridine

To a stirred solution of 10.0 g (52.36 mmol) 2-bromo-5-fluoropyridin-3-amine in 58.5 mL of 6 N HCl was added dropwise 3.6 g of $NaNO_2$ (52.36 mmol) in 5.8 mL of $H_2O$ at 0° C. After 30 min, a solution of 29.8 g (157.28 mmol) of $SnCl_2$ in 11.7 mL of 6 N HCl was added dropwise at 0° C. over 5 min. The mixture was stirred at 0° C. for 30 min and at rt overnight. The reaction was quenched by addition of 100 mL of 40% KOH at 0° C. It was extracted with three 400 mL portions of ethyl acetate. The combined organic extracts were washed with brine, and dried over anhydrous $Na_2SO_4$. After filtration, the filtrate was concentrated under reduced pressure to afford a residue, which was purified by chromatography on silica gel column eluted with 20% of ethyl acetate in petroleum ether to afford compound 1-1. LC-MS: m/e=206 [M+H]⁺.

Step 2:

To a solution of 0.50 g (2.43 mmol) of compound 1-1 in 2 mL of DMF were added 1.50 g (4.85 mmol) of $Cs_2CO_3$ followed by 0.49 g (2.43 mmol) of 1,3-dibromopropane. The mixture was stirred at rt for 6 h under $N_2$ atmosphere. The reaction was quenched by addition of 10 mL of ethyl acetate and 10 mL of water, and extracted with three 50 mL portions of ethyl acetate. The combined organic extracts were washed with brine, and dried over anhydrous $Na_2SO_4$. After filtration, the filtrate was concentrated under reduced pressure to afford a residue, which was purified by chromatography on silica gel column eluted with 33% of ethyl acetate in petroleum ether to afford compound 1-2. LC-MS: m/e=246 [M+H]+.

Step 3:

To a solution of 0.28 g (1.14 mmol) of compound 1-2 in 1.5 mL of EtOH were added 0.31 g (1.14 mmol) of compound 2-2 and 0.026 g (0.23 mmol) of TFA at room temperature. The mixture in a sealed tube was stirred at 90° C. overnight under N₂ atmosphere and cooled to rt. It was diluted with 10 mL of ethyl acetate and 50 mL of water, and extracted with three 50 mL portions of ethyl acetate. The combined organic extracts were washed with brine, and dried over anhydrous Na₂SO₄. After filtration, the filtrate was concentrated to afford a residue, which was purified by chromatography on silica gel column eluted with 50% of ethyl acetate in petroleum ether to afford compound 1-3. LC-MS: m/e=435 [M+H]+.

Step 4:

To a solution of 0.16 g (0.37 mmol) of compound 1-3 in 8 mL of THF and 0.08 mL of water were added 0.12 g (0.55 mmol) of compound 3-2, 0.23 g (1.10 mmol) of K₃PO₄, 0.070 g (0.15 mmol) of XPhos, and 0.083 g (0.04 mmol) of Pd(OAc)₂. The mixture in a sealed tube was stirred at 70° C. for 2 h under N₂ atmosphere and cooled to rt. It was quenched by addition of 50 mL of water, and then extracted with three 50 mL portions of ethyl acetate. The combined organic extracts were washed with brine, and dried over anhydrous Na₂SO₄. After filtration, the filtrate was concentrated to afford a residue, which was purified by chromatography on silica gel column eluting with 50% of ethyl acetate in petroleum ether to afford compound 1-4. LC-MS: m/e=526 [M+H]+.

Step 5:

To a solution of 0.13 g (0.25 mmol) of compound 1-4 in 1 mL of MeOH was added 0.13 g of 20% Pd(OH)₂/C at room temperature. The mixture was stirred at rt for 1 h under hydrogen atmosphere and filtered. The filter cake was washed with three 20 ml portions of MeOH. The combined filtrates were concentrated to afford compound 1-5. LC-MS: m/e=528 [M+H]+.

Step 6:

To a stirred solution of 0.9 mL of DCM and 0.3 mL of TFA was added 0.11 g (0.21 mmol) of compound 1-5. The mixture was stirred at rt for 1 h and concentrated under vacuum to afford a residue, which was purified by chromatography on silica gel column eluting with 10% of methanol in dichloromethane to give compound 1-6. LC-MS: m/e=428 [M+H]+.

Step 7:

To a solution of 0.070 g (0.16 mmol) of compound 1-6 in 1 mL of EtOH and 0.1 mL of H₂O was added 0.066 g (1.64 mmol) of NaOH. The mixture in a sealed tube was stirred at 70° C. for 1 h and cooled down to rt. It was diluted with 20 mL of water, acidified to pH 5 with 1 N HCl, and then extracted with three 10 mL portions of DCM. The aqueous layer was concentrated under vacuum to afford a residue, which was suspended in 10 mL of MeOH and stirred at rt for 2 min. Then it was filtered, and the filter cake was washed with three 10 mL portions of MeOH. The combined filtrates were concentrated to afford compound 1-7, which was used in the next step without further purification. LC-MS: m/e=400 [M+H]+.

Step 8:

To a stirred solution of 0.05 g (0.13 mmol) of compound 1-7 in 0.9 mL of DMF and 1.8 mL of DCM were added 0.05 g (0.35 mmol) of HOBT and 0.07 g (0.40 mmol) of EDCI. After 10 min, 0.038 g (0.4 mmol) of TEA was introduced dropwise. The mixture was stirred at rt for additional 6 h, and extracted with three 50 mL portions of ethyl acetate. The combined organic extracts were washed with brine, and dried over anhydrous Na₂SO₄. After filtration, the filtrate was concentrated to afford a residue, which was purified by Prep-HPLC (Column, Poroshell HPH-C18, 3.0*50 mm, 2.7 μm; Mobile Phase A: water/5 mM NH₄HCO₃, Mobile Phase B: Acetonitrile; Flow rate: 1.2 mL/min; Gradient:10% B to 95% B in 2.1 min, hold 0.6 min; 254 nm UV) to give compound 1-8. LC-MS: m/e=382 [M+H]+.

Method 1B:

Synthesis of (R,1³E,1⁴E)-6-methyl-7-aza-1(5,3)-pyrazolo[1,5-a]pyrimidine-2(1,2)-pyrazolidina-3(1,2)-benzacyclooctaphan-8-one (Compound 1-17)

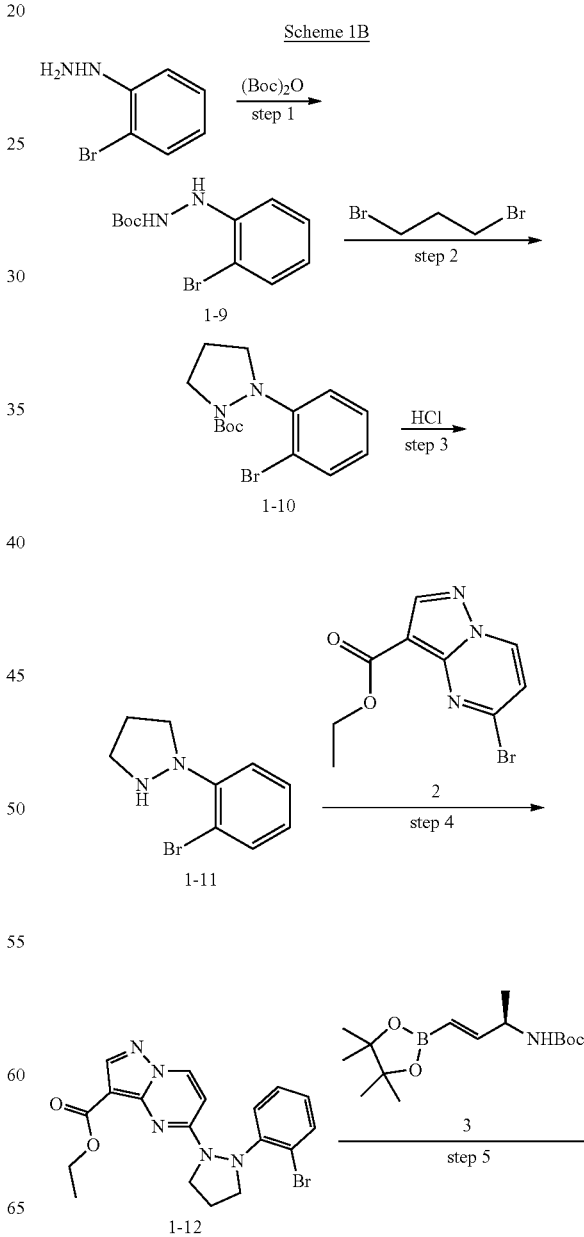

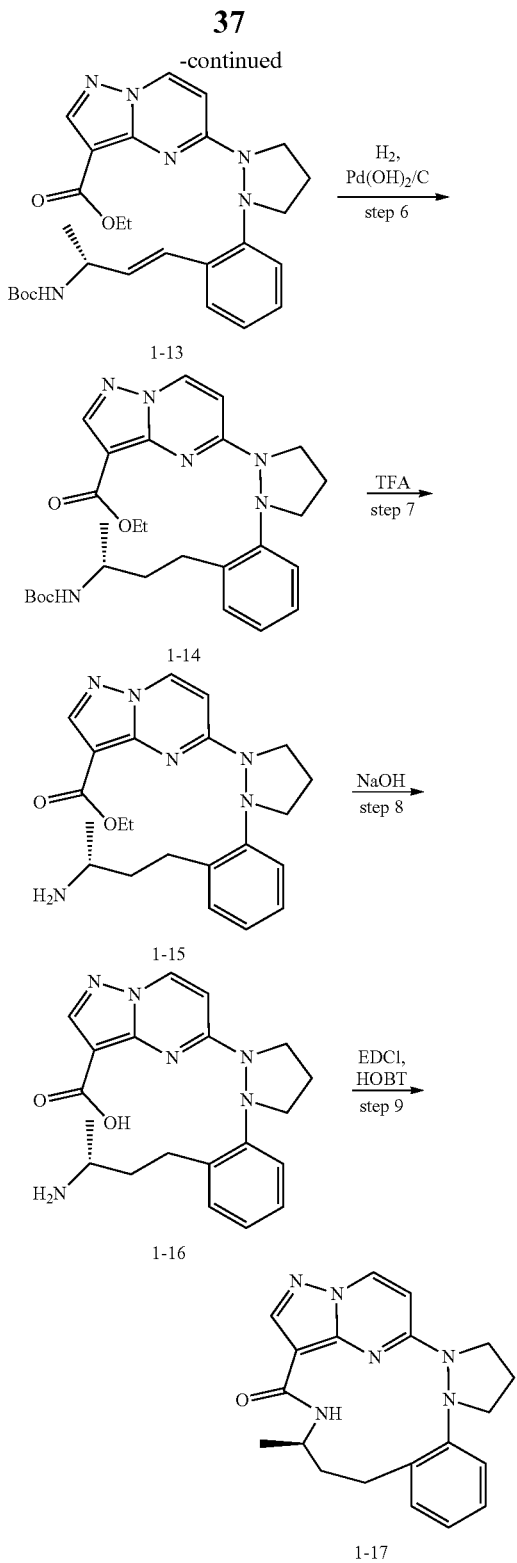

mL of brine, dried over anhydrous Na$_2$SO$_4$. After filtration, the filtrate was concentrated under reduced pressure to afford a residue, which was purified by chromatography on silica gel column eluting with 0-50% of ethyl acetate in petroleum ether to afford compound 1-9. LC-MS: m/e=287 [M+H]$^+$.

Step 2:
To a stirred solution of 5.9 g (29 mol) of 1,3-dibromopropane in 80 mL of DMF were added 1.4 g (59 mmol) of NaH (60% in coal oil) in portions at 0° C., and then 8.4 g (29 mol) of compound 1-9 in portions. The mixture was stirred at room temperature overnight under nitrogen atmosphere. The reaction was quenched by addition of 400 mL of ice water and extracted with three 200 mL portions of ethyl acetate. The combined organic extracts were washed with brine and dried over anhydrous Na$_2$SO$_4$. After filtration, the filtrate was concentrated to afford crude compound 1-10, which was used in the next step directly without further purification. LC-MS: m/e=327 [M+H]$^+$.

Step 3:
To a stirred solution of 8.5 g (26 mmol) compound 1-10 in 1,4-dioxane was added 40 mL of HCl (4 M) in dioxane dropwise at room temperature. The mixture was stirred at rt for 3 h and concentrated under vacuum to give a residue, which was purified by reverse flash chromatography with the following conditions: column, C18 silica gel; mobile phase, A: 0.05% formic acid in Water, B: Acetonitrile, 60% to 70% gradient in 30 mins; detector, UV 254 nm to afford compound 1-11 as hydrochloride salt. LC-MS: m/e=227 [M+H]$^+$.

Step 4:
To a solution of 2.8 g (11 mmol) compound 1-11 hydrogen chloride salt and 2.9 g (11 mmol) of compound 2 in 50 mL of EtOH was added 4.35 g (43.1 mmol) of Et$_3$N. The mixture was stirred at 90° C. for 2 h under nitrogen atmosphere and cooled to rt. It was concentrated under reduced pressure to afford a residue, which was purified by chromatography on silica gel column eluting with 20% of ethyl acetate in petroleum ether to afford compound 1-12. LC-MS: m/e=416 [M+H]$^+$.

Step 5:
To a solution of 0.30 g (0.72 mmol) compound 1-12 in 30 mL of DME were added 0.21 g (0.72 mmol) of compound 3, 0.05 g (0.04 mmol) of Pd(PPh$_3$)$_4$ and 6 mL of saturated NaHCO$_3$ solution. The solution was stirred for at 100° C. for 3 h under nitrogen atmosphere and cooled to rt. It was diluted with 50 mL of ethyl acetate, washed with three 20 mL portions of water. The organic phase was washed with 20 mL of brine and dried over anhydrous Na$_2$SO$_4$. After filtration, the filtrate was concentrated under reduced pressure to afford a residue, which was purified by reverse phase flash chromatography (column, C18 silica gel; mobile phase, A: 0.05% ammonium bicarbonate in Water, B: Acetonitrile, 0% to 60% gradient in 30 mins; detector, UV 254 nm) to afford compound 1-13. LC-MS: m/e=507 [M+H]$^+$.

Step 6:
To a solution of 0.26 g (0.51 mmol) compound 1-13 in 5 mL of MeOH was added 0.23 g 20 wt % Pd(OH)$_2$/C under nitrogen atmosphere. The mixture was stirred at room temperature for 30 min under hydrogen atmosphere, filtered through a Celite pad; the filter cake was washed with three 20 mL portions of MeOH. The filtrate was concentrated under reduced pressure to afford crude compound 1-14, which was used in the next step directly without further purification. LC-MS: m/e=509 [M+H]$^+$.

Step 1:
To a stirred solution of 8.0 g (36 mmol) of (2-bromophenyl)hydrazine hydrochloride and 10.2 g (46.5 mol) of (Boc)$_2$O in MeOH was added 10.9 g (107 mmol) of Et$_3$N dropwise at room temperature. The mixture was stirred at 50° C. for 5 h under nitrogen atmosphere, diluted with 500 mL of ethyl acetate. It was washed with three 100 mL portions of water; the organic phase was washed with 200

Step 7:

To a solution of 0.26 g (0.51 mmol) compound 1-14 in 4 mL of CH$_2$Cl$_2$ was added 2 mL of trifluoroacetic acid. The solution was stirred at rt for 30 min and concentrated under vacuum to afford crude compound 1-15 as TFA salt, which was used in the next step directly without further purification. LC-MS: m/e=409 [M+H]$^+$.

Step 8:

To a solution of 0.26 g (0.64 mmol) compound 1-15 TFA salt in 10 mL of EtOH and 1 mL of water was added 0.25 g (6.4 mmol) of NaOH. The solution was stirred at 70° C. for 30 min. and concentrated under vacuum to afford a residue, which was purified by chromatography on silica gel column eluting with 33% of methanol in ethyl acetate to afford compound 1-16. LC-MS: m/e=381 [M+H]$^+$.

Step 9:

To a solution of 0.12 g (0.32 mmol) compound 1-16 in 3 mL of DMF and 5 mL of CH$_2$Cl$_2$ were added 0.13 g (0.95 mmol) of HOBt and 181 mg (0.950 mmol) of EDCI and 0.096 g (0.95 mmol) of Et$_3$N. The solution was stirred at rt overnight. It was diluted with 20 mL of CH$_2$Cl$_2$, washed with two 10 mL portions of water. The organic phase was washed with 20 mL of brine and dried over anhydrous Na$_2$SO$_4$. After filtration, the filtrate was concentrated under reduced pressure to afford a residue, which was purified by Prep-HPLC with (Column, XBridge Prep OBD C18 Column, 30*150 mm 5 um; mobile phase, Water (10 mM NH$_4$HCO$_3$) and ACN (25% Phase B to 43% in 8 min; Detector, UV) to give compound 1-17. LC-MS: m/e=363 [M+H]$^+$.

Method 2:

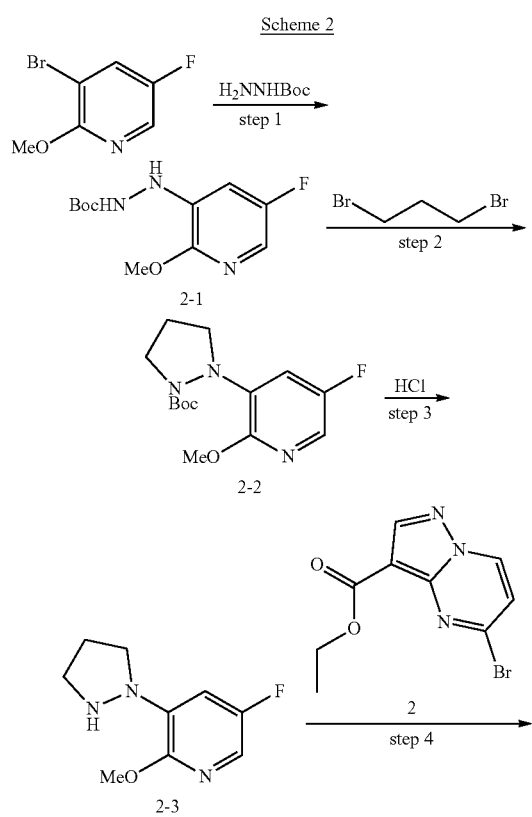

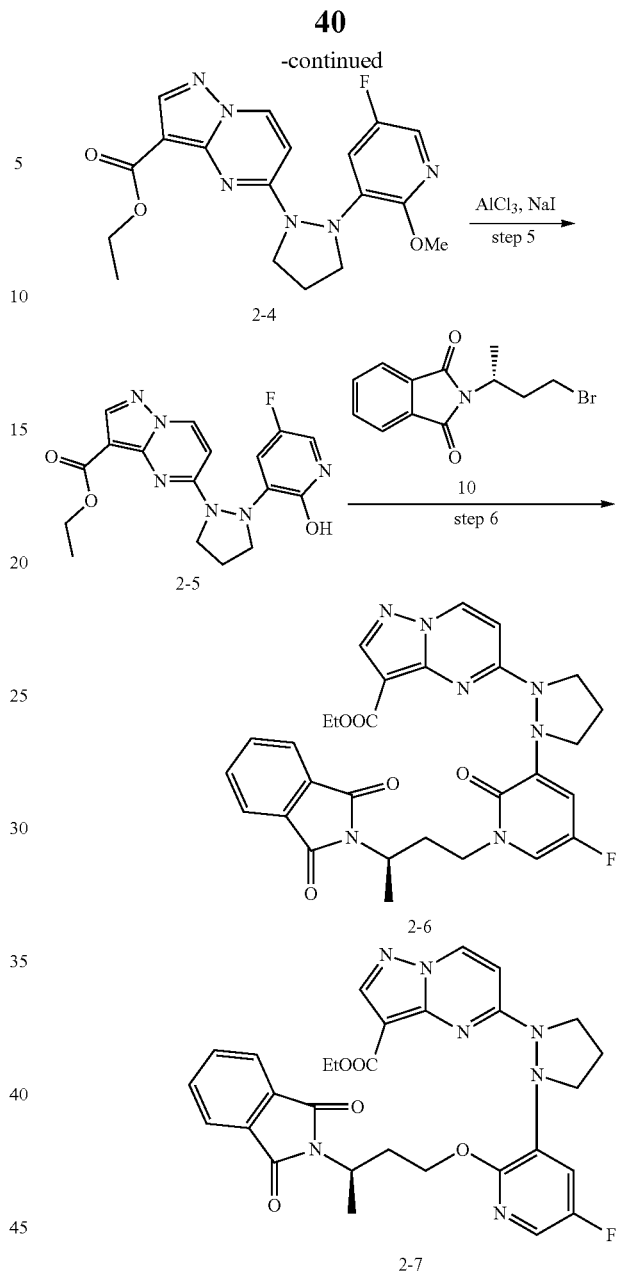

Step 1:

To a stirred solution of 5.0 g (24 mmol) of 3-bromo-5-fluoro-2-methoxypyridine in 35 mL of toluene were added 3.2 g (24 mmol) of (tert-butoxy)carbohydrazide, 1.0 g (1.4 mmol) of Pd(dppf)Cl$_2$ and 4.0 g (12 mmol) of Cs$_2$CO$_3$. The mixture was stirred at 105° C. for 2 h under nitrogen atmosphere and cooled to rt. The mixture was concentrated to afford a residue, which was purified by silica gel column chromatography eluting with 0 to 10% gradient of ethyl acetate in petroleum ether to afford compound 2-1. LC-MS: m/e=258 [M+H]$^+$.

Step 2:

To a stirred solution of 1.6 g (6.2 mmol) of compound 2-1 in 20 mL of DMF was added 4.1 g (13 mmol) of Cs$_2$CO$_3$ and 1.3 g (6.4 mmol) of 1,3-dibromopropane dropwise at rt. The mixture was stirred at rt overnight. It was diluted with 100 mL of water and extracted with three 50 mL portions of ethyl acetate. The combined organic layers were washed with 100 mL of brine, dried over anhydrous $Na_2SO_4$. After filtered, the filtrate was concentrated to afford a residue, which was purified by silica gel column chromatography eluting with 0 to 10% of MeOH in DCM to afford compound 2-2. LC-MS: m/e=298 $[M+H]^+$.

Step 3:

To a stirred solution of 1.5 g (5.0 mmol) of compound 2-2 in 10 mL of 1,4-dioxane was added 10 mL of HCl (4 M) in 1,4-dioxane dropwise at rt. The mixture was concentrated under reduced pressure to afford a residue, which was purified by silica gel column chromatography eluting with 0 to 15% gradient of MeOH in $CH_2Cl_2$ to afford compound 2-3 as hydrochloride salt. LC-MS: m/e=198 $[M+H]^+$.

Step 4:

To a stirred solution of 0.48 g (2.1 mmol) of compound 2-3 hydrochloride salt in 8 mL of DMSO was added 0.95 g (16.4 mmol) of KF in portions at rt. After 30 min, to the above solution was added 0.55 g (2.1 mmol) of compound 2. The mixture was stirred at 80° C. for additional 2 h and cooled to rt. It was diluted with 50 mL of water, extracted with three 30 mL portions of ethyl acetate. The combined organic extracts were washed with 50 mL of brine, dried over $Na_2SO_4$. After filtration, the filtrate was concentrated to afford a residue, which was purified by chromatography on silica gel column eluting with 0 to 50% gradient of ethyl acetate in petroleum ether to afford compound 2-4. LC-MS: m/e=387 $[M+H]^+$.

Step 5:

To a stirred solution of 0.10 g (0.26 mmol) of compound 2-4 in 10 mL of acetonitrile were added 0.35 g (2.6 mmol) of $AlCl_3$ and 0.43 g (2.9 mmol) of NaI in portions at 0° C. The mixture was stirred at rt for 4 h under $N_2$ atmosphere. The reaction was quenched by addition of 10 mL of $H_2O$ at 0° C. and extracted with three 30 mL portions of ethyl acetate. The combined organic extracts were washed with 50 mL of brine and dried over $Na_2SO_4$. After filtration, the filtrate was concentrated to afford a residue, which was purified by chromatography on silica gel column eluting with 0 to 50% gradient of ethyl acetate in petroleum ether to afford compound 2-5. LC-MS: m/e=373 $[M+H]^+$.

Step 6:

To a stirred solution of 0.25 g (0.70 mmol) of compound 2-5 in 3 mL of DMF were added 0.28 g (1.0 mmol) of compound 10 and 0.027 g (3.4 mmol) of lithium hydride in portions. The mixture was stirred at 70° C. for 2 h under nitrogen atmosphere and cooled to rt. It was quenched with saturated $NH_4Cl$ solution, extracted with three 20 mL portions of ethyl acetate. The combined organic extracts were washed with 20 mL of brine, dried over $Na_2SO_4$. After filtration, the filtrate was concentrated to afford a residue, which was purified by Prep. TLC eluting with 5% MeOH in DCM to afford compound 2-6 and 2-7. LC-MS for compound 2-6: m/e=574 $[M+H]^+$. LC-MS for compound 2-7: m/e=574 $[M+H]^+$.

Method 3:

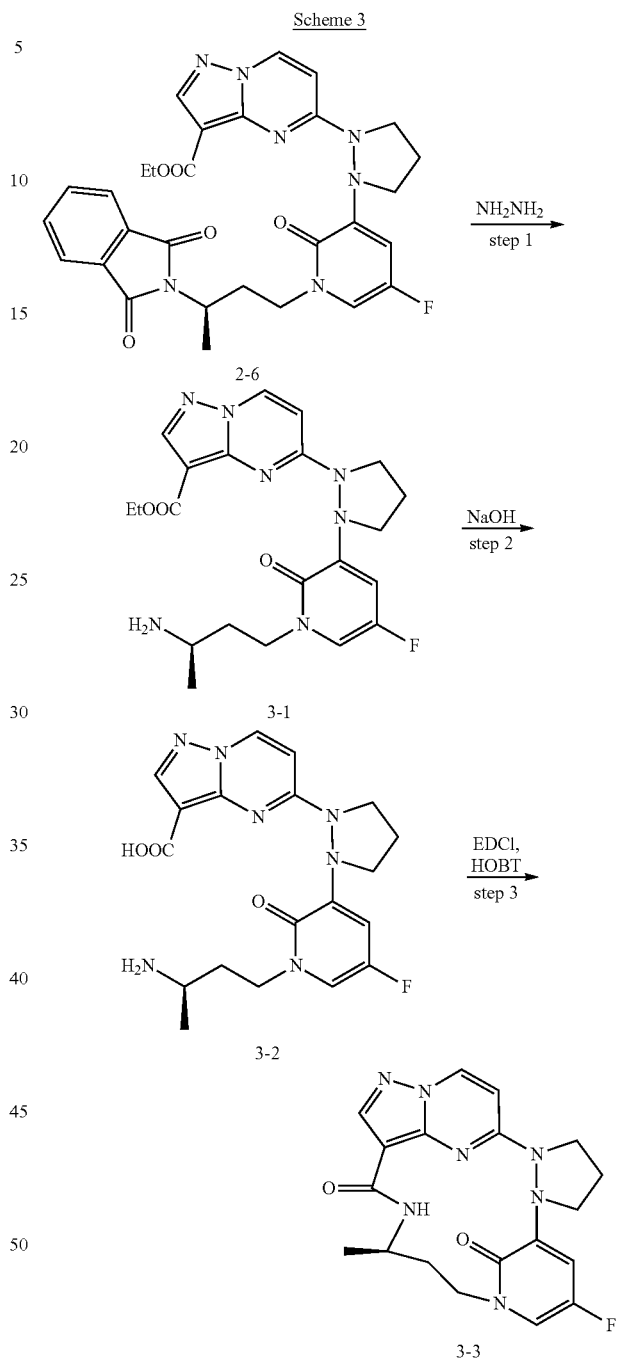

Scheme 3

Step 1:

To a stirred solution of 0.14 g (0.24 mmol) of compound 2-6 in 2 mL of EtOH was added 0.058 g (1.2 mmol) of hydrazine hydrate in portions. The mixture was stirred at 70° C. for 1.5 h under nitrogen atmosphere and was cooled to rt. It was diluted with 15 mL of $H_2O$ and extracted with three 30 mL portions of ethyl acetate. The combined organic extracts were washed with 30 mL of brine and dried over $Na_2SO_4$. After filtration, the filtrate was concentrated to afford crude compound 3-1, which was used in the next step without further purification. LC-MS: m/e=444 $[M+H]^+$.

Step 2:
Compound 3-1 was converted to compound 3-2 following similar procedures described in Method 1, step 8. LC-MS: m/e=416 [M+H]⁺.

Step 3:
Compound 3-2 was converted to compound 3-3 following similar procedures described in Method 1, step 9. LC-MS: m/e=398 [M+H]⁺.

Method 4:

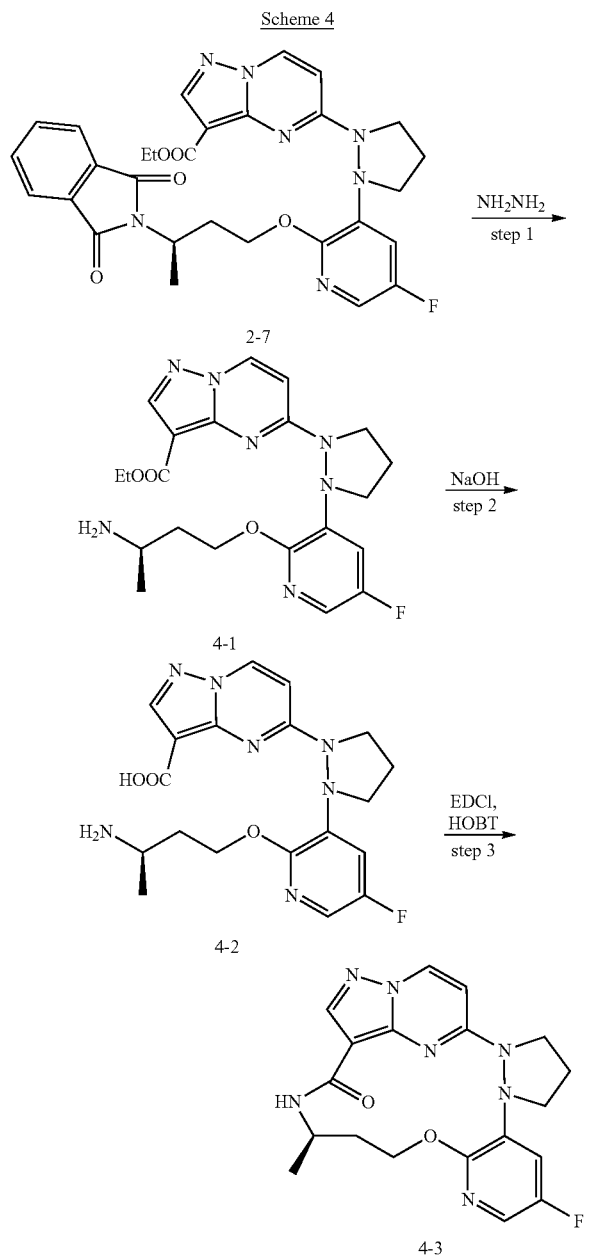

Step 1:
Compound 2-7 was converted to compound 4-1 following similar procedures described in Method 3, step 1. LC-MS: m/e=444 [M+H]⁺.

Step 2:
Compound 4-1 was converted to compound 4-2 following similar procedures described in Method 1, step 8. LC-MS: m/e=416 [M+H]⁺.

Step 3:
Compound 4-2 was converted to compound 4-3 following similar procedures described in Method 1, step 9. LC-MS: m/e=398 [M+H]⁺.

Method 5:

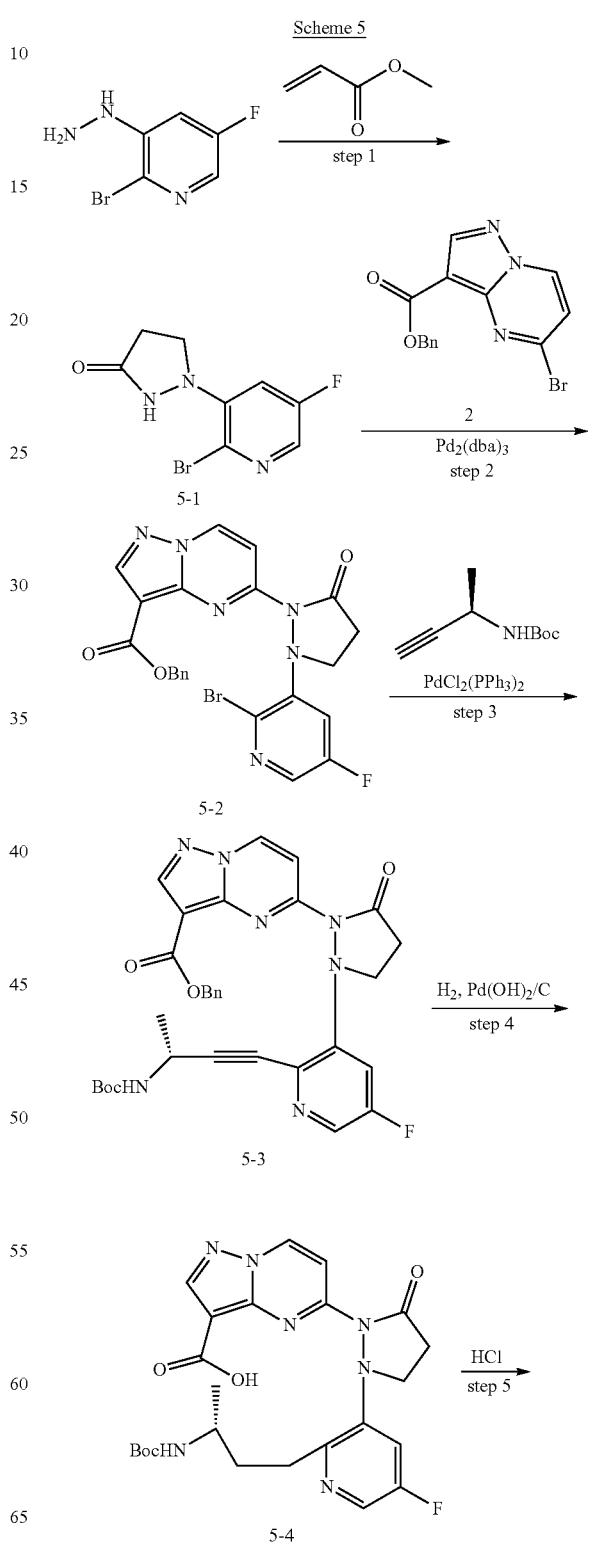

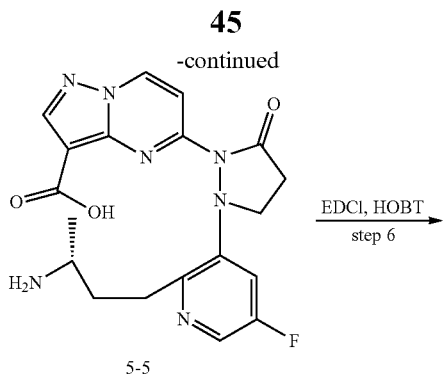

5-5

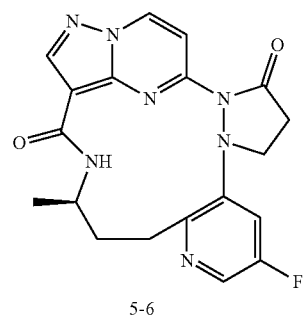

5-6

Step 1:

To a stirred solution of 1.6 g (7.8 mmol) 2-bromo-5-fluoro-3-hydrazinylpyridine in 20 mL of ethanol was added 3.2 g (47 mmol) of EtONa and 1.3 g (16 mmol) of methyl prop-2-enoate at room temperature. The mixture was stirred at 60° C. for 2 h under nitrogen atmosphere, diluted with 100 mL of water. The aqueous layer was extracted with three 100 mL portions of EtOAc. The combined organic extracts were washed with 100 mL of brine, dried over anhydrous $Na_2SO_4$. After filtration, the filtrate was concentrated under reduced pressure to afford a residue, which were purified by reverse phase flash chromatography (column, C18 silica gel, mobile phase, A: 0.05% formic acid in Water, B: Acetonitrile, 0% to 100% gradient in 30 mins; detector, UV 254 nm to afford compound 5-1. LC-MS: m/e=260 [M+H]$^+$.

Step 2:

To a solution of 0.40 g (1.5 mmol) of compound 5-1, 1.0 g (3.1 mmol) of compound 22-2 in 10 mL of dioxane were added 2.2 mg (0.0030 mmol) of XantPhos, 3.5 mg (0.0030 mmol) of $Pd_2(dba)_3$ and 19 mg (0.060 mmol) of $Cs_2CO_3$ at rt. The mixture was stirred at 100° C. for 2 h under nitrogen atmosphere and cooled to rt. The mixture was diluted with 50 mL of water, extracted with three 50 mL portions of ethyl acetate. The combined organic extracts were washed with 50 mL of brine, dried over anhydrous $Na_2SO_4$. After filtration, the filtrate was concentrated under reduced pressure to afford a residue, which was purified by chromatography on silica gel column eluting with 50% of ethyl acetate in petroleum ether to afford compound 5-2. LC-MS: m/e=511 [M+H]$^+$.

Step 3:

Into a 20 mL sealed tube were added 180 mg (0.35 mmol) of compound 5-2, 119 mg (0.700 mmol) of tert-butyl N-[(2R)-but-3-yn-2-yl]carbamate, 13 mg (0.070 mmol) of CuI, 89 mg (0.88 mmol) of i-$Pr_2NH$ and 50 mg (0.07 mmol) of $PdCl_2(PPh_3)_2$ in 8 mL of DMF at rt. The mixture was stirred 65° C. for 3 h under nitrogen atmosphere. The mixture was diluted with 50 mL of water, extracted with three 50 mL portions of ethyl acetate. The combined organic extracts were washed with 50 mL of brine, dried over anhydrous $Na_2SO_4$. After filtration, the filtrate was concentrated under reduced pressure to afford a residue, which was purified by chromatography on silica gel column eluting with 50% of ethyl acetate in petroleum ether to afford compound 5-3. LC-MS: m/e=600 [M+H]$^+$.

Step 4:

Compound 5-3 was converted to compound 5-4 following similar procedures described in Method 1, step 6. LC-MS: m/e=514 [M+H]$^+$.

Step 5:

Compound 5-4 was converted to compound 5-5 following similar procedures described in Method 2, step 3. LC-MS: m/e=414 [M+H]$^+$.

Step 6:

Compound 5-5 was converted to compound 5-6 following similar procedures described in Method 1, step 9. LC-MS: m/e=396 [M+H]$^+$.

Method 6:

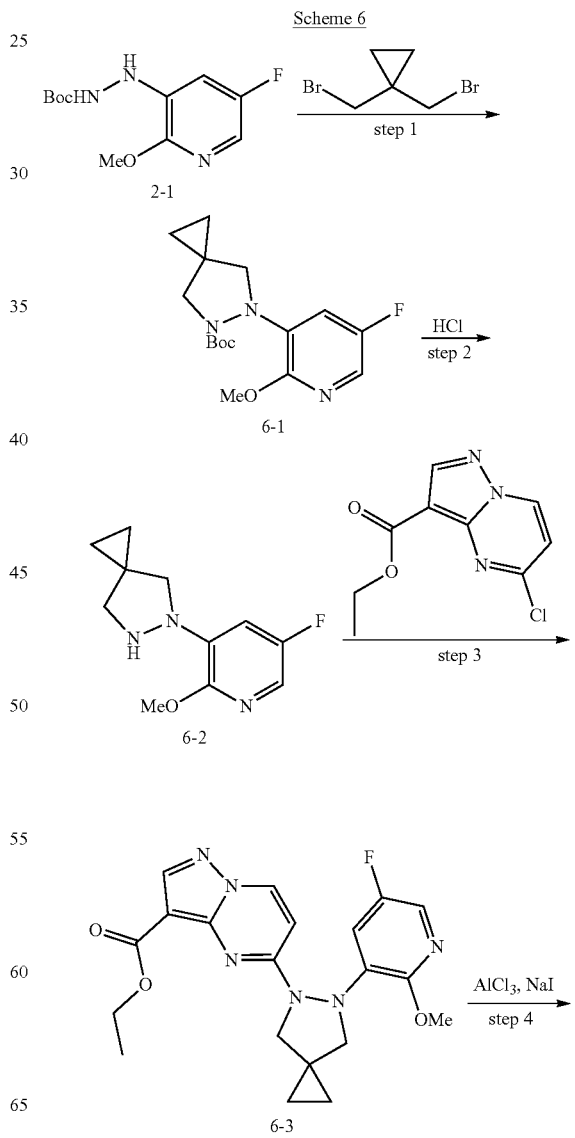

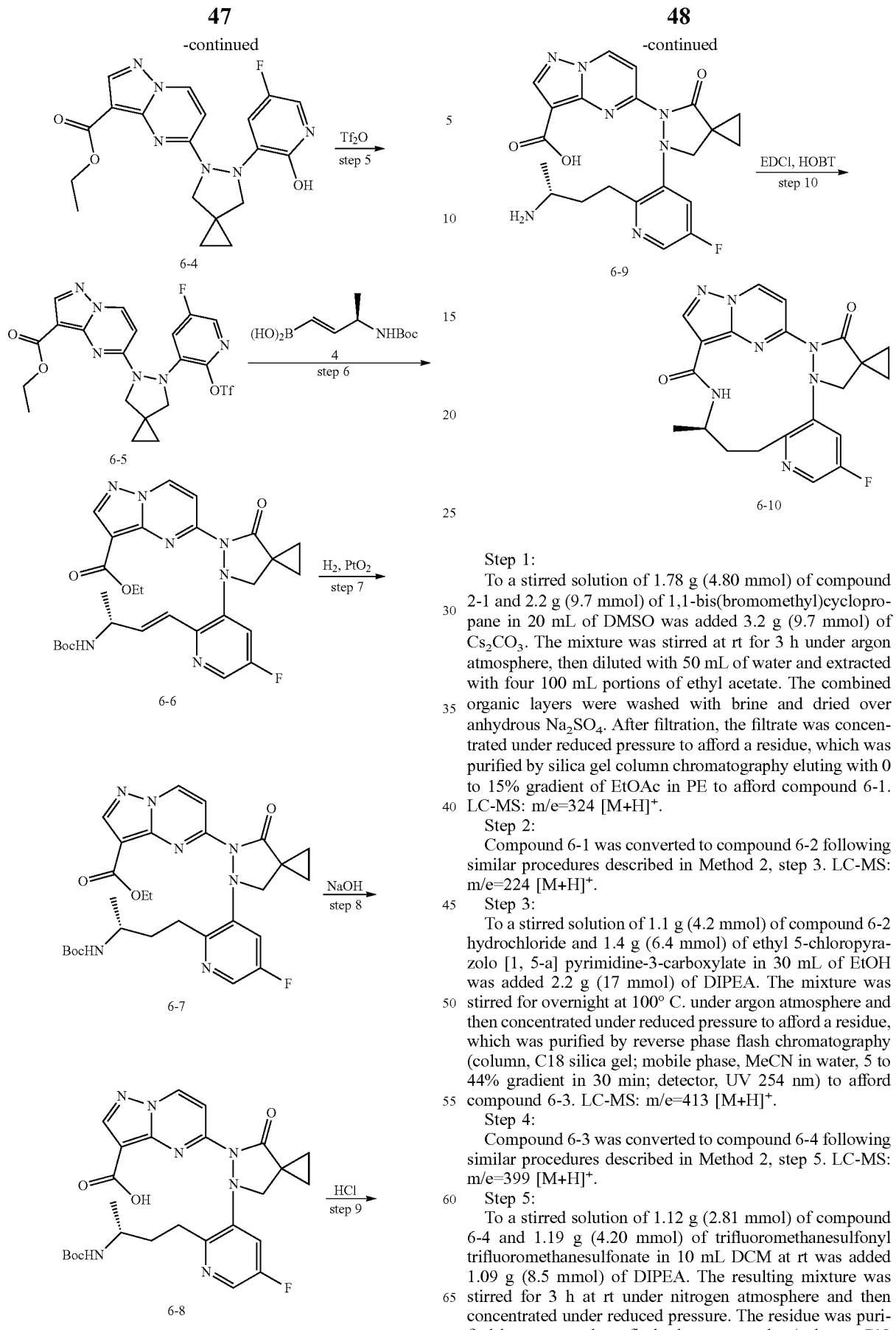

Step 1:

To a stirred solution of 1.78 g (4.80 mmol) of compound 2-1 and 2.2 g (9.7 mmol) of 1,1-bis(bromomethyl)cyclopropane in 20 mL of DMSO was added 3.2 g (9.7 mmol) of $Cs_2CO_3$. The mixture was stirred at rt for 3 h under argon atmosphere, then diluted with 50 mL of water and extracted with four 100 mL portions of ethyl acetate. The combined organic layers were washed with brine and dried over anhydrous $Na_2SO_4$. After filtration, the filtrate was concentrated under reduced pressure to afford a residue, which was purified by silica gel column chromatography eluting with 0 to 15% gradient of EtOAc in PE to afford compound 6-1. LC-MS: m/e=324 [M+H]$^+$.

Step 2:

Compound 6-1 was converted to compound 6-2 following similar procedures described in Method 2, step 3. LC-MS: m/e=224 [M+H]$^+$.

Step 3:

To a stirred solution of 1.1 g (4.2 mmol) of compound 6-2 hydrochloride and 1.4 g (6.4 mmol) of ethyl 5-chloropyrazolo [1, 5-a] pyrimidine-3-carboxylate in 30 mL of EtOH was added 2.2 g (17 mmol) of DIPEA. The mixture was stirred for overnight at 100° C. under argon atmosphere and then concentrated under reduced pressure to afford a residue, which was purified by reverse phase flash chromatography (column, C18 silica gel; mobile phase, MeCN in water, 5 to 44% gradient in 30 min; detector, UV 254 nm) to afford compound 6-3. LC-MS: m/e=413 [M+H]$^+$.

Step 4:

Compound 6-3 was converted to compound 6-4 following similar procedures described in Method 2, step 5. LC-MS: m/e=399 [M+H]$^+$.

Step 5:

To a stirred solution of 1.12 g (2.81 mmol) of compound 6-4 and 1.19 g (4.20 mmol) of trifluoromethanesulfonyl trifluoromethanesulfonate in 10 mL DCM at rt was added 1.09 g (8.5 mmol) of DIPEA. The resulting mixture was stirred for 3 h at rt under nitrogen atmosphere and then concentrated under reduced pressure. The residue was purified by reverse phase flash chromatography (column, C18 silica gel; mobile phase, MeCN in water, 5% to 35% gradient in 40 min; detector, UV 254 nm) to afford compound 6-5. LC-MS: m/e=531 [M+H]⁺.

Step 6:

To a stirred solution of 360 mg (0.70 mmol) of compound 6-5 and 219 mg (1.00 mmol) of compound 23-2 in 5 mL of THF was added 79 mg (0.070 mmol) of Pd(PPh₃)₄ and 288 mg (1.40 mmol) of K₃PO₄. The mixture was stirred at 70° C. for 3 h under argon atmosphere and then concentrated under vacuum to give a residue, which was purified by silica gel column chromatography eluting with 0 to 10% gradient of EtOAc in PE to afford compound 6-6. LC-MS: m/e=552 [M+H]⁺.

Step 7:

To a stirred solution of 260 mg (1.03 mmol) of compound 6-6 in 25 mL of MeOH was added 200 mg (0.88 mmol) of dioxoplatinum. The mixture was stirred for 1 h at room temperature under hydrogen atmosphere and then filtered to remove the catalyst. The filtrate was concentrated under reduced pressure to afford compound 6-7. LC-MS: m/e=554 [M+H]⁺.

Step 8:

Compound 6-7 was converted to compound 6-8 following similar procedures described in Method 1, step 8. LC-MS: m/e=526 [M+H]⁺.

Step 9:

Compound 6-8 was converted to compound 6-9 following similar procedures described in Method 2, step 3. LC-MS: m/e=426 [M+H]⁺.

Step 10:

Compound 6-9 was converted to compound 6-10 following similar procedures described in Method 1, step 9. LC-MS: m/e=408 [M+H]⁺.

Method 7:

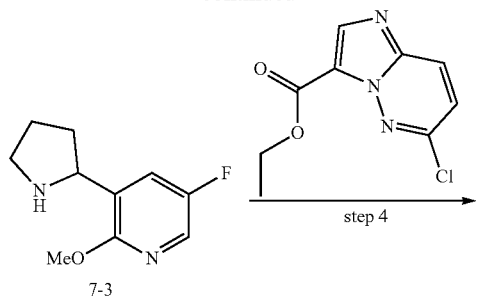
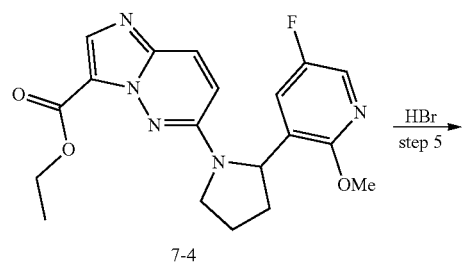
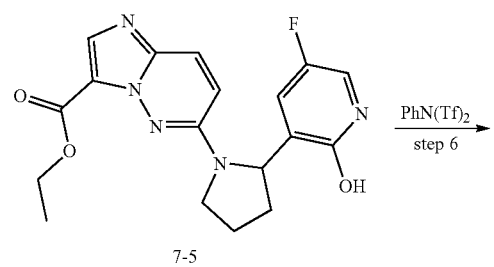
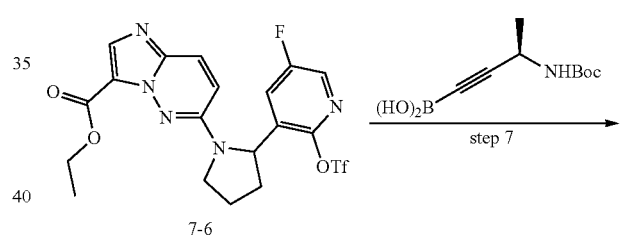
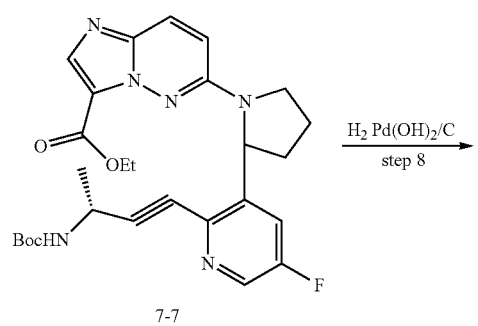
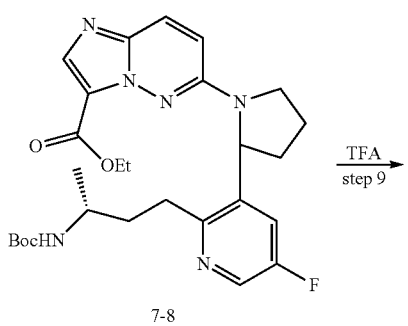
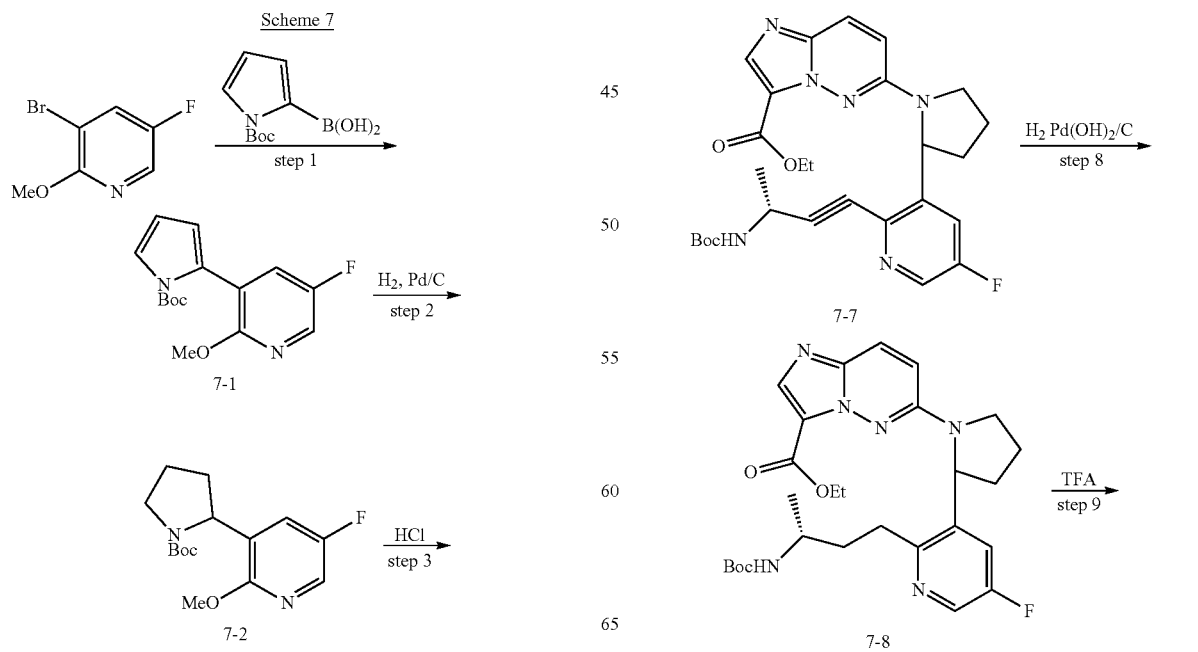

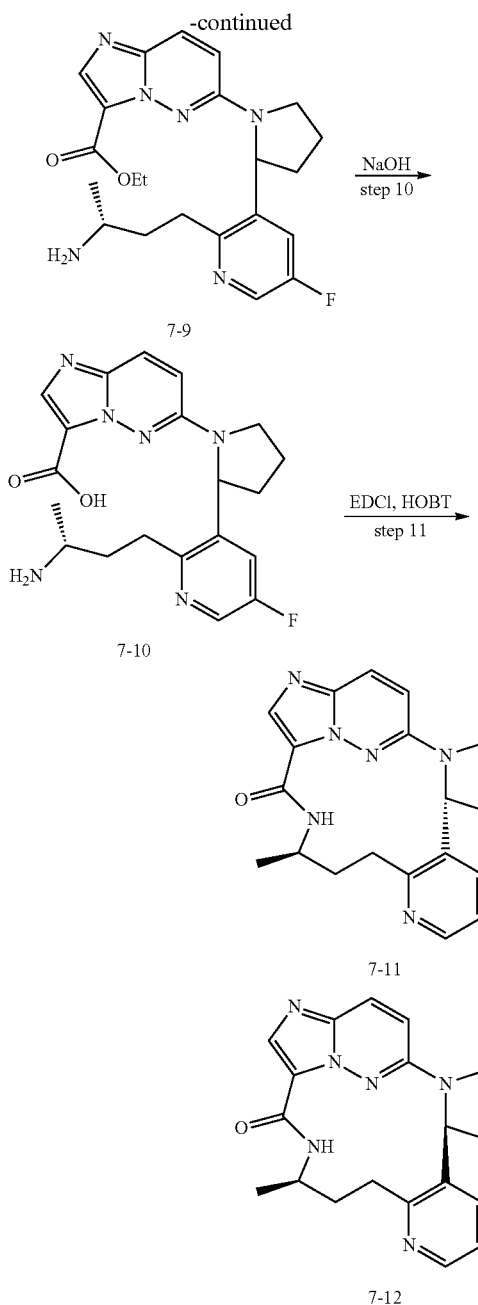

7-9

7-10

7-11

7-12

Step 1:

To a solution of 5.0 g (24 mmol) of 3-bromo-5-fluoro-2-methoxypyridine in 100 mL of THF and 10 mL of H$_2$O were added 5.1 g (24 mmol) of [1-[(tert-butoxy)carbonyl]-1H-pyrrol-2-yl]boronic acid, 0.27 g (1.2 mmol) of Pd(OAc)$_2$, 2.3 g (4.9 mmol) of XPhos and 15.4 g (72.8 mmol) of K$_3$PO$_4$ at rt. The mixture was stirred at 70° C. for overnight under nitrogen atmosphere and cooled down to rt. It was diluted with 500 mL of water and extracted with 500 mL of ethyl acetate. The combined organic extracts were washed with brine and dried over anhydrous Na$_2$SO$_4$. After filtration, the filtrate was concentrated to afford a residue, which was purified by chromatography on silica gel column eluting with 0 to 100% gradient of ethyl acetate in petroleum ether to afford compound 7-1. LC-MS: m/e=293 [M+H]$^+$.

Step 2:

To the solution of 10.2 g (3.04 mmol) compound 7-1 in 100 mL of MeOH was added 10.2 g (9.58 mmol) of 10 wt % Pd/C at rt. The mixture was stirred at 60° C. for 2 h under hydrogen atmosphere and cooled to rt. It was filtered and the filter cake was washed with three 100 mL portions of MeOH. The combined filtrates were concentrated under reduced pressure to afford a residue, which was purified by chromatography on silica gel column eluting with 0 to 30% of ethyl acetate in petroleum ether to afford compound 7-2. LC-MS: m/e=297 [M+H]$^+$.

Step 3:

Compound 7-2 was converted to compound 7-3 following similar procedures described in Method 2, step 3. LC-MS: m/e=197 [M+H]$^+$.

Step 4:

To a solution of 0.25 g (0.92 mmol) of compound 7-3 dihydrochloride salt in 23 mL of DMSO was added 0.19 g (0.86 mmol) of ethyl 6-chloroimidazo[1,2-b]pyridazine-3-carboxylate and 0.40 g (6.8 mmol) of KF. The mixture was stirred at 180° C. for 2 h and cooled down to rt. It was diluted with 250 mL of water and extracted with 250 mL of ethyl acetate. The combined organic extracts were washed with brine and dried over anhydrous Na$_2$SO$_4$. After filtration, the filtrate was concentrated to afford a residue, which was purified by Prep-TLC (ethyl acetate/petroleum ether=1:1) to afford compound 7-4. LC-MS: m/e=386 [M+H]$^+$.

Step 5:

To a solution of 0.21 g (0.56 mmol) of compound 7-4 in 11 mL of AcOH was added 1.36 g (5.60 mmol) of HBr (33%) in AcOH at rt. The mixture was stirred at 90° C. for 2 h and cooled to rt. The mixture was basified to pH 8 with saturated NaHCO$_3$ solution, extracted with two 250 mL portions of ethyl acetate. The combined organic layers were washed with three portions 250 mL of brine, dried over anhydrous Na$_2$SO$_4$. After filtration, the filtrate was concentrated under reduced pressure to afford a residue, which was purified by Prep-TLC eluting with 6% MeOH in DCM to afford compound 7-5. LC-MS: m/e=372 [M+H]$^+$.

Step 6:

To a solution of 0.060 g (0.16 mmol) of compound 7-5 in 1.9 mL of CH$_2$Cl$_2$ was added 45.8 mg (0.450 mmol) of Et$_3$N and 80.6 mg (0.230 mmol) of 1,1,1-trifluoro-N-phenyl-N-(trifluoromethane)sulfonylmethanesulfonamide at rt. The mixture was stirred for 2 h at 0° C. under nitrogen atmosphere. The mixture was stirred at rt overnight under nitrogen atmosphere. The reaction was quenched with 2.66 mL of saturated NaHCO$_3$ solution. It was extracted with two 50 mL portions of ethyl acetate. The combined organic layers were washed with 50 mL of brine, dried over anhydrous Na$_2$SO$_4$. After filtration, the filtrate was concentrated under reduced pressure to afford a residue, which was purified by Prep-TLC eluting with 5% MeOH in DCM to afford compound 7-6. LC-MS: m/e=504 [M+H]$^+$.

Step 7:

To a solution of 0.3 g (0.6 mmol) of compound 7-6 in 9 mL of THF were added 0.16 g (0.74 mmol) [(1E,3R)-3-[[(tert-butoxy)carbonyl]amino]but-1-en-1-yl]boronic acid, 20.7 mg (0.02 mmol) Pd(PPh$_3$)$_4$ and 0.24 g (1.13 mmol) K$_3$PO$_4$ at rt. The mixture was stirred at 50° C. overnight under nitrogen atmosphere and diluted with two 25 mL portions of ethyl acetate. The combined organic layers were washed with 25 mL of brine, then dried over anhydrous Na$_2$SO$_4$. After filtration, the filtrate was concentrated under reduced pressure to afford a residue, which was purified by reverse phase flash chromatography) column, C18 silica gel; mobile phase, A: 0.05% ammonium bicarbonate in Water, B:

Acetonitrile, 0 to 40% gradient in 50 mins; detector, UV 254 nm) to afford compound 7-7. LC-MS: m/e=523 [M+H]⁺.

Step 8:

Compound 7-7 was converted to compound 7-8 following similar procedures described in Method 1, step 6. LC-MS: m/e=527 [M+H]⁺.

Step 9:

Compound 7-8 was converted to compound 7-9 following similar procedures described in Method 1, step 7. LC-MS: m/e=427 [M+H]⁺.

Step 10:

Compound 7-9 was converted to compound 7-10 following similar procedures described in Method 1, step 8. LC-MS: m/e=399 [M+H]⁺.

Step 11:

Compound 7-10 was converted to compound 7-11 and 7-12, following similar procedures described in Method 1, step 9. The diastereoisomeric mixture was separated by Prep-HPLC (Column, XBridge Prep C18 OBD Column, 5 um, 19*150 mm; Mobile Phase, A: water (10 mmol/L NH₄HCO₃+0.1% NH₃.H₂O) and Mobile Phase B: ACN, Gradient: 27% Phase B to 37% in 8 min; (254 nm UV). LC-MS for compound 7-11: m/e=381 [M+H]⁺. LC-MS for compound 7-12: m/e=381 [M+H]⁺.

Method 8:

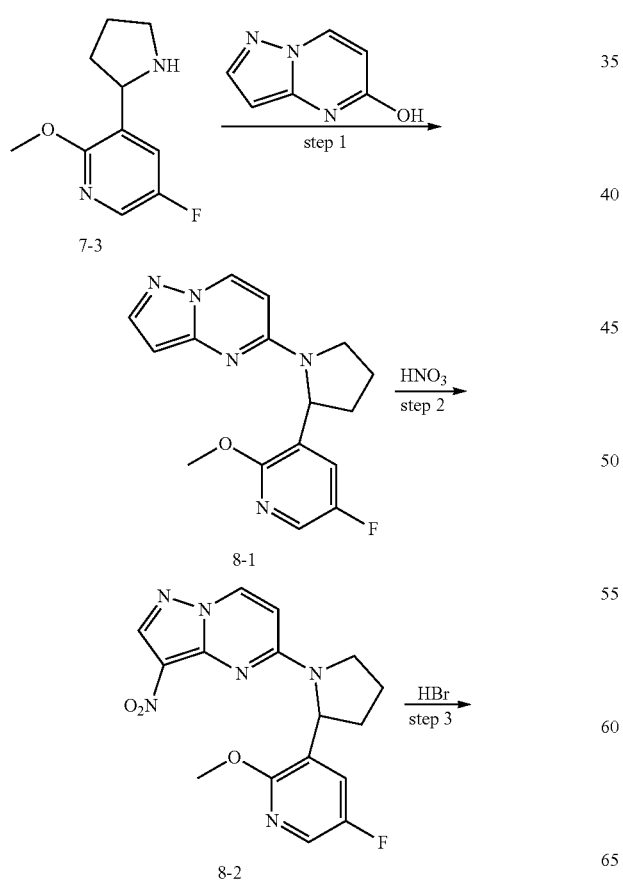

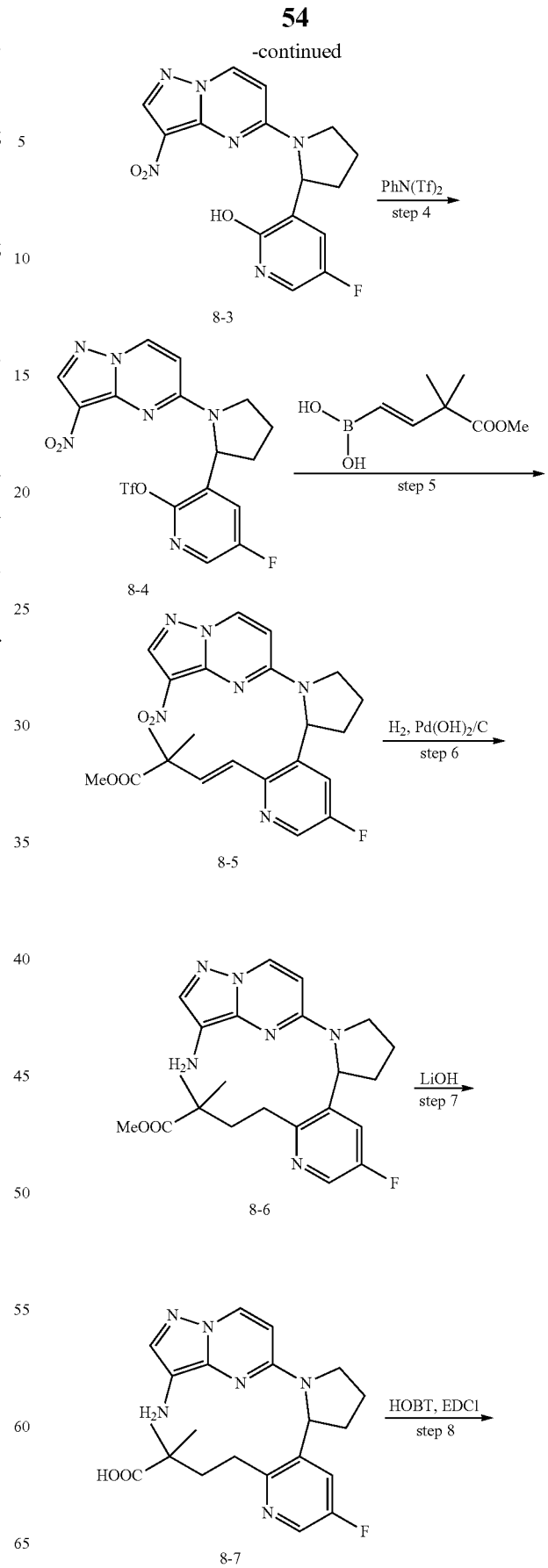

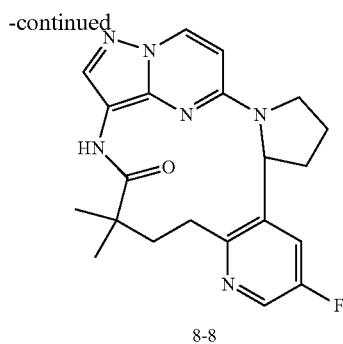

8-8

Step 1:

To a solution of 39 mg (0.20 mmol) of compound 7-3 HCl salt in 0.5 mL of DMF were added 20 mg (0.15 mmol) of pyrazolo[1,5-a]pyrimidin-5-ol, 77 mg (0.17 mmol) of BOP and 0.13 mL of DIPEA. The mixture was stirred at rt overnight under nitrogen atmosphere and then quenched by addition of 10 mL of 10% citric acid. The solution was diluted with 10 mL of ethyl acetate, washed with two 10 mL portions of saturated NaHCO$_3$ solution. The combined organic extracts were washed with 10 mL of brine, dried over anhydrous Na$_2$SO$_4$. After filtration, the filtrate was concentrated to afford a residue, which was purified by chromatography on silica gel column eluting with 0 to 60% gradient of ethyl acetate in petroleum ether to afford compound 8-1. LC-MS: m/e=314 [M+H]$^+$.

Step 2:

To a solution of 200 mg (0.64 mmol) compound 8-1 in 1.5 mL of trifluoroacetic acid was added 0.2 mL of HNO$_3$ in 1 mL of trifluoroacetic acid at rt. The mixture was stirred at rt for 15 min and then diluted with 10 mL of water. It was extracted with two 10 mL portions of ethyl acetate; the combined organic extracts were washed with 10 mL of brine, dried over anhydrous Na$_2$SO$_4$. After filtration, the mixture was concentrated to afford compound 8-2. LC-MS: m/e=359 [M+H]$^+$.

Step 3:

Compound 8-2 was converted to compound 8-3 following similar procedures described in Method 7, step 5. LC-MS: m/e=345 [M+H]$^+$.

Step 4:

Compound 8-3 was converted to compound 8-4 following similar procedures described in Method 7, step 6. LC-MS: m/e=477 [M+H]$^+$.

Step 5:

Compound 8-4 was converted to compound 8-5 following similar procedures described in Method 1, step 5, using benzyl (3E)-4-(4,5-dioxo-1,3,2-dioxaborolan-2-yl)-2,2-dimethylbut-3-enoate as the coupling reagent instead. LC-MS: m/e=455 [M+H]$^+$.

Step 6:

Compound 8-5 was converted to compound 8-6 following similar procedures described in Method 1, step 6. LC-MS: m/e=427 [M+H]$^+$.

Step 7:

To a solution of 180 mg (0.36 mmol) of compound 8-6 in 2 mL of CH$_3$OH and 1 mL of water was added 86 mg (3.6 mmol) of LiOH. The mixture was stirred at rt for 2 h and diluted with 10 mL of H$_2$O. The mixture was acidified to pH 5 with 2 N HCl, extracted with two 10 mL portions of ethyl acetate. The combined organic extracts were washed with 20 ml of brine, dried over anhydrous Na$_2$SO$_4$. After filtration, the filtrate was concentrated to afford compound 8-7. LC-MS: m/e=413 [M+H]$^+$.

Step 8:

Compound 8-7 was converted to compound 8-8 (racemic) following similar procedures described in Method 1, step 9. LC-MS: m/e=395 [M+H]$^+$.

Method 9:

Scheme 9

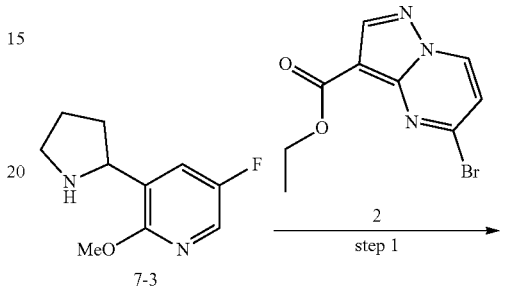

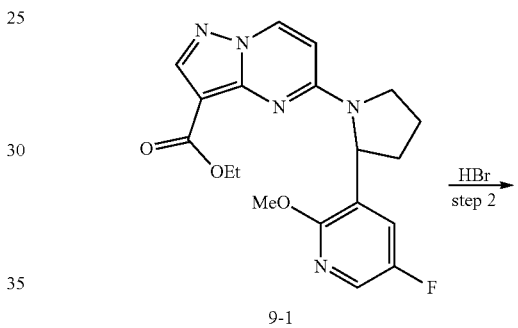

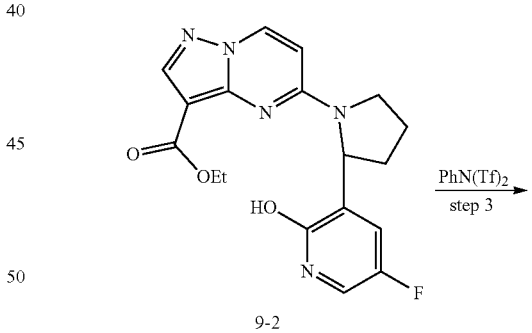

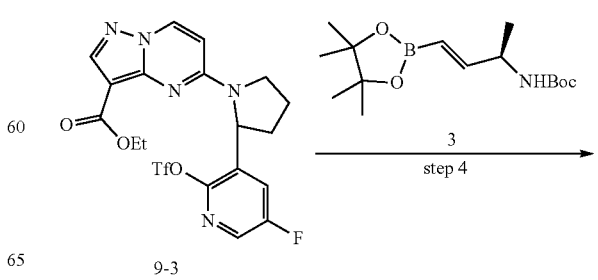

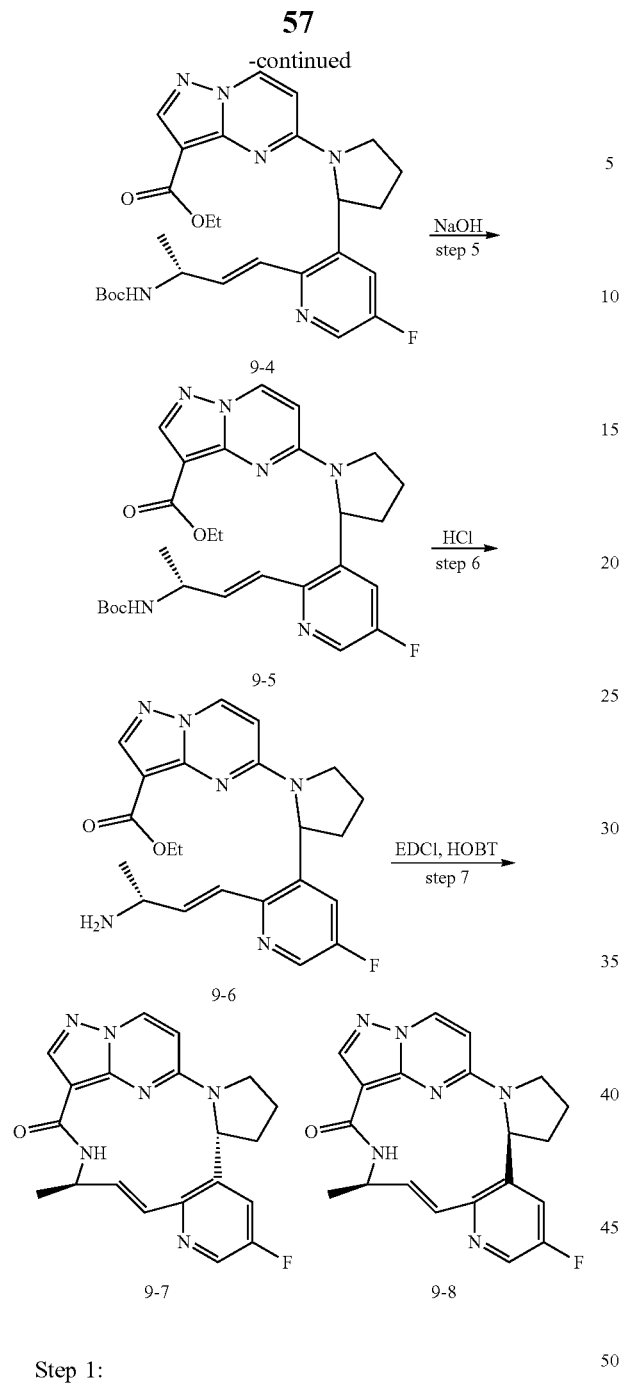

Step 5:

Compound 9-4 was converted to compound 9-5 following similar procedures described in Method 1, step 8. LC-MS: m/e=497 [M+H]⁺.

Step 6:

Compound 9-5 was converted to compound 9-6 following similar procedures described in Method 1, step 3. LC-MS: m/e=397 [M+H]⁺.

Step 7:

Compound 9-6 was converted to compounds 9-7 and 9-8 following similar procedures described in Method 1, step 9. The diastereoisomeric mixture was separated by Prep-HPLC (Column, XBridge Prep OBD C18 Column, 30*150 mm 5 um; mobile phase, Water (0.05% TFA) and ACN (20% Phase B up to 40% in 8 min); Detector, UV). LC-MS for compound 9-7: m/e=379 [M+H]⁺. LC-MS for compound 9-8: m/e=379 [M+H]⁺.

Method 10:

Scheme 10

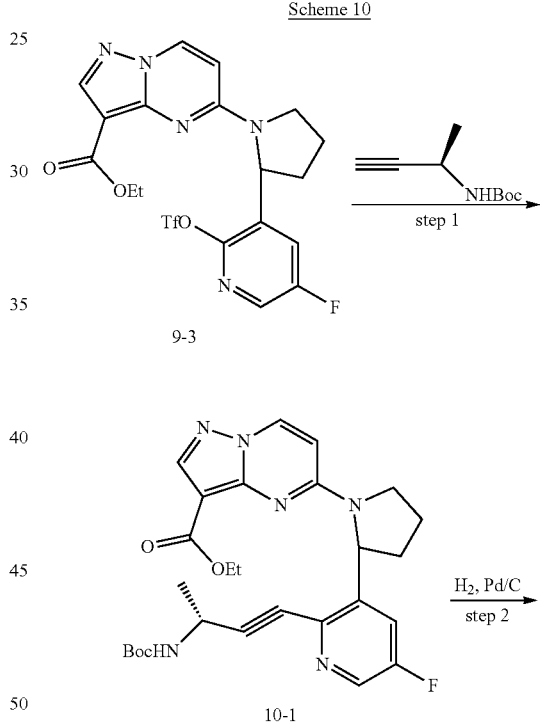

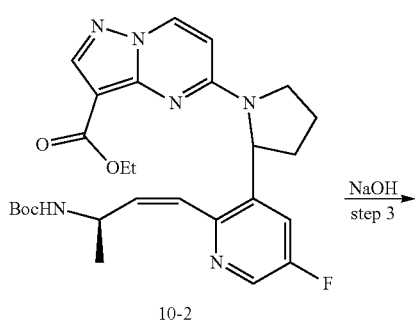

Step 1:

Compound 7-3 was converted to compound 9-1 following similar procedures described in Method 1, step 4. LC-MS: m/e=386 [M+H]⁺.

Step 2:

Compound 9-1 was converted to compound 9-2 following similar procedures described in Method 7, step 5. LC-MS: m/e=372 [M+H]⁺.

Step 3:

Compound 9-2 was converted to compound 9-3 following similar procedures described in Method 7, step 6. LC-MS: m/e=504 [M+H]⁺.

Step 4:

Compound 9-3 was converted to compound 9-4 following similar procedures described in Method 1, step 5. LC-MS: m/e=525 [M+H]⁺.

-continued

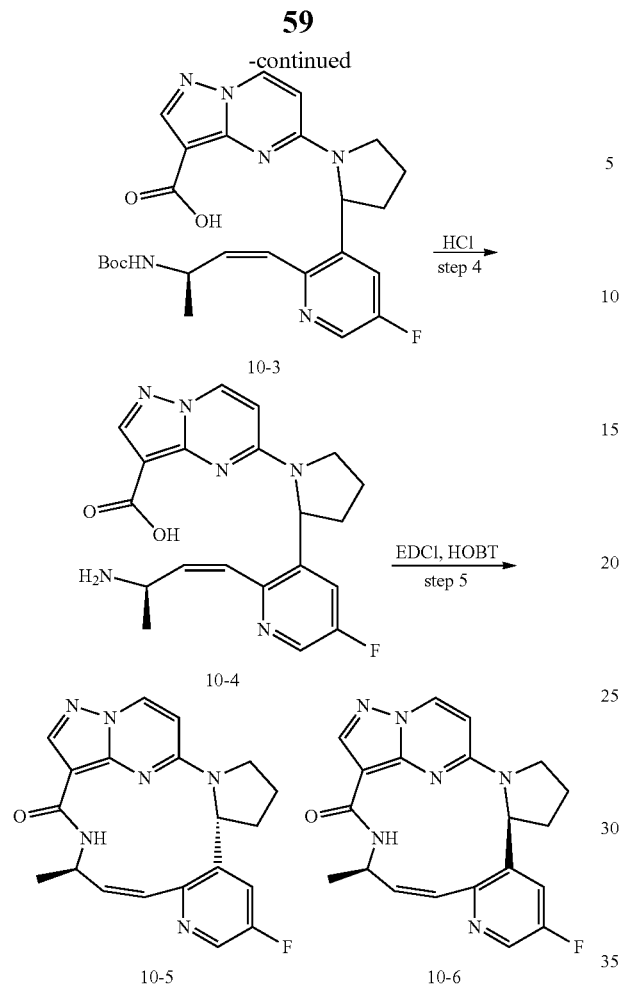

Method 11:

Scheme 11

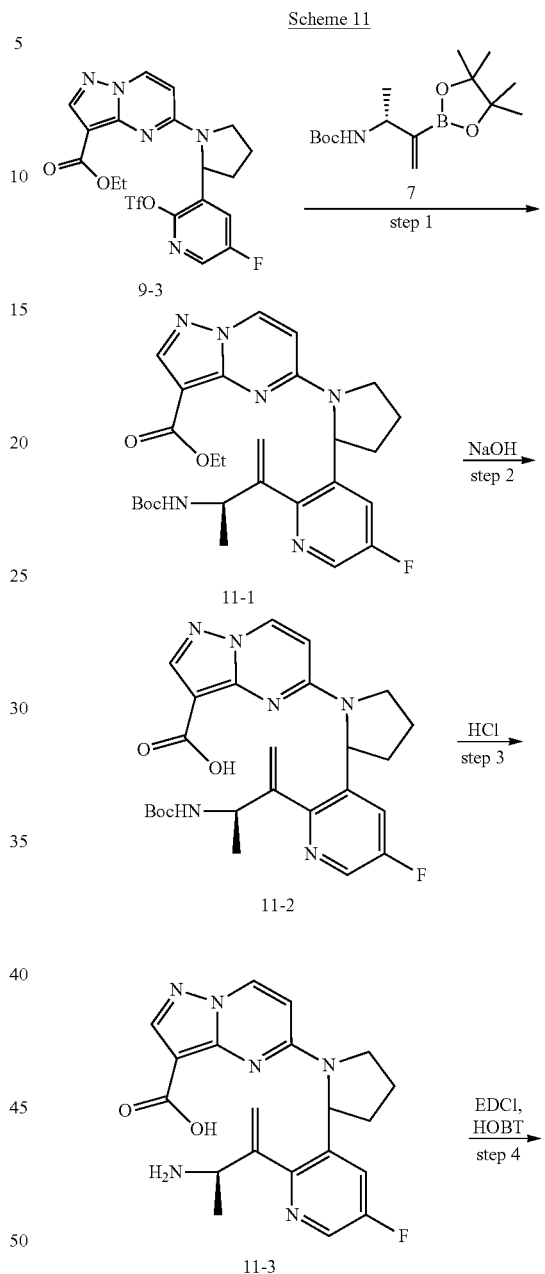

Step 1:
Compound 9-3 was converted to compound 10-1 following similar procedures described in Method 5, step 3. LC-MS: m/e=523 [M+H]⁺.

Step 2:
To a solution of 1.5 g (2.9 mmol) of compound 10-1 in 30 mL of THF was added 1.5 g, 10 wt % Pd/C. The resulting solution was stirred at 10 to 15° C. for 3 h. The mixture was filtered and the filter cake was washed with three 20 mL portions of THF. The combined filtrates were concentrated under reduced pressure to afford crude compound 10-2, which was used in the next step without further purification. LC-MS: m/e=525 [M+H]⁺.

Step 3:
Compound 10-2 was converted to compound 10-3 following similar procedures described in Method 1, step 8. LC-MS: m/e=497 [M+H]⁺.

Step 4:
Compound 10-3 was converted to compound 10-4 following similar procedures described in Method 2, step 3. LC-MS: m/e=397 [M+H]⁺.

Step 5:
Compound 10-4 was converted to compound 10-5 and 10-6 following similar procedures described in Method 1, step 9. The diastereoisomeric mixture was separated by Prep-HPLC (Column, XBridge Prep OBD C18 Column, 30*150 mm 5 um; mobile phase, Water (0.05% TFA) and ACN (20% Phase B, up to 32% in 8 min); Detector, UV). LC-MS for compound 10-5: m/e=379 [M+H]⁺. LC-MS for compound 10-6: m/e=379 [M+H]⁺.

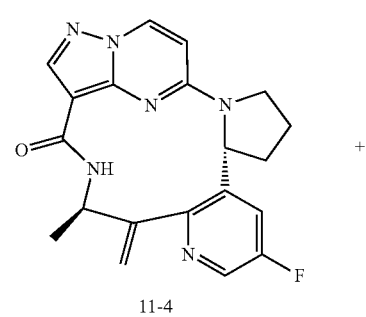

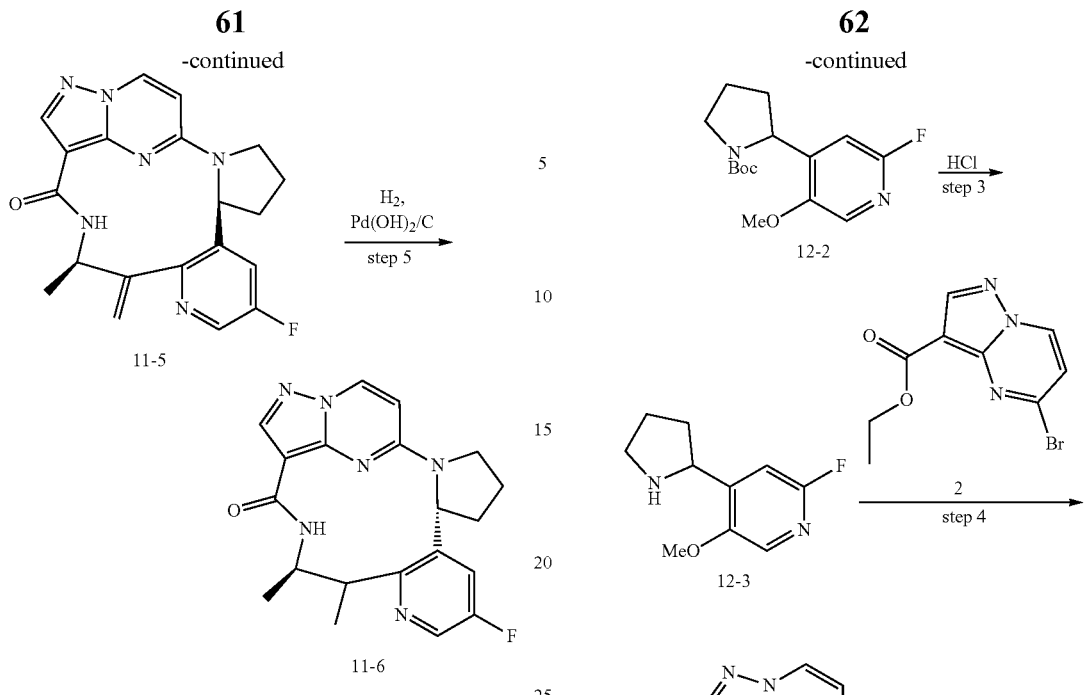

Step 1:
Compound 9-3 was converted to compound 11-1 following similar procedures described in Method 1, step 5, using the boronic ester 7 as the coupling reagent. LC-MS: m/e=525 [M+H]+.

Step 2:
Compound 11-1 was converted to compound 11-2 following similar procedures described in Method 1, step 8. LC-MS: m/e=497 [M+H]+.

Step 3:
Compound 11-2 was converted to compound 11-3 following similar procedures described in Method 2, step 3. LC-MS: m/e=397 [M+H]+.

Step 4:
Compound 11-3 was converted to compound 11-4 and 11-5 following similar procedures described in Method 1, step 9. LC-MS for compound 11-4: m/e=379 [M+H]+. LC-MS for compound 11-5: m/e=379 [M+H]+.

Step 5:
Compound 11-4 was converted to compound 11-6 following similar procedures described in Method 1, step 6. LC-MS: m/e=381 [M+H]+. The configuration of the methyl group is not determined.

Method 12:

Scheme 12

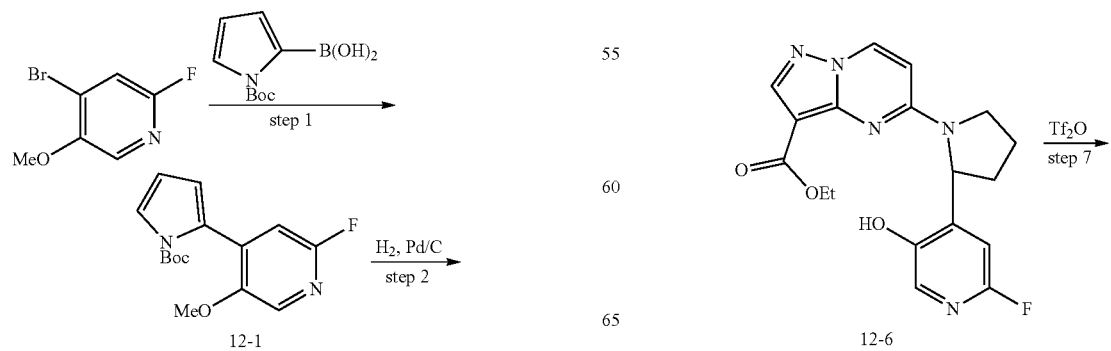

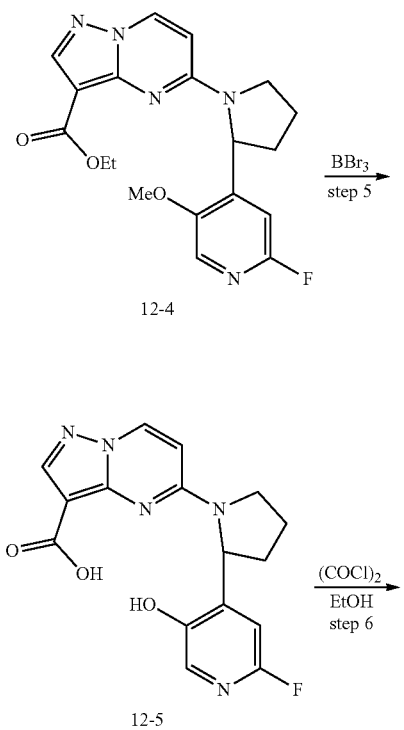

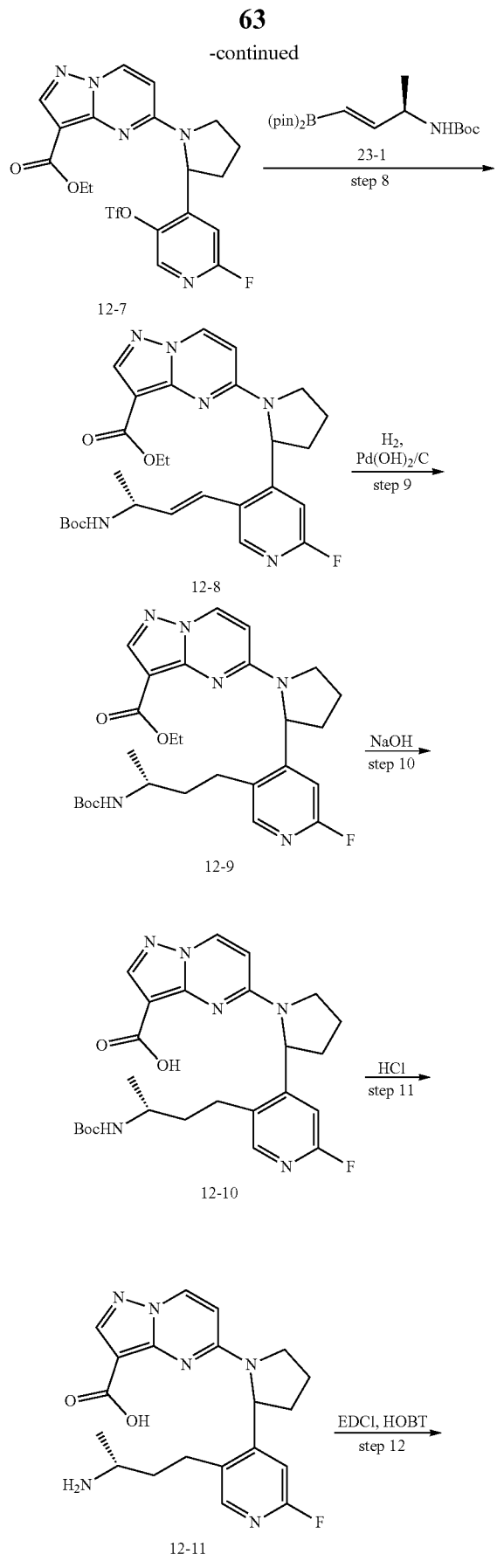
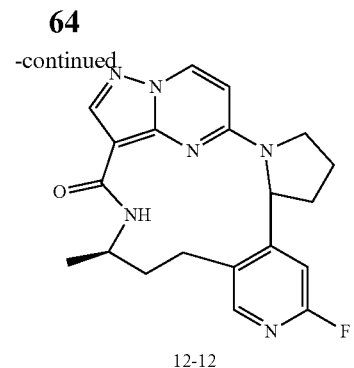

Step 1:
Compound 12-1 was prepared from 4-bromo-2-fluoro-5-methoxypyridine following similar procedures described in Method 7, step 1. LC-MS: m/e=293 [M+H]$^+$.

Step 2:
Compound 12-1 was converted to compound 12-2 following similar procedures described in Method 10, step 2. LC-MS: m/e=297 [M+H]$^+$.

Step 3:
Compound 12-2 was converted to compound 12-3 following similar procedures described in Method 1, step 3. LC-MS: m/e=197 [M+H]$^+$.

Step 4:
Compound 12-3 was converted to compound 12-4 following similar procedures described in Method 1, step 4. LC-MS: m/e=386 [M+H]$^+$.

Step 5:
To a stirred solution of 440 mg (1.14 mmol) of compound 12-4 in 2 mL of DME, was added 2.0 mL (21 mmol) of BBr$_3$ dropwise at 0° C. The mixture was stirred at 60° C. overnight. The reaction was quenched with MeOH at 0° C., concentrated under reduced pressure to afford a residue, which was purified by reverse phase flash chromatography (Kinextex XB-C18 (50*3.0 mm) 2.6 µm; A: 0.1% Formic acid in Water, B: Acetonitrile, 10% to 30% gradient in 30 mins; detector, UV 254 nm) to afford compound 12-5. LC-MS: m/e=344 [M+H]$^+$.

Step 6:
To a stirred solution of 190 mg (0.55 mmol) of compound 12-5 in 3 mL of DCM was added 3 mL of oxalyl chloride and 0.01 mL of DMF was stirred for 3 h at rt under nitrogen atmosphere. The mixture was concentrated under reduced pressure. To the above mixture was added 2 mL of EtOH dropwise at 0° C. The resulting mixture was concentrated under reduced pressure to afford a crude, which was purified by Prep-TLC eluting with 6% MeOH in DCM to afford compound 12-6. LC-MS: m/e=372 [M+H]$^+$.

Step 7:
Compound 12-6 was converted to compound 12-7 following similar procedures described in Method 6, step 5. LC-MS: m/e=504 [M+H]$^+$.

Step 8:
Compound 12-7 was converted to compound 12-8 following similar procedures described in Method 1, step 5. LC-MS: m/e=525 [M+H]$^+$.

Step 9:
Compound 12-8 was converted to compound 12-9 following similar procedures described in Method 1, step 6. LC-MS: m/e=527 [M+H]$^+$.

Step 10:
Compound 12-9 was converted to compound 12-10 following similar procedures described in Method 1, step 8. LC-MS: m/e=499 [M+H]$^+$.

Step 11:
Compound 12-10 was converted to compound 12-11 following similar procedures described in Method 1, step 3. LC-MS: m/e=399 [M+H]+.
Step 12:
Compound 12-11 was converted to compound 12-12 as a mixture of two diastereoisomers without further separation, following similar procedures described in Method 1, step 9. LC-MS: m/e=381 [M+H]+.
Method 13:
Scheme 13
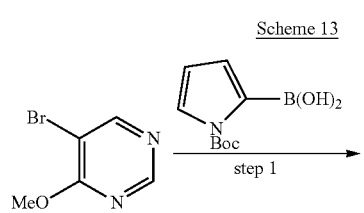
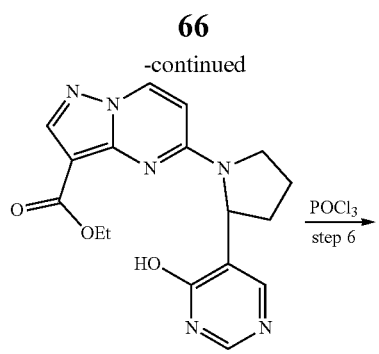
13-5
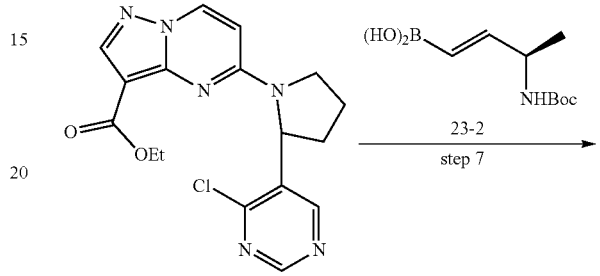
13-6
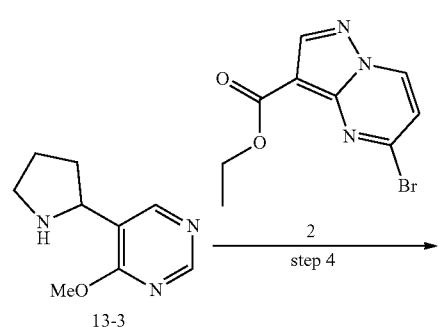
13-1
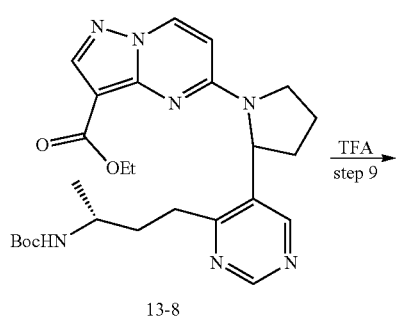
13-7
13-2
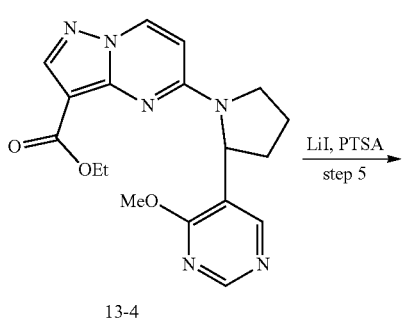
13-3
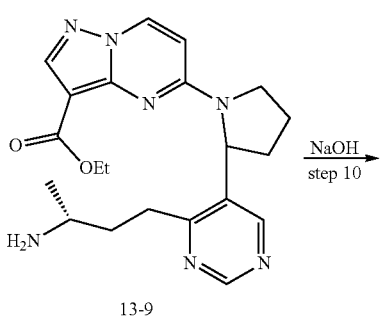
13-8
13-4
13-9

-continued

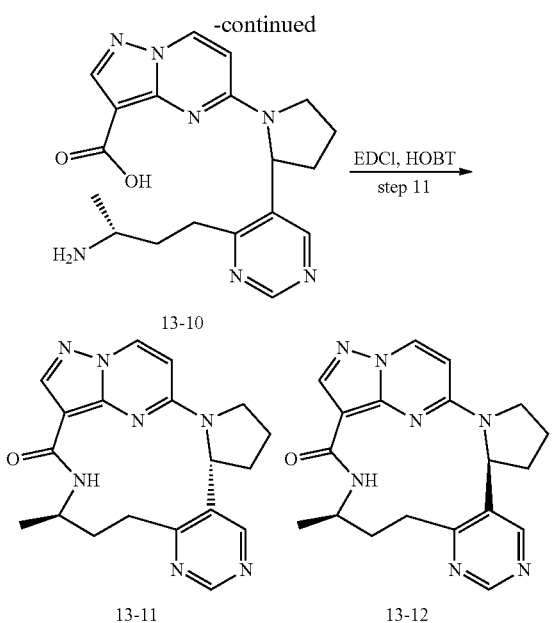

Step 1:
Compound 13-1 was prepared from 5-bromo-4-methoxy-pyrimidine following similar procedures described in Method 7, step 1. LC-MS: m/e=276 [M+H]⁺.

Step 2:
Compound 13-1 was converted to compound 13-2 following similar procedures described in Method 7, step 2. LC-MS: m/e=280 [M+H]⁺.

Step 3:
Compound 13-2 was converted to compound 13-3 following similar procedures described in Method 1, step 3. LC-MS: m/e=180[M+H]⁺.

Step 4:
Compound 13-3 was converted to compound 13-4 following similar procedures described in Method 1, step 4. LC-MS: m/e=369 [M+H]⁺.

Step 5:
To a stirred solution of 0.75 g (2.0 mmol) of compound 13-4 in 6 mL of DMF was added 1.36 g (10.2 mmol) of LiI and 1.75 g (10.2 mmol) of PTSA. The mixture was stirred at 120° C. for 1 h and cooled to rt. It was concentrated to give a residue, which was purified by reverse phase flash chromatography under the following conditions: column, C18 silica gel; mobile phase A: 0.05% formic acid in Water, B: Acetonitrile, 5% to 40% gradient in 30 mins; detector, UV 254 nm to afford compound 13-5. LC-MS: m/e=355 [M+H]⁺.

Step 6:
To a stirred solution of 0.29 g (0.82 mmol) of compound 13-5 in 6 mL of toluene were added 0.38 g (2.5 mmol) of POCl₃ and 0.26 g (2.1 mmol) of DIEA. The mixture was stirred at 70° C. for 1 h and cooled to rt. It was concentrated to afford a residue, which was purified by silica gel column chromatography eluting with 0 to 5% gradient of DCM in MeOH to afford compound 13-6. LC-MS: m/e=373 [M+H]⁺.

Step 7:
Compound 13-6 was converted to compound 13-7 following similar procedures described in Method 6, step 6. LC-MS: m/e=508 [M+H]⁺.

Step 8:
Compound 13-7 was converted to compound 13-8 following similar procedures described in Method 1, step 6. LC-MS: m/e=510 [M+H]⁺.

Step 9:
Compound 13-8 was converted to compound 13-9 following similar procedures described in Method 1, step 7. LC-MS: m/e=410 [M+H]⁺.

Step 10:
Compound 13-9 was converted to compound 13-10 following similar procedures described in Method 1, step 8. LC-MS: m/e=382 [M+H]⁺.

Step 11:
Compound 13-10 was converted to compound 13-11 following similar procedures described in Method 1, step 9. LC-MS for compound 13-11: m/e=364 [M+H]⁺. LC-MS for compound 13-12: m/e=364 [M+H]⁺.

Method 14:

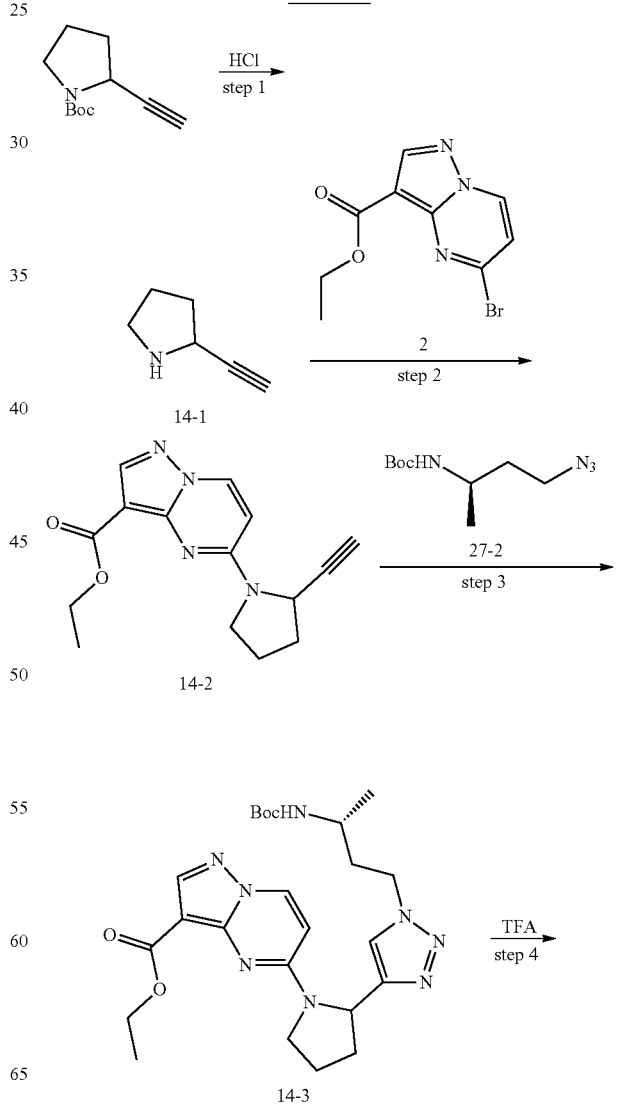

Scheme 14

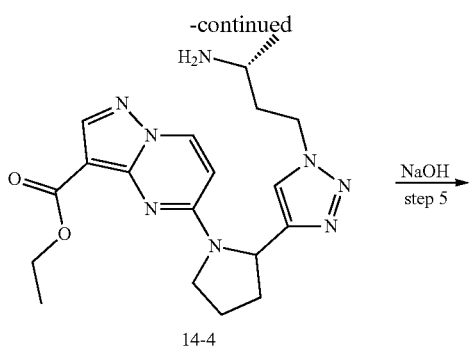

14-4

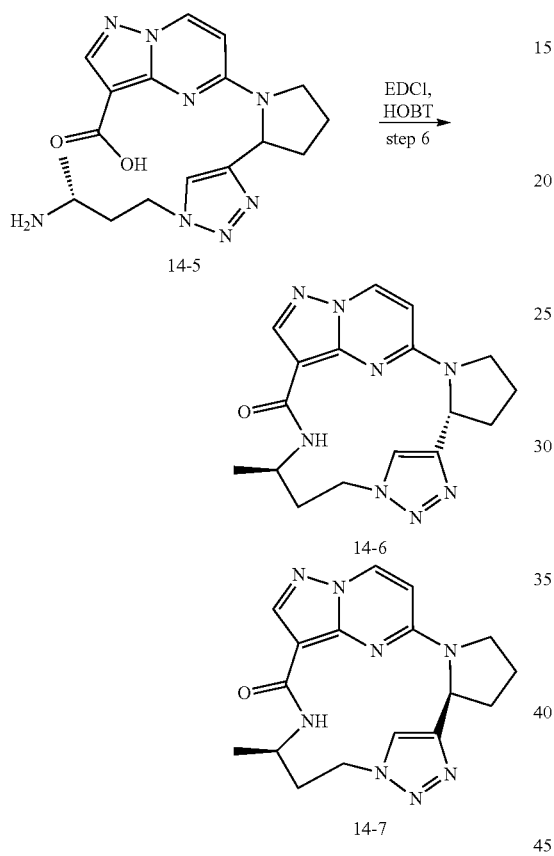

14-5

14-6

14-7

Step 1:

Compound 14-1 was prepared from tert-butyl 2-ethynylpyrrolidine-1-carboxylate following similar procedures described in Method 1, step 3. It was used in the next step directly without further purification.

Step 2:

Compound 14-1 was converted to compound 14-2 following similar procedures described in Method 1, step 4. LC-MS: m/e=285 [M+H]$^+$.

Step 3:

To a stirred solution of 300 mg (1.1 mmol) of compound 14-2 in 5 mL of t-BuOH and 0.5 mL of H$_2$O were added 271.3 mg (1.300 mmol) of compound 27-2, 5.3 mg (0.020 mmol) of CuSO$_4$·5H$_2$O, 21 mg (0.11 mmol) of sodium ascorbate at rt. The mixture was stirred at 30° C. overnight. The mixture was diluted with 50 mL of water, extracted with three 50 mL portions of ethyl acetate. The combined organic layers were washed with 50 mL of brine, dried over anhydrous Na$_2$SO$_4$. After filtration, the filtrate was concentrated under reduced pressure to afford a residue, which was purified by silica gel column chromatography eluting with 2% MeOH in DCM to afford compound 14-3. LC-MS: m/e=499 [M+H]$^+$.

Step 4:

Compound 14-3 was converted to compound 14-4 following similar procedures described in Method 1, step 7. LC-MS: m/e=399 [M+H]$^+$.

Step 5:

Compound 14-4 was converted to compound 14-5 following similar procedures described in Method 1, step 8. LC-MS: m/e=371 [M+H]$^+$.

Step 6:

Compound 14-5 was converted to compounds 14-6 and 14-7 following similar procedures described in Method 1, step 9. LC-MS for compound 14-6: m/e=353 [M+H]$^+$. LC-MS for compound 14-7: m/e=353 [M+H]$^+$.

Method 15:

Scheme 15

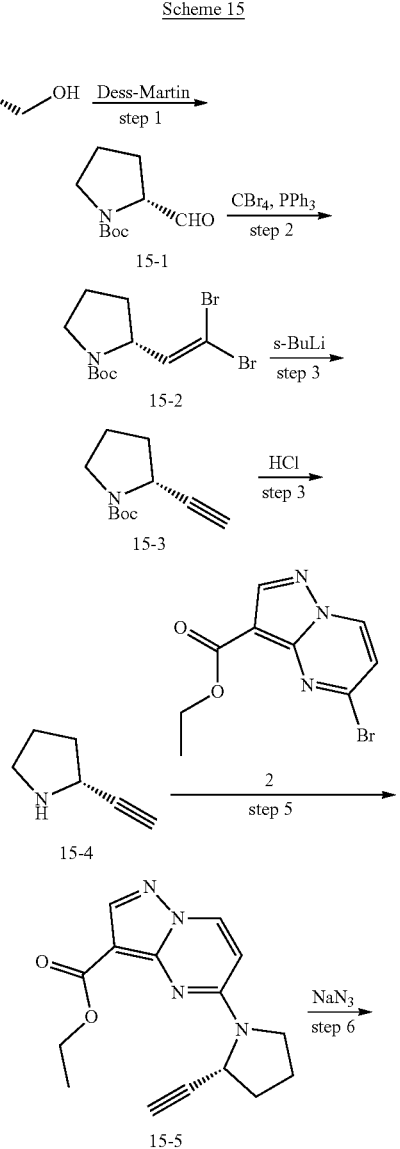

15-1

15-2

15-3

15-4

15-5

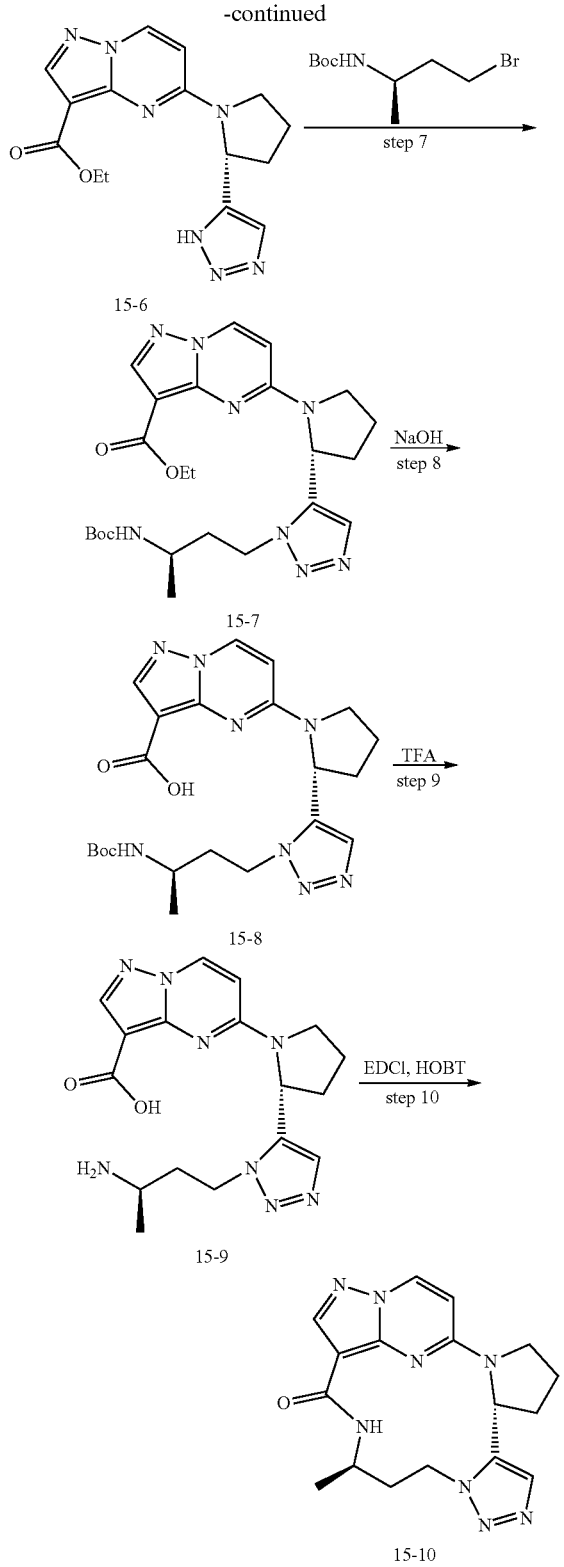

NaHCO$_3$ solution and 50 mL of Na$_2$S$_2$O$_3$ solution. It was extracted with three 100 mL portions of ethyl acetate; the combined organic extracts were washed 100 mL with brine, dried over anhydrous Na$_2$SO$_4$. After filtration, the filtrate was concentrated to afford a residue, which was purified by chromatography on silica gel column eluting with 0 to 20% gradient of DCM in MeOH to afford compound 15-1.

Step 2:

To a stirred solution of 2.90 g (11.1 mmol) of PPh$_3$ and 1.66 g (5.00 mmol) of CBr$_4$ in 40 mL of CH$_2$Cl$_2$ was added 0.50 g (2.5 mmol) of compound 15-1 in CH$_2$Cl$_2$ 5 mL dropwise at rt. The mixture was stirred at rt for 1 h and quenched by addition of 50 mL of saturated NaHCO$_3$ solution. It was extracted with three 100 mL portions of CH$_2$Cl$_2$. The combined organic layers dried over anhydrous Na$_2$SO$_4$. After filtration, the filtrate was concentrated to give a residue, which was purified by silica gel column chromatography eluting with 0 to 5% gradient of MeOH in CH$_2$Cl$_2$ to afford compound 15-2.

Step 3:

To a stirred solution of 800 mg (2.3 mmol) of compound 15-2 in 20 mL of THF was added 3.49 mL (1.3 M in hexane) of s-BuLi dropwise at −78° C. under nitrogen atmosphere. The mixture was stirred at −78° C. for 1 h and quenched with saturated NH$_4$Cl solution. It was extracted with three 30 mL portions of ethyl acetate; the combined organic layers were washed with 20 mL of brine, dried over anhydrous Na$_2$SO$_4$. After filtration, the filtrate was concentrated to give a residue, which was purified by silica gel column chromatography eluting with 0 to 20% gradient of ethyl acetate in petroleum ether to afford compound 15-3.

Step 4:

Compound 15-3 was converted to compound 15-4 following similar procedures described in Method 1, step 3.

Step 5:

Compound 15-4 was converted to compound 15-5 following similar procedures described in Method 1, step 4. LC-MS: m/e=285 [M+H]$^+$.

Step 6:

To a solution of 10 mL of DMF-MeOH (10:1) was added 500 mg (1.8 mmol) of compound 15-5, 306 mg (2.70 mmol) of azidotrimethylsilane and 34 mg (0.18 mmol) of CuI at rt. The mixture was irradiated with microwave at 100° C. for 1 h and cooled to rt. It was concentrated under reduced pressure to afford a residue, which was purified by reverse phase flash chromatography under the following conditions: column, C18 silica gel, mobile phase, A: 0.05% formic acid in Water, B: Acetonitrile, 0% to 20% gradient in 30 mins; detector, UV 254 nm to afford compound 15-6. LC-MS: m/e=328 [M+H]$^+$.

Step 7:

To a stirred mixture of 280 mg (0.86 mmol) of compound 15-6 in 14 mL of DMF were added 323.5 mg (1.28 mmol) of tert-butyl N-[(2R)-4-bromobutan-2-yl]carbamate compound and 355 mg (2.57 mmol) of K$_2$CO$_3$. The mixture was stirred at rt for 1 h and concentrated under reduced pressure to afford a residue, which was purified by reverse phase flash chromatography (column, C18 silica gel, mobile phase, A: 0.05% formic acid in Water, B: Acetonitrile, 0 to 40% gradient in 30 mins; detector, UV 254 nm) to afford compound 15-7. LC-MS: m/e=499 [M+H]$^+$.

Step 8:

Compound 15-7 was converted to compound 15-8 following similar procedures described in Method 1, step 8. LC-MS: m/e=471 [M+H]$^+$.

Step 1:

To a stirred solution of 5.0 g (25 mmol) of tert-butyl (R)-2-(hydroxymethyl)pyrrolidine-1-carboxylate in 200 mL of DCM was added 15.8 g (37.3 mmol) of Dess-Martin periodinane in portions at 0° C. The mixture was stirred at rt for 2 h and quenched by addition of 50 mL of saturated Step 9:
Compound 15-8 was converted to compound 15-9 following similar procedures described in Method 1, step 7. LC-MS: m/e=371 [M+H]+.

Step 10:
Compound 15-9 was converted to compound 15-10 following similar procedures described in Method 1, step 9. LC-MS: m/e=353 [M+H]+.

Method 16:

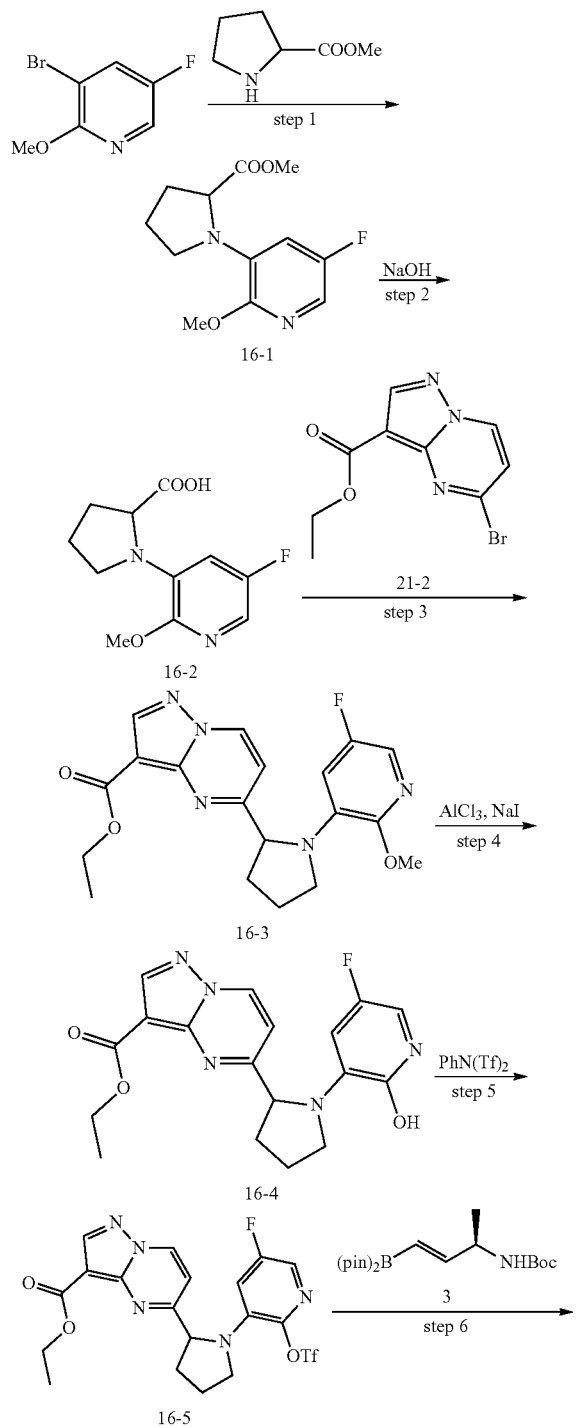

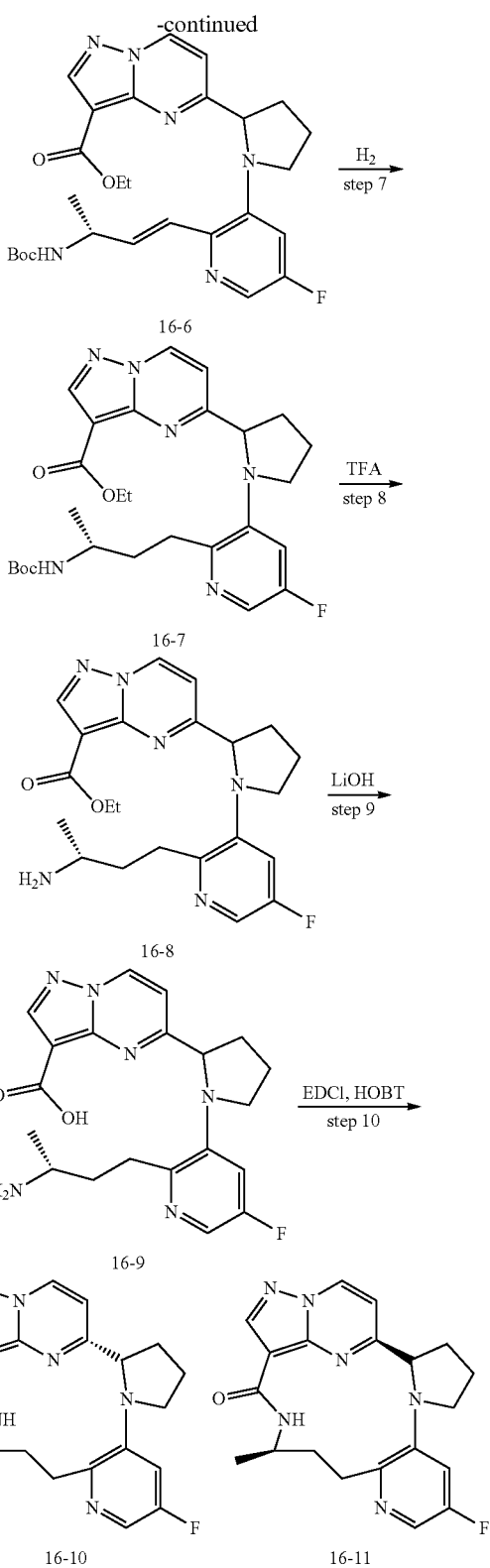

Step 1:
To a solution of 5.0 g (24 mmol) 3-bromo-5-fluoro-2-methoxypyridine in 200 mL of toluene were added 5.2 g (31 mmol) of methyl pyrrolidine-2-carboxylate hydrochloride, 3.0 g (4.9 mmol) of BINAP, 31.6 g (97.0 mmol) of $Cs_2CO_3$ and 2.5 g (2.4 mmol) of $Pd_2(dba)_3 \cdot CHCl_3$. The mixture was stirred at 90° C. overnight under nitrogen atmosphere. It was diluted with 200 mL of ethyl acetate, washed with three 50 mL portions of water, and dried over anhydrous Na$_2$SO$_4$. After filtration, the filtrate was concentrated under reduced pressure to afford a residue, which was purified by chromatography on silica gel column eluting with 18% of ethyl acetate in petroleum ether to afford compound 16-1. LC-MS: m/e=255 [M+H]$^+$.

Step 2:

Compound 16-1 was converted to compound 16-2 following similar procedures described in Method 1, step 8. LC-MS: m/e=241 [M+H]$^+$.

Step 3:

To a solution of 0.58 g (2.4 mmol) of compound 16-2 in 80 mL of DMF were added 0.54 g (2.0 mmol) of ethyl 5-bromopyrazolo[1,5-a]pyrimidine-3-carboxylate, 0.24 g (0.9 mmol) dtbbpy, 2.0 g (6.0 mmol) of Cs$_2$CO$_3$, 0.055 g (0.050 mmol) of [Ir(dF-CF$_3$-ppy)]$_2$(dtbbpy)PF$_6$ and 0.055 g (0.25 mmol) of NiCl$_2$.glyme. The mixture was degassed by bubbling nitrogen stream for 20 min, then irradiated with a 40 W blue LED at 25° C. overnight. It was diluted with 300 mL of saturated NaHCO$_3$ solution, extracted with two 100 mL portions of ethyl acetate. The combined organic extracts were washed with 100 mL of brine, dried over anhydrous Na$_2$SO$_4$. After filtration, the filtrate was concentrated under reduced pressure to afford a residue, which was purified by chromatography on silica gel column eluting with 25% of ethyl acetate in petroleum ether to afford compound 16-3. LC-MS: m/e=386 [M+H]$^+$.

Step 4:

Compound 16-3 was converted to compound 16-4 following similar procedures described in Method 2, step 5. LC-MS: m/e=372 [M+H]$^+$.

Step 5:

Compound 16-4 was converted to compound 16-5 following similar procedures described in Method 7, step 6. LC-MS: m/e=504 [M+H]$^+$.

Step 6:

Compound 16-5 was converted to compound 16-6 following similar procedures described in Method 1, step 5. LC-MS: m/e=525 [M+H]$^+$.

Step 7:

To a solution of 0.39 g (0.74 mmol) of compound 16-6 in 10 mL of ethyl acetate was added 0.20 g of 50 wt % of Rh/C. The mixture was stirred at rt for 24 h under hydrogen atmosphere. The mixture was filtered and the filter cake was washed with three 20 mL portions of ethyl acetate. The combined filtrates were concentrated under reduced pressure to afford crude compound 16-7. LC-MS: m/e=527 [M+H]$^+$.

Step 8:

Compound 16-7 was converted to compound 16-8 following similar procedures described in Method 1, step 7. LC-MS: m/e=427 [M+H]$^+$.

Step 9:

To a solution of 0.20 g (0.47 mmol) of compound 16-8 TFA salt in 2 mL of THF and 1 mL of H$_2$O was added 0.056 g (2.4 mmol) of LiOH. The resulting mixture was stirred at 30° C. overnight. The mixture was acidified to pH6 with 2 N HCl. The mixture was concentrated under reduced pressure to afford a residue, which was purified by reverse phase flash chromatography (column, C18 silica gel, mobile phase, A: 0.05% Formic acid in Water, B: Acetonitrile, 5% to 16% gradient in 30 mins; detector, UV 254 nm) to afford compound 16-9. LC-MS: m/e=399 [M+H]$^+$.

Step 10:

Compound 16-9 was converted to compound 16-10 and 16-11 following similar procedures described in Method 1, step 9. LC-MS for compound 16-10: m/e=381 [M+H]$^+$. LC-MS for compound 16-11: m/e=381 [M+H]$^+$. The configurations at the pyrrolidine ring are arbitrarily assigned.

Method 17:

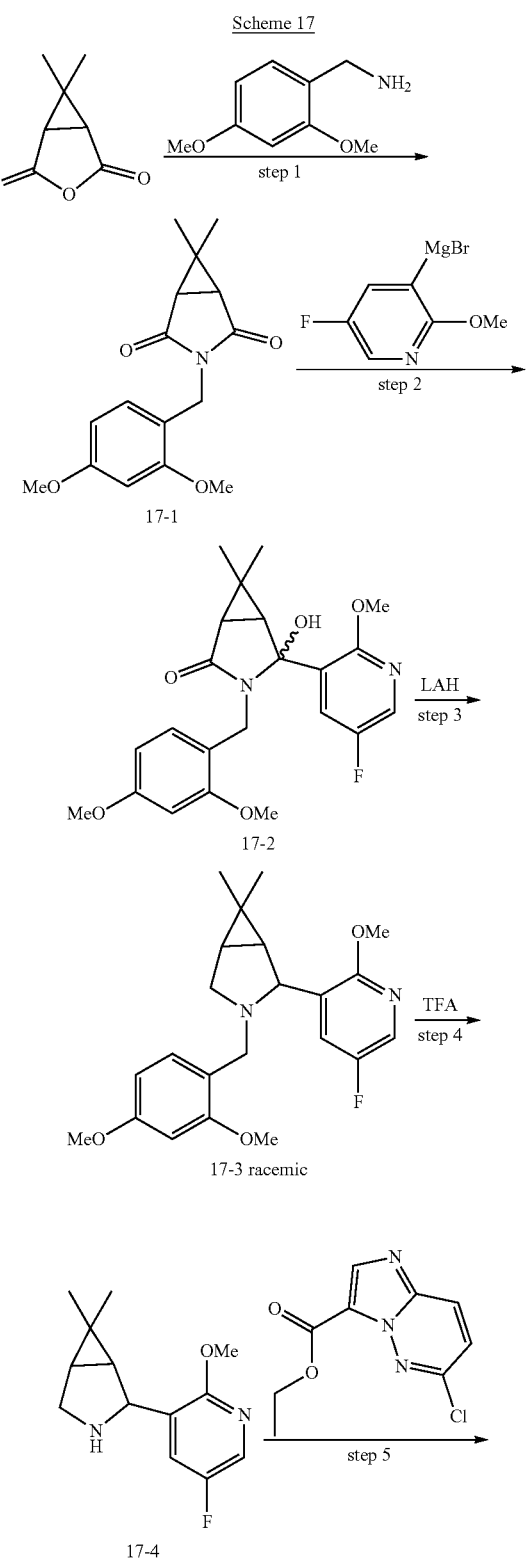

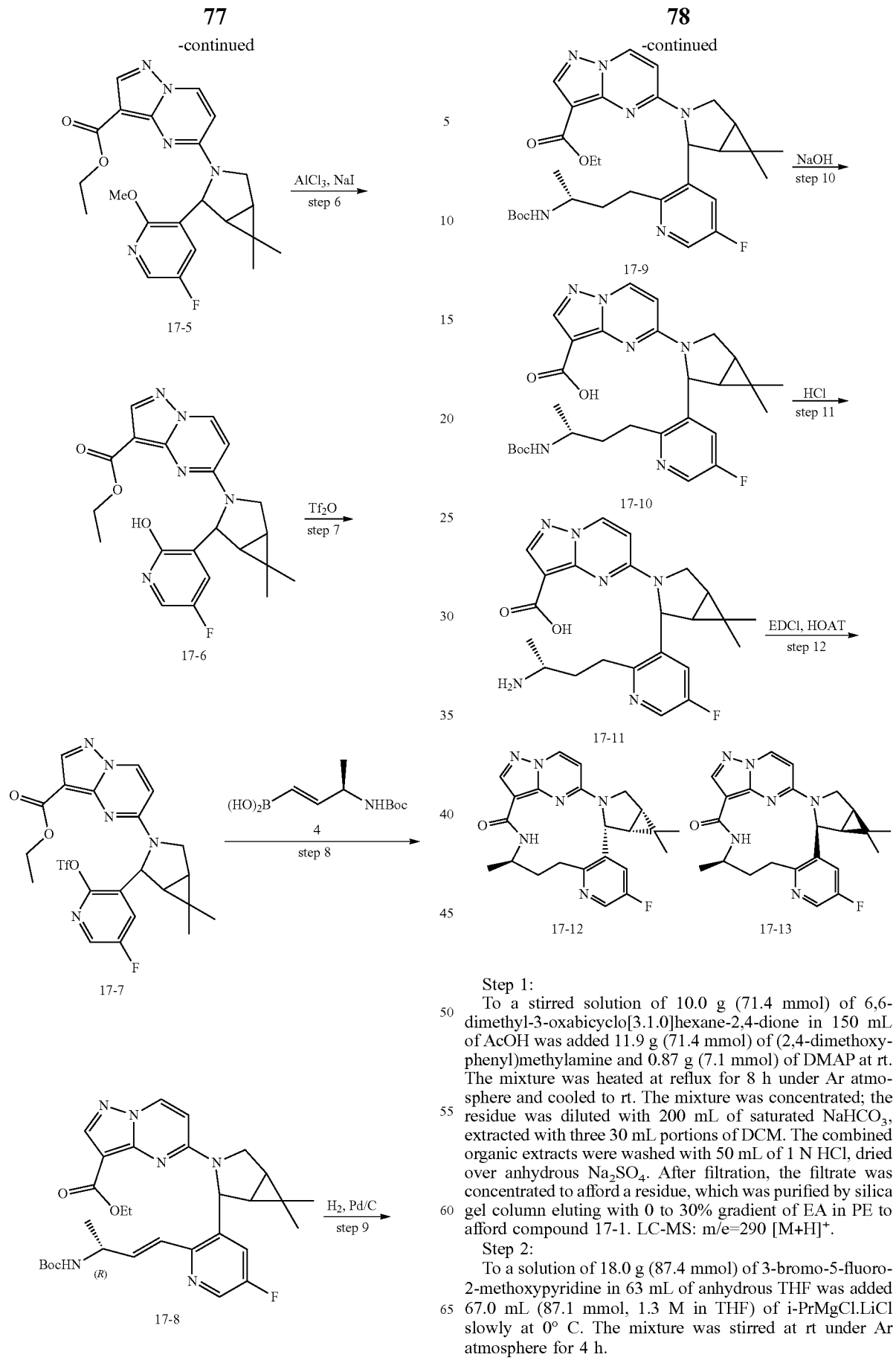

Step 1:
To a stirred solution of 10.0 g (71.4 mmol) of 6,6-dimethyl-3-oxabicyclo[3.1.0]hexane-2,4-dione in 150 mL of AcOH was added 11.9 g (71.4 mmol) of (2,4-dimethoxyphenyl)methylamine and 0.87 g (7.1 mmol) of DMAP at rt. The mixture was heated at reflux for 8 h under Ar atmosphere and cooled to rt. The mixture was concentrated; the residue was diluted with 200 mL of saturated NaHCO$_3$, extracted with three 30 mL portions of DCM. The combined organic extracts were washed with 50 mL of 1 N HCl, dried over anhydrous Na$_2$SO$_4$. After filtration, the filtrate was concentrated to afford a residue, which was purified by silica gel column eluting with 0 to 30% gradient of EA in PE to afford compound 17-1. LC-MS: m/e=290 [M+H]$^+$.

Step 2:
To a solution of 18.0 g (87.4 mmol) of 3-bromo-5-fluoro-2-methoxypyridine in 63 mL of anhydrous THF was added 67.0 mL (87.1 mmol, 1.3 M in THF) of i-PrMgCl.LiCl slowly at 0° C. The mixture was stirred at rt under Ar atmosphere for 4 h.

To a stirred solution of 12.6 g (43.6 mmol) of compound 17-1 in 10 mL of DCM was added 130 mL of the above Grignard reagent (~0.4 M in THF) at −78° C. The mixture was stirred at rt under Ar atmosphere overnight, then quenched by addition of 200 mL of saturated NH₄Cl at 0° C. The organic phase was separated, dried over anhydrous Na₂SO₄. After filtration, the filtrate was concentrated to afford a residue, which was purified by C₁₈ column eluting with 0 to 30% gradient of ACN in H₂O (0.5% NH₄HCO₃) to afford compound 17-2. LC-MS: m/e=417 [M+H]⁺.

Step 3:

To a solution of 2.0 g (4.8 mmol) of compound 17-2 in 120 mL of anhydrous THF was added 12 mL (12 mmol, 1 M in THF) of LAH at rt. The mixture was heated at reflux for 3 h, cooled to 0° C., and quenched by addition of 50 mL of saturated NH₄Cl. The organic phase was separated, dried over anhydrous Na₂SO₄. After filtration, the filtrate was concentrated to afford a residue, which was purified by C₁₈ column eluting with 0 to 80% gradient of ACN in H₂O (0.5% NH₄HCO₃) to afford compound 17-3. LC-MS: m/e=387 [M+H]⁺.

Step 4:

A solution of 550 mg (1.4 mmol) of compound 17-3 in 30 mL of TFA was heated at reflux for 5 h under Ar atmosphere, and then concentrated under vacuum to give crude compound 17-4 as TFA salt, which was used in the next step without further purification. LC-MS: m/e=237 [M+H]⁺.

Step 5:

Compound 17-4 was converted to compound 17-5 following similar procedures described in Method 7, step 4. LC-MS: m/e=426 [M+H]⁺.

Step 6:

Compound 17-5 was converted to compound 17-6 following similar procedures described in Method 2, step 5. LC-MS: m/e=412 [M+H]⁺.

Step 7:

Compound 17-6 was converted to compound 17-7 following similar procedures described in Method 6, step 5. LC-MS: m/e=544 [M+H]⁺.

Step 8:

Compound 17-7 was converted to compound 17-8 following similar procedures described in Method 6, step 6. LC-MS: m/e=565 [M+H]⁺.

Step 9:

Compound 17-8 was converted to compound 17-9 following similar procedures described in Method 7, step 2. LC-MS: m/e=567 [M+H]⁺.

Step 10:

Compound 17-9 was converted to compound 17-10 following similar procedures described in Method 1, step 8. LC-MS: m/e=539 [M+H]⁺.

Step 11:

Compound 17-10 was converted to compound 17-11 following similar procedures described in Method 1, step 3. LC-MS: m/e=439 [M+H]⁺.

Step 12:

Compound 17-11 was converted to compound 17-12 and 17-13 following similar procedures described in Method 1, step 9, using HOAT instead of HOBT. LC-MS for compound 17-12: m/e=421 [M+H]⁺. LC-MS for compound 17-13: m/e=421 [M+H]⁺.

Method 18:

Scheme 18

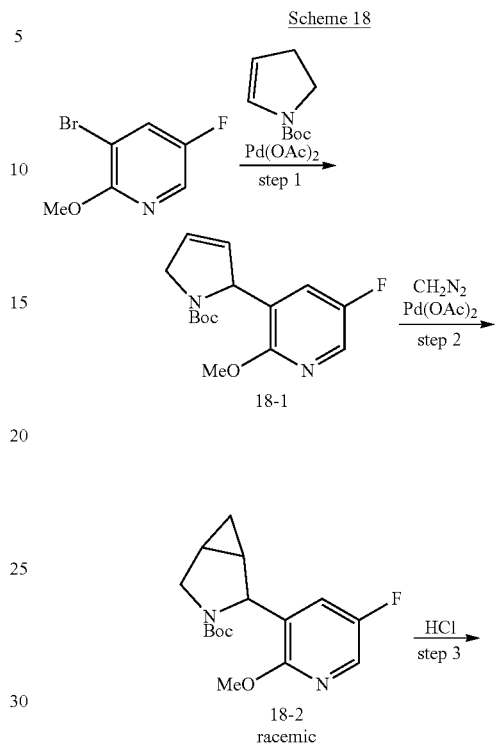

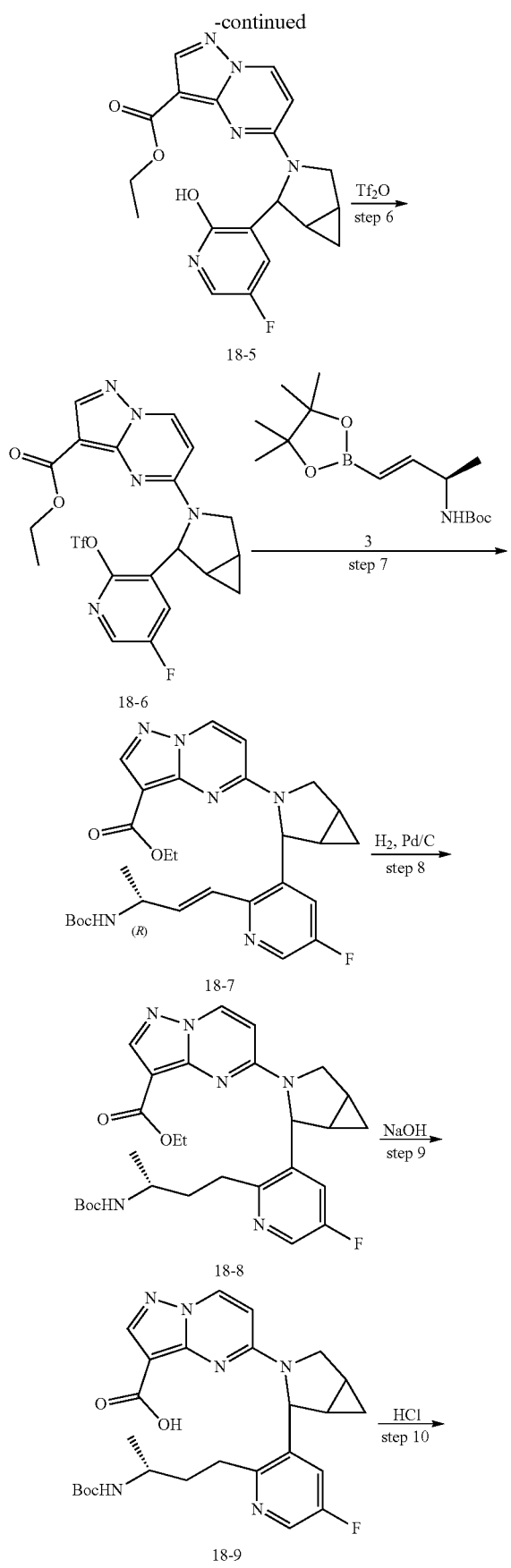

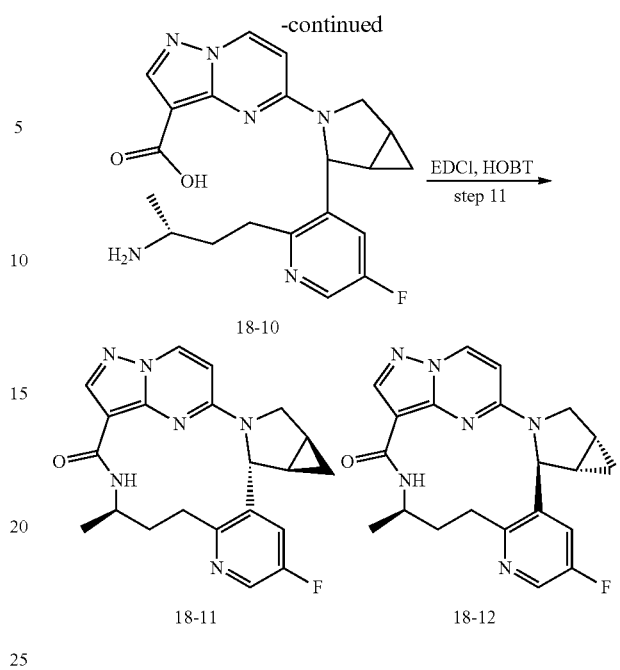

Step 1:

To a solution of 15.0 g (72.8 mmol) of 3-bromo-5-fluoro-2-methoxypyridine in 300 mL of dioxane were added 17.2 g (102 mmol) of tert-butyl 2,3-dihydro-1H-pyrrole-1-carboxylate, 3.80 g (14.5 mmol) of PPh$_3$, 30.30 g (219.2 mmol) of K$_2$CO$_3$ and 1.6 g (7.3 mmol) of Pd(OAc)$_2$. The solution was stirred at 100° C. overnight under nitrogen atmosphere and cooled down to rt. The mixture was diluted with 1000 mL of water, extracted with three 300 mL portions of ethyl acetate. The combined organic layers were washed with 300 mL of brine, dried over anhydrous Na$_2$SO$_4$. After filtration, the filtrate was concentrated under reduced pressure to afford a residue, which was purified by silica gel column chromatography eluting with 6% ethyl acetate in petroleum ether to afford compound 18-1. LC-MS: m/e=295 [M+H]$^+$.

Step 2:

To a stirred solution of 400 mg (1.4 mmol) of compound 18-1 in 20 mL of ether was added 30.5 mg (0.14 mmol) of Pd(OAc)$_2$ and 85 mL (0.2 M in ether) of freshly prepared diazomethane dropwise at 0° C. The mixture was stirred at rt for 1 h, then filtered; the filter cake was washed with two 50 mL portions of ether. The filtrate was concentrated under reduced pressure to afford a residue, which was purified by reverse phase flash chromatography under the following conditions: column, C18 silica gel; mobile phase, A: 0.05% formic acid in water, B: ACN, 5% to 70% gradient in 30 min; detector, UV 220 nm to compound 18-2. LC-MS: m/e=309 [M+H]$^+$.

Step 3:

Compound 18-2 was converted to compound 18-3 following similar procedures described in Method 1, step 3. LC-MS: m/e=209 [M+H]$^+$.

Step 4:

Compound 18-3 was converted to compound 18-4 following similar procedures described in Method 1, step 4. LC-MS: m/e=398 [M+H]$^+$.

Step 5:

Compound 18-4 was converted to compound 18-5 following similar procedures described in Method 7, step 5. LC-MS: m/e=384 [M+H]$^+$.

Step 6:

Compound 18-5 was converted to compound 18-6 following similar procedures described in Method 6, step 5. LC-MS: m/e=516 [M+H]+.

Step 7:

Compound 18-6 was converted to compound 18-7 following similar procedures described in Method 1, step 5. LC-MS: m/e=537 [M+H]+.

Step 8:

Compound 18-7 was converted to compound 18-8 following similar procedures described in Method 7, step 2. LC-MS: m/e=539 [M+H]+.

Step 9:

Compound 18-8 was converted to compound 18-9 following similar procedures described in Method 1, step 8. LC-MS: m/e=511 [M+H]+.

Step 10:

Compound 18-9 was converted to compound 18-10 following similar procedures described in Method 1, step 3. LC-MS: m/e=411 [M+H]+.

Step 11:

Compound 18-10 was converted to compound 18-11 and 18-12 following similar procedures described in Method 1, step 9. LC-MS for compound 18-11: m/e=393 [M+H]+. LC-MS for compound 18-12: m/e=393 [M+H]+.

Method 19:

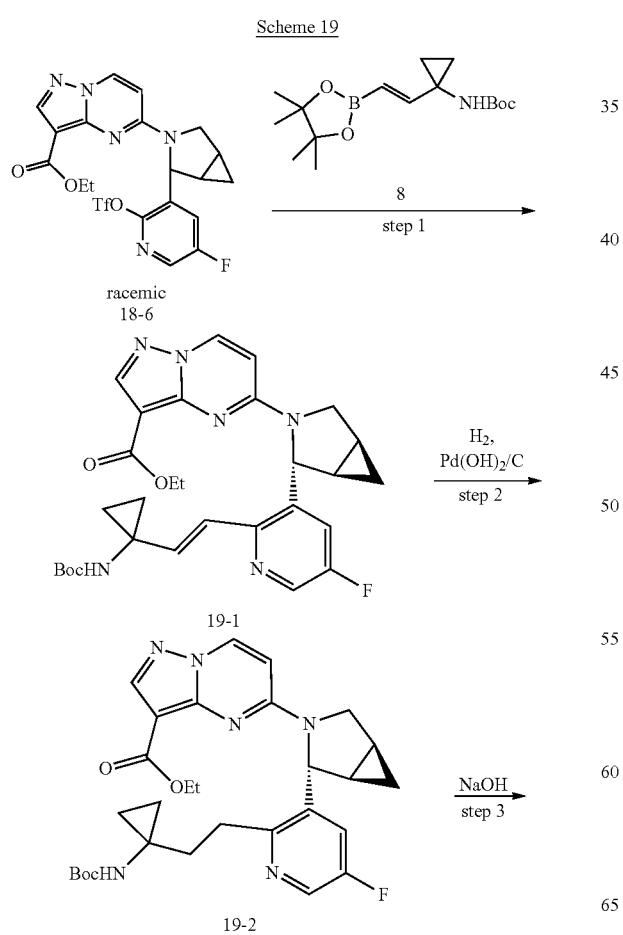

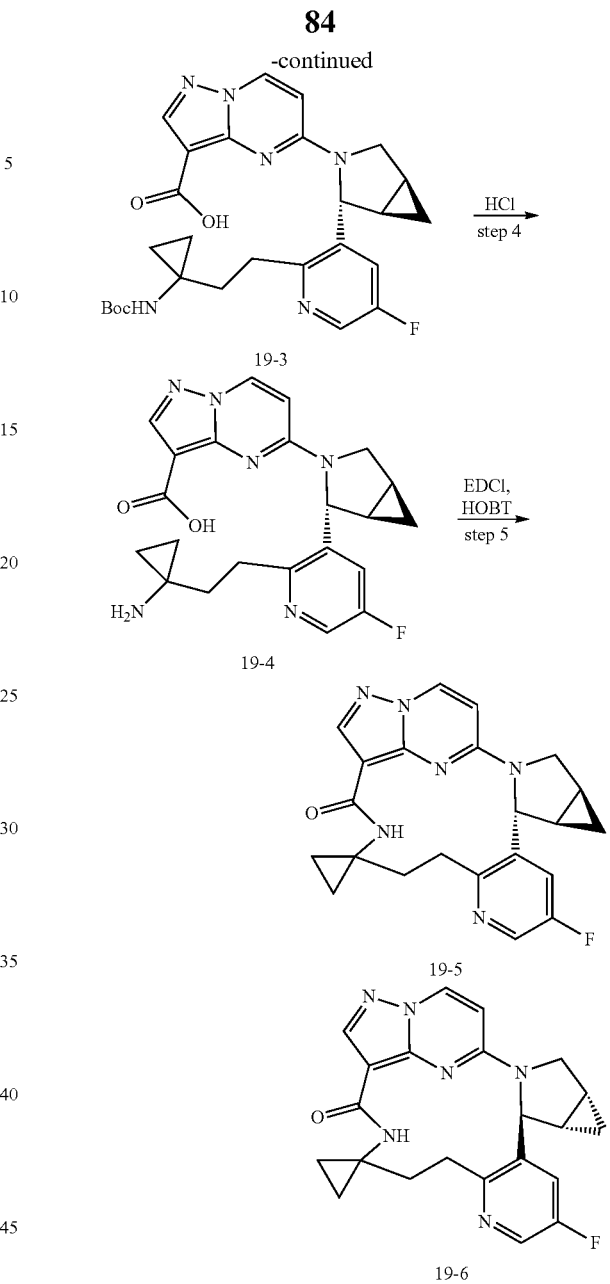

Step 1:

Compound 18-6 was converted to compound 19-1 following similar procedures described in Method 1, step 5, using boronic ester 8 instead. LC-MS: m/e=549 [M+H]+.

Step 2:

Compound 19-1 was converted to compound 19-2 following similar procedures described in Method 1, step 6. LC-MS: m/e=551 [M+H]+.

Step 3:

Compound 19-2 was converted to compound 19-3 following similar procedures described in Method 1, step 8. LC-MS: m/e=523 [M+H]+.

Step 4:

Compound 19-3 was converted to compound 19-4 following similar procedures described in Method 1, step 3. LC-MS: m/e=423 [M+H]+.

Step 5:

Compound 19-4 was converted to compounds 19-5 and 19-6 following similar procedures described in Method 1, step 9. LC-MS for compound 19-5: m/e=405 [M+H]+.
LC-MS for compound 19-5: m/e=405 [M+H]+.

Method 20:

Scheme 20

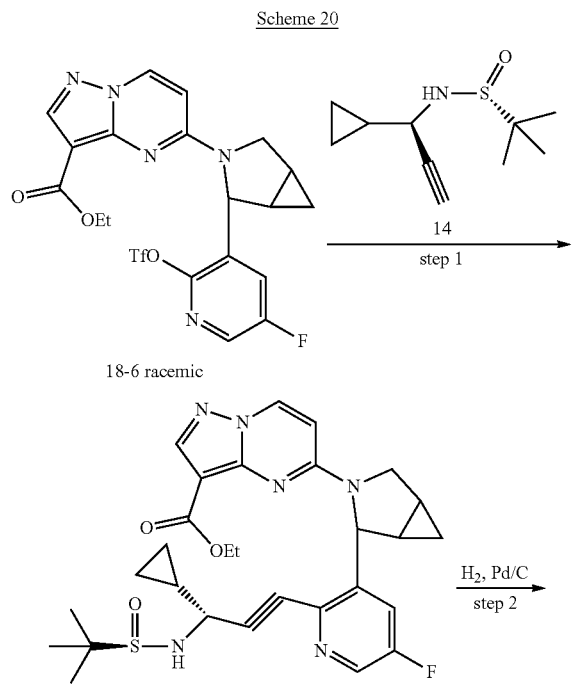

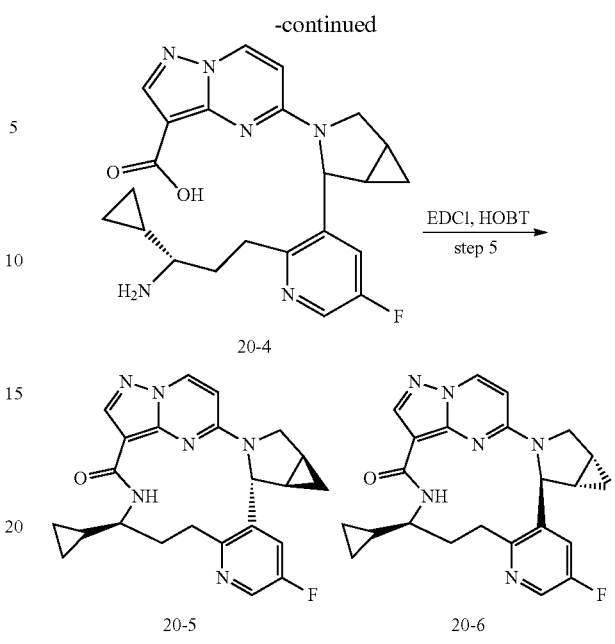

Step 1:

Compound 18-6 was converted to compound 20-1 following similar procedures described in Method 5, step 3, using intermediate 14 as the coupling reagent instead. LC-MS: m/e=565 [M+H]+.

Step 2:

Compound 20-1 was converted to compound 20-2 following similar procedures described in Method 7, step 2. LC-MS: m/e=569 [M+H]+.

Step 3:

Compound 20-2 was converted to compound 20-3 following similar procedures described in Method 1, step 8. LC-MS: m/e=541 [M+H]+.

Step 4:

Compound 20-3 was converted to compound 20-4 following similar procedures described in Method 1, step 3. LC-MS: m/e=437 [M+H]+.

Step 5:

Compound 20-4 was converted to compounds 20-5 and 20-6 following similar procedures described in Method 1, step 9. LC-MS for compound 20-5: m/e=419 [M+H]+.

Method 21:

Scheme 21

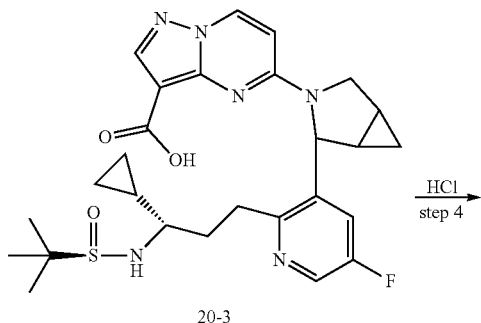

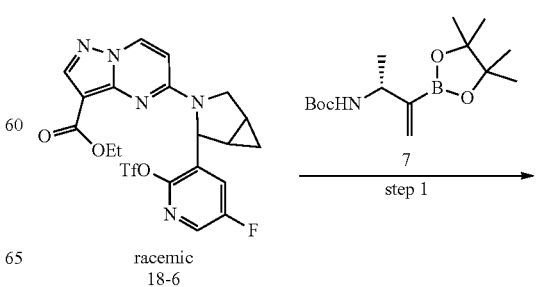

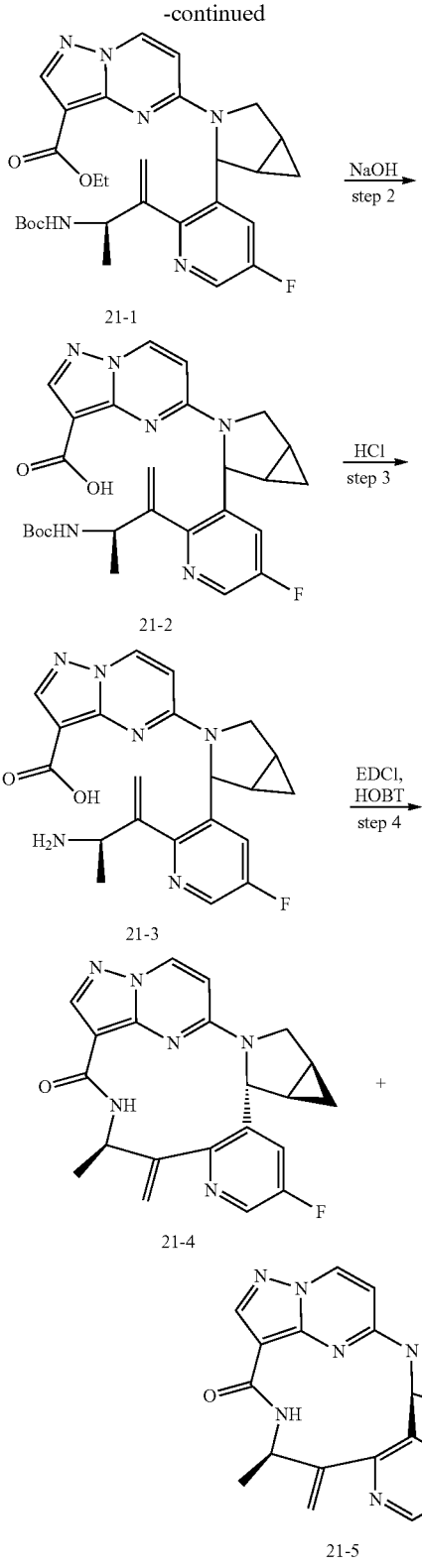

Step 2:

Compound 21-1 was converted to compound 21-2 following similar procedures described in Method 1, step 8. LC-MS: m/e=509 [M+H]$^+$.

Step 3:

Compound 21-2 was converted to compound 21-3 following similar procedures described in Method 2, step 3. LC-MS: m/e=409 [M+H]$^+$.

Step 4:

Compound 21-3 was converted to compound 21-4 and 21-5 following similar procedures described in Method 1, step 9. The two diastereoisomers were separated by Prep-HPLC [XBridge Shield RP18 OBD Column, 5 □m, 19*150 mm; mobile phase, Water (10 mM NH$_4$HCO$_3$+0.1% NH$_3$.H$_2$O) and Acetonitrile (27% Phase B up to 33% in 10 min); Detector, 254 nm UV]. LC-MS for compound 21-4: m/e=391 [M+H]$^+$. LC-MS for compound 21-5: m/e=391 [M+H]$^+$.

Method 22:

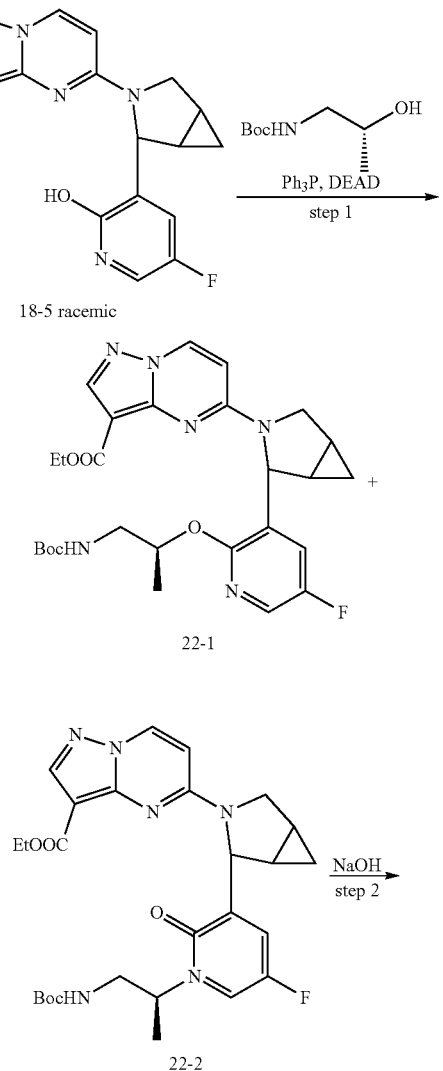

Step 1:

Compound 18-6 was converted to compound 21-1 following similar procedures described in Method 1, step 5, using the boronic ester 7 as the coupling reagent. LC-MS: m/e=537 [M+H]$^+$.

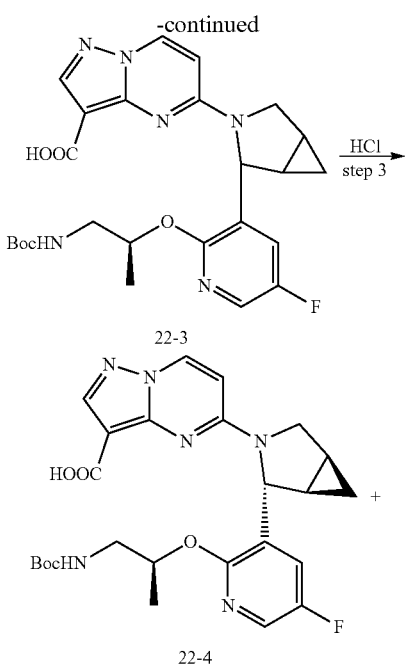

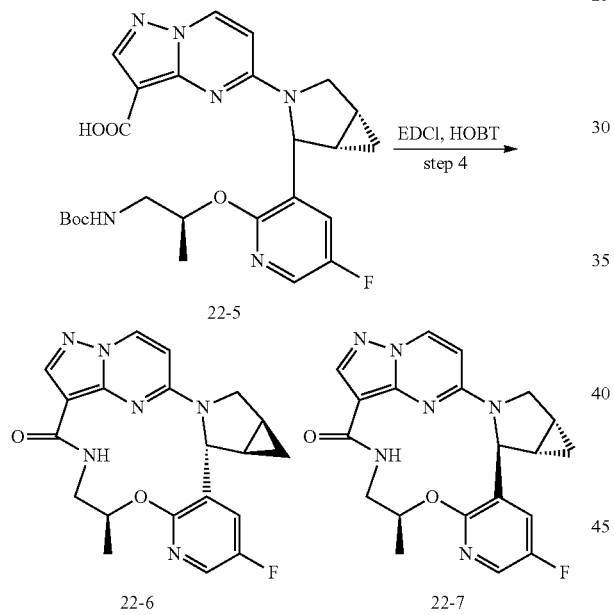

Step 1:

A mixture of 300 mg (0.78 mmol) of compound 18-5 and 206 mg (1.17 mmol) of tert-butyl N-[(2R)-2-hydroxypropyl] carbamate was dried from co-evaporation with DCM/toluene and then dissolved in 8 mL of DCM. To the above mixture was added 308 mg (1.17 mmol) of PPh$_3$ in portions at RT under Ar atmosphere. The mixture was stirred for 30 min at RT until the starting materials were completely dissolved, 204 mg (1.17 mmol) of DEAD was added dropwise. The mixture was stirred for 3 h and concentrated under reduced pressure. The residue was dissolved in DCM (10 mL), washed with brine (3×10 mL), and dried over anhydrous Na$_2$SO$_4$. It was filtered; the filtrate was concentrated to give a residue, which was purified by Prep-TLC eluting with 2% MeOH in DCM to afford compound 22-1 as major product and minor compound 22-2. LC-MS for compound 22-1: m/e=541 [M+H]$^+$. LC-MS for compound 22-2: m/e=541 [M+H]$^+$.

Step 2:

Compound 22-1 was converted to compound 22-3 following similar procedures described in Method 1, step 8. LC-MS: m/e=513 [M+H]$^+$.

Step 3:

Compound 22-3 was converted to compound 22-4 and 22-5 following similar procedures described in Method 2, step 3. The two diastereoisomers were separated by Prep-HPLC [XBridge Shield RP18 OBD Column, 5 µm, 19*150 mm; Mobile Phase A: Water (10 mM NH$_4$HCO$_3$+0.1% NH$_3$.H$_2$O), Mobile Phase B: ACN; Flow rate: 25 mL/min; Gradient: 15% B to 24% B in 11 min; 220 nm]. LC-MS for compound 22-4: m/e=413 [M+H]$^+$. LC-MS for compound 22-5: m/e=413 [M+H]$^+$.

Step 4:

Compound 22-4 was converted to compound 22-6 following similar procedures described in Method 1, step 9. LC-MS: m/e=395 [M+H]$^+$.

Similarly, Compound 22-5 was converted to compound 22-7 following similar procedures described in Method 1, step 9. LC-MS: m/e=395 [M+H]$^+$.

Method 23:

Scheme 23

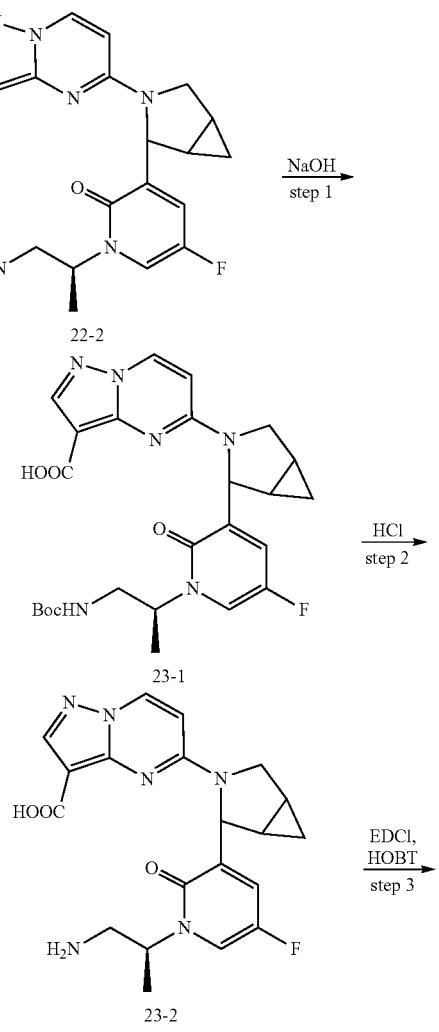

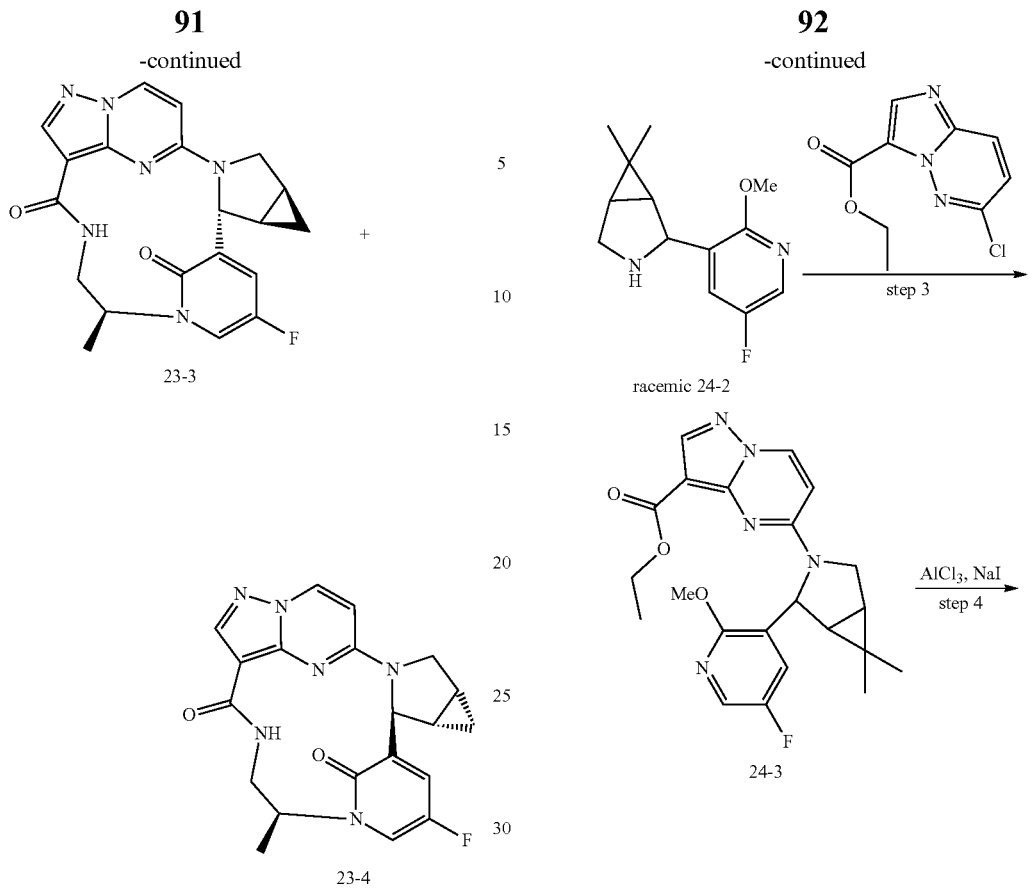

Step 1:

Compound 22-2 was converted to compound 23-1 following similar procedures described in Method 1, step 8. LC-MS: m/e=513 [M+H]$^+$.

Step 2:

Compound 23-1 was converted to compound 23-2 following similar procedures described in Method 2, step 3. LC-MS: m/e=413 [M+H Step 3:

Compound 23-2 was converted to compound 23-3 and 23-4 following similar procedures described in Method 1, step 9. The two diastereoisomers were separated by Prep-HPLC [Xselect CSH OBD 30*150 mm 5 μm; Mobile Phase A: Water (10 mM NH$_4$HCO$_3$), Mobile Phase B: ACN; Flow rate: 60 mL/min; Gradient: 12% B to 42% B in 9 min; 254/220 nm]. LC-MS for compound 23-3: m/e=395 [M+H]$^+$. LC-MS for compound 23-4: m/e=395 [M+H]$^+$.

Method 24:

Scheme 24

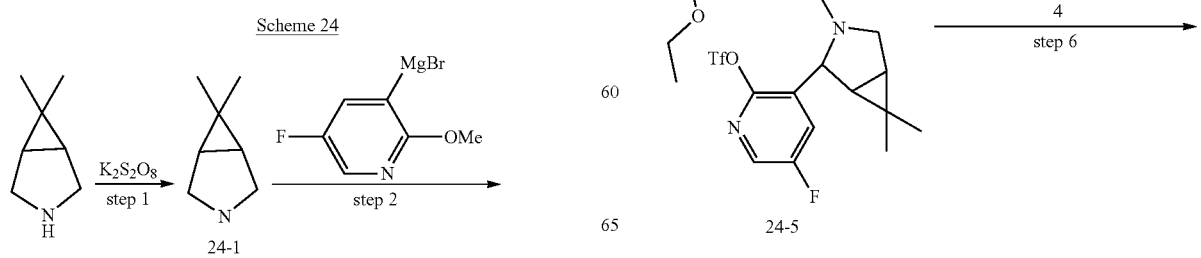

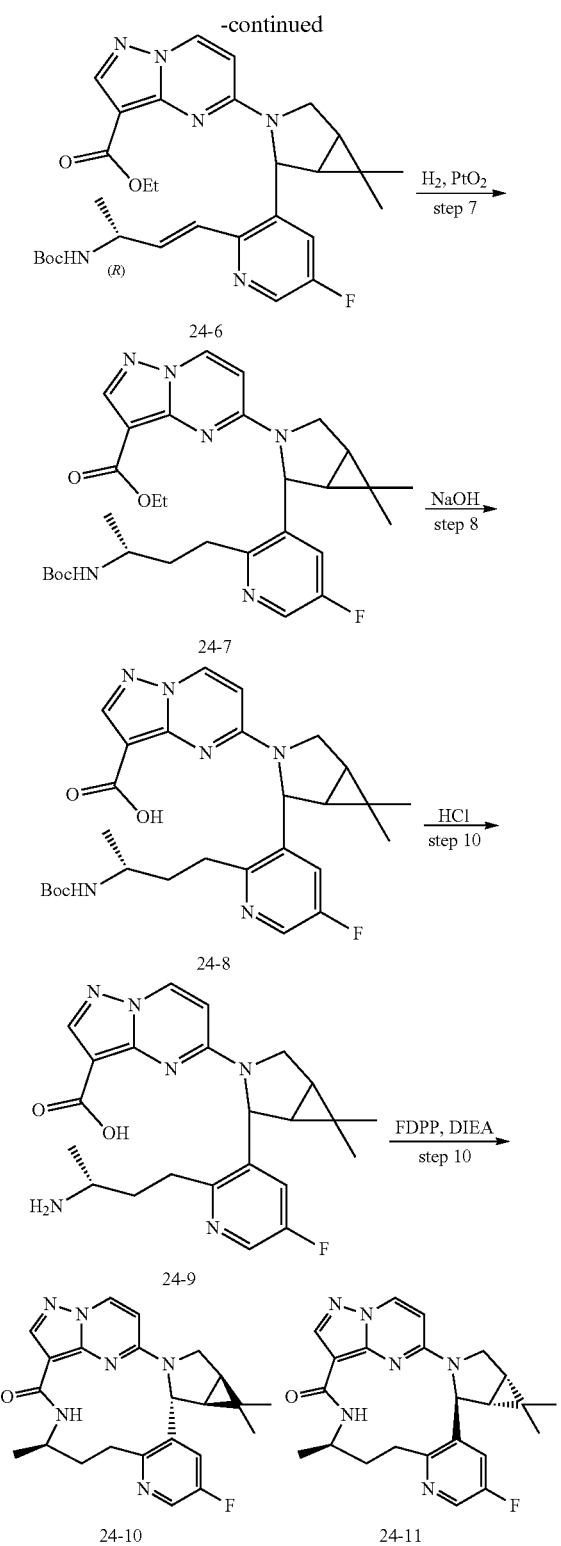

Step 1:

To a stirred solution of 827 mg (20.7 mmol) of NaOH and 2670 mg (9.9 mmol) of potassium peroxydisulfate in 2 mL of ACN and 15 mL of $H_2O$, was added 1000 mg (9.0 mmol) of 6,6-dimethyl-3-azabicyclo[3.1.0]hexane at −5° C. under argon atmosphere. The mixture was stirred at −3° C. for 4 h. To the above mixture was added 15.3 mg (0.09 mmol) of $AgNO_3$ in 0.5 mL water dropwise at −5° C. The mixture was stirred at 0° C. for an additional 2 h, and extracted with three 30 mL portions of TBME. The combined organic layers were washed with 50 mL of brine and dried over anhydrous $Na_2SO_4$. After filtration, the filtrate was concentrated under reduced pressure to obtain compound 24-1, which was used in next step without further purification. LC-MS: m/e=110 [M+H]$^+$.

Step 2:

To a stirred solution of 5.40 g (26.0 mmol) of 3-bromo-5-fluoro-2-methoxypyridine in 30 mL of THF was added 19.9 mL (26.0 mmol) of chloro(propan-2-yl)magnesium dropwise at 0° C. under nitrogen atmosphere. The mixture was stirred at 0° C. for 2 h and cooled to −78° C., a solution of 700 mg (6.40 mmol) of compound 24-1 in 10 mL of THF was added dropwise. The mixture was warm to RT and stirred for 2 h, and quenched with water at 0° C. It was adjusted to pH 6 with 1N HCl, extracted with two 20 mL portions of ethyl acetate. The aqueous layer was concentrated under reduced pressure to obtain compound 24-2 as HCl salt, which was used in next step without further purification. LC-MS: m/e=237 [M+H]$^+$.

Step 3:

Compound 24-2 was converted to compound 24-3 following similar procedures described in Method 7, step 4. LC-MS: m/e=426 [M+H]$^+$.

Step 4:

Compound 24-3 was converted to compound 24-4 following similar procedures described in Method 2, step 5. LC-MS: m/e=412 [M+H]$^+$.

Step 5:

Compound 24-4 was converted to compound 24-5 following similar procedures described in Method 6, step 5. LC-MS: m/e=544 [M+H]$^+$.

Step 6:

Compound 24-5 was converted to compound 24-6 following similar procedures described in Method 6, step 6. LC-MS: m/e=565 [M+H]$^+$.

Step 7:

Compound 24-6 was converted to compound 24-7 following similar procedures described in Method 6, step 7. LC-MS: m/e=567 [M+H]$^+$.

Step 8:

Compound 24-7 was converted to compound 24-8 following similar procedures described in Method 1, step 8. LC-MS: m/e=539 [M+H]$^+$.

Step 9:

Compound 24-8 was converted to compound 24-9 following similar procedures described in Method 1, step 3. LC-MS: m/e=439 [M+H]$^+$.

Step 10:

To a stirred solution of 15.0 mg (0.034 mmol) of compound 24-9 and 44.2 mg (0.34 mmol) of DIEA in 3.5 mL of DMF/DCM (2.5/1) was added 13.67 mg (0.036 mmol) of FDPP. The mixture was stirred at RT for 4 h under $N_2$ atmosphere and concentrated. It was diluted with 10 mL of $H_2O$ and extracted with three 20 mL portions of DCM. The combined organic layers were washed with 10 mL of brine and dried over anhydrous $Na_2SO_4$. After filtration, the filtrate was concentrated to give a residue, which was purified by Prep-TLC eluting with EtOAc to afford a residue, which was purified by Prep-HPLC [Xselect CSH OBD Column 30*150 mm 5 μm; mobile phase, Water (0.1% FA) and ACN (30% Phase B, up to 58% in 9 min); Flow rate: 60 mL/min. Detector, UV] to afford compound 24-10 and 24-11. LC-MS for compound 24-10: m/e=421 [M+H]$^+$. LC-MS compound 24-11: m/e=421 [M+H]$^+$.

Syntheses of Intermediates
1. Synthesis of Intermediate 2:

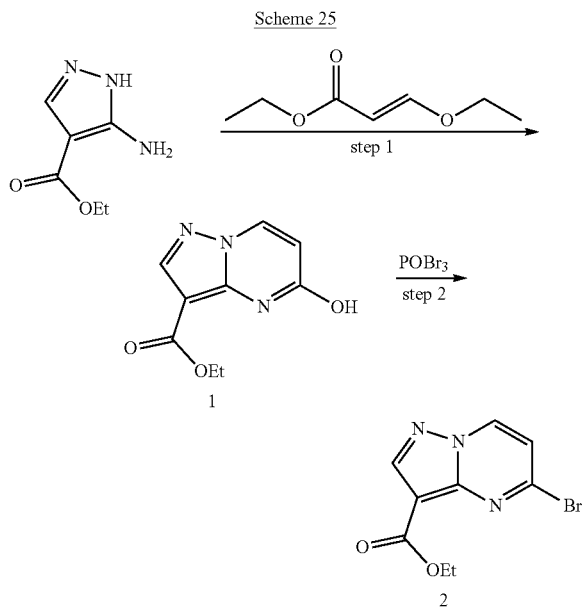

Step 1:
To a solution of 27.9 g (193 mmol) of ethyl (2E)-3-ethoxyprop-2-enoate in 250 mL of DMF were added 20.0 g (129 mmol) of ethyl 3-amino-1H-pyrazole-4-carboxylate and 63.0 g (193 mmol) of $Cs_2CO_3$. The mixture was stirred at 100° C. for 15 h under $N_2$ atmosphere, diluted with 1 L of water, and then extracted with three 500 mL portions of ethyl acetate. The organic phases were discarded; the aqueous phase was acidified to pH 3 with 1 N HCl and then extracted with four 500 mL portions of ethyl acetate. The combined organic extracts were washed with brine, dried over anhydrous $Na_2SO_4$. After filtration, the filtrate was concentrated to a volume about 500 mL, at which point, a lot of solids precipitated from the solution. After filtration, the solids were dried under vacuum to afford compound 1. LC-MS: m/e=208 [M+H]$^+$.

Step 2:
To a solution of 3.0 g (14.48 mmol) of compound 1 in 30 mL of MeCN was added 0.041 g (0.14 mmol) of $POBr_3$. The mixture was stirred at 60° C. for 2 h under $N_2$ atmosphere and quenched by addition of 100 mL of ice-water at 0° C. The resulting mixture was basified to pH 7 with aqueous saturated $NaHCO_3$, extracted with two 100 mL portions of ethyl acetate. The combined organic extracts were washed with brine, dried over anhydrous $Na_2SO_4$. After filtration, the filtrate was concentrated to afford a residue, which was purified by chromatography on silica gel column eluted with 20% of ethyl acetate in petroleum ether to afford compound 2. LC-MS: m/e=270 [M+H]$^+$.

3. Synthesis of Intermediates 3 and 4:

Scheme 26

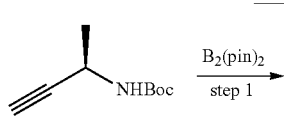

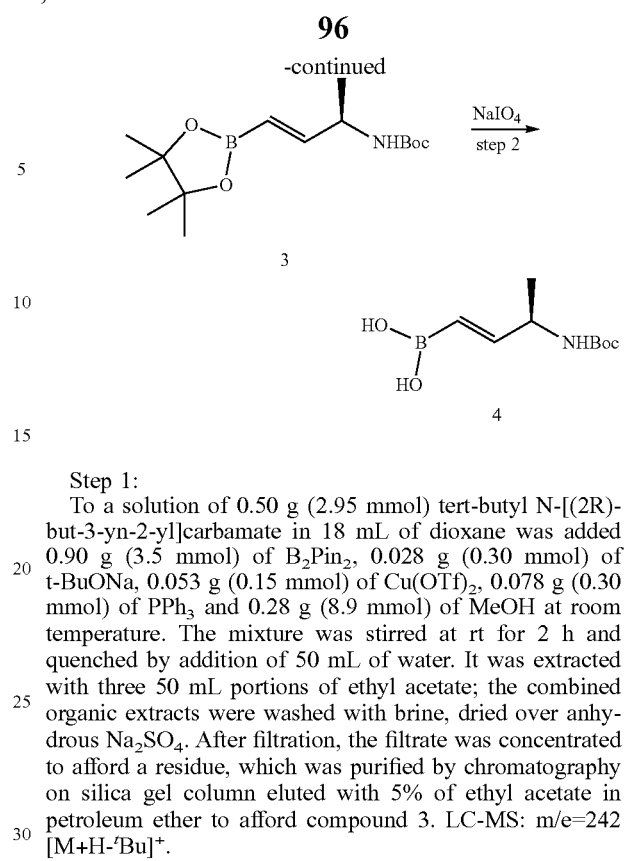

Step 1:
To a solution of 0.50 g (2.95 mmol) tert-butyl N-[(2R)-but-3-yn-2-yl]carbamate in 18 mL of dioxane was added 0.90 g (3.5 mmol) of $B_2Pin_2$, 0.028 g (0.30 mmol) of t-BuONa, 0.053 g (0.15 mmol) of $Cu(OTf)_2$, 0.078 g (0.30 mmol) of $PPh_3$ and 0.28 g (8.9 mmol) of MeOH at room temperature. The mixture was stirred at rt for 2 h and quenched by addition of 50 mL of water. It was extracted with three 50 mL portions of ethyl acetate; the combined organic extracts were washed with brine, dried over anhydrous $Na_2SO_4$. After filtration, the filtrate was concentrated to afford a residue, which was purified by chromatography on silica gel column eluted with 5% of ethyl acetate in petroleum ether to afford compound 3. LC-MS: m/e=242 [M+H-$^t$Bu]$^+$.

Step 2:
To a solution of 0.78 g (2.6 mmol) of compound 23-1 in 80 mL of acetone and 40 mL of water were added 1.74 g (8.14 mmol) of $NaIO_4$ and 0.61 g (7.9 mmol) of $NH_4OAc$. The mixture was stirred at rt overnight under $N_2$ atmosphere and quenched by addition of 200 mL of water. It was extracted with three 200 mL portions of ethyl acetate; the combined organic extracts were washed with brine, dried over anhydrous $Na_2SO_4$. After filtration, the filtrate was concentrated to afford a residue, which was purified by chromatography on silica gel column eluting with 50% of ethyl acetate in petroleum ether to afford compound 4. LC-MS: m/e=160 [M+H-$^t$Bu]$^+$.

3. Synthesis of Intermediate 6:

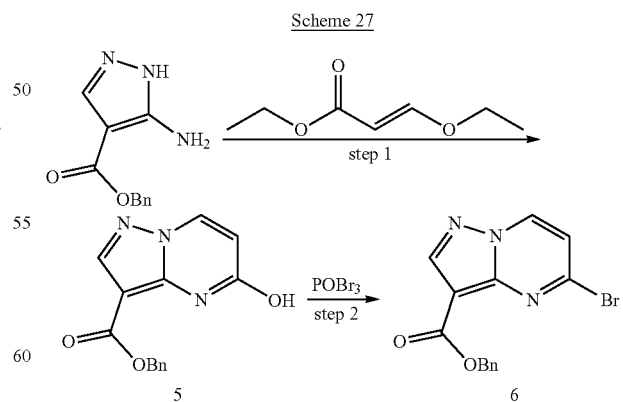

Step 1:
Compound 5 was prepared from benzyl 3-amino-1H-pyrazole-4-carboxylate following similar procedures described in Scheme 21, step 1. LC-MS: m/e=270 [M+H]$^+$.

Step 2:

Compound 5 was converted to compound 6 following similar procedures described in Scheme 21, step 2. LC-MS: m/e=332 [M+H]$^+$.

4. Synthesis of Intermediate 7:

Scheme 28

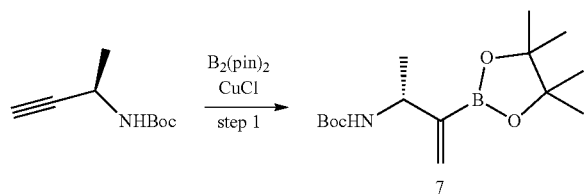

Step 1:

To a stirred mixture of 2.5 g (14.8 mmol) of tert-butyl N-[(2R)-but-3-yn-2-yl]carbamate in 60 mL of toluene were added 0.15 g (1.5 mmol) of CuCl, 4.13 g (0.016 mmol) of 4,4,5,5-tetramethyl-2-(4,4,5,5-tetramethyl-1,3,2-dioxaborolan-2-yl)-1,3,2-dioxaborolane and 0.21 g (2.1 mmol) of t-BuONa. To the above solution were added 5 mL (2 mmol, 10% in toluene) of P(t-Bu)$_3$ dropwise at −50° C. under argon atmosphere and 0.95 g (0.030 mmol) of methanol was added. The mixture was stirred at −50° C. for 1 h and concentrated under vacuum to get a residue, which was purified by chromatography on silica gel column eluting with 0 to 30% gradient of ethyl acetate in petroleum ether to afford compound 7. LC-MS: m/e=298 [M+H]$^+$.

5. Synthesis of Intermediate 8:

Scheme 29

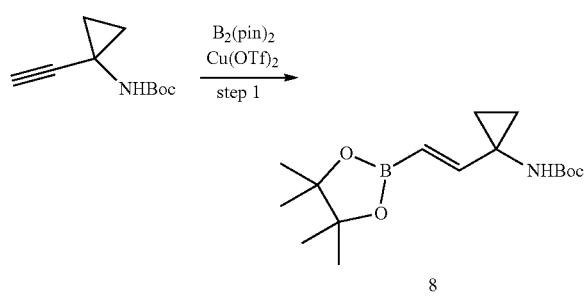

Step 1:

To a solution of 500 mg (2.78 mmol) of tert-butyl N-(1-ethynylcyclopropyl)carbamate in 10 mL of dioxane was added 841 mg (3.30 mmol) of 4,4,5,5-tetramethyl-2-(4,4,5,5-tetramethyl-1,3,2-dioxaborolan-2-yl)-1,3,2-dioxaborolane, 49.9 mg (0.140 mmol) of Cu(OTf)$_2$, 72.4 mg (0.280 mmol) of PPh$_3$, 26.5 mg (0.280 mmol) of sodium 2-methylpropan-2-olate and 265 mg (8.30 mmol) of MeOH. The mixture was stirred at rt for 2 h under nitrogen atmosphere and quenched by addition of 50 mL of water. It was extracted with three 15 mL portions of ethyl acetate; the combined organic extracts were washed with 30 mL of brine, dried over Na$_2$SO$_4$. After filtration, the filtrate was concentrated to afford a residue, which was purified by chromatography on silica gel column eluting with 0 to 5% gradient of ethyl acetate in petroleum ether to afford compound 8. LC-MS: m/e=295 [M−Me+H]$^+$.

6. Synthesis of Intermediate 10:

Scheme 30

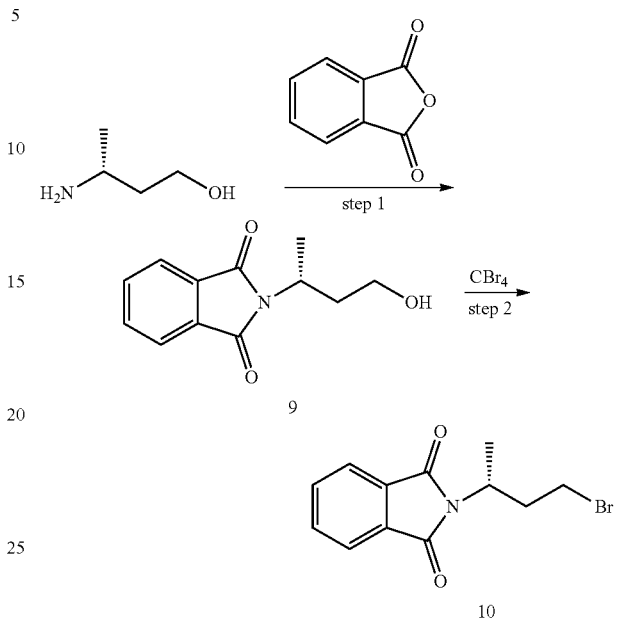

Step 1:

To a stirred solution of 1.6 g (18 mmol) (R)-3-aminobutan-1-ol in 30 mL of xylene was added 2.8 g (19 mmol) of 1,3-dihydro-2-benzofuran-1,3-dione at rt. The mixture was stirred at 140° C. overnight and cooled to rt. It was diluted with 100 mL of ethyl acetate, washed with 50 mL of saturated NaHCO$_3$ solution and 50 mL of 10% citric acid solution. The organic phase was dried over anhydrous Na$_2$SO$_4$. After filtration, the filtrate was concentrated under reduced pressure to afford crude compound 9, which was used in the next step directly without further purification. LC-MS: m/e=220 [M+H]$^+$.

Step 2:

To a stirred solution of 1.0 g (4.6 mmol) of compound 9 in 30 mL of CH$_2$Cl$_2$ was added 1.8 g (5.5 mmol) of CBr$_4$ in portions at 0° C. To the above mixture was added 1.3 g (5.0 mmol) of PPh$_3$ in portions at 0° C. The mixture was stirred at rt for 1 h and then concentrated under vacuum to afford a residue, which was purified by chromatography on silica gel column eluting with 15% of ethyl acetate in petroleum ether to afford compound 10. LC-MS: m/e=282, 284 [M+H]$^+$.

7. Synthesis of Intermediate 12:

Scheme 31

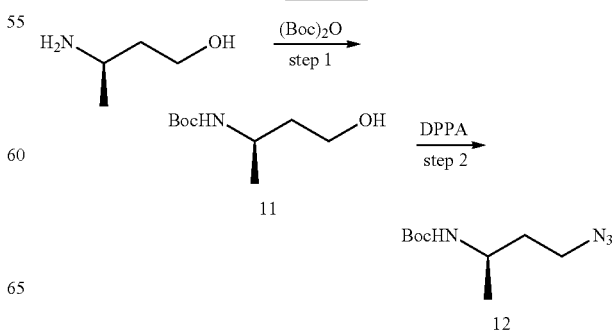

Step 1:

To a stirred solution of 0.50 g (5.6 mmol) (3R)-3-aminobutan-1-ol and 0.85 g (8.4 mmol) of Et$_3$N in 10 mL of CH$_2$Cl$_2$ was added 1.35 g (6.2 mmol) of Boc$_2$O in portions at 0° C. The mixture was stirred at rt for 1 h, diluted with 20 mL of water. It was extracted with three 20 mL portions of CH$_2$Cl$_2$. The combined organic layers were washed with 20 mL of brine, dried over anhydrous Na$_2$SO$_4$. After filtration, the filtrate was concentrated under reduced pressure to afford a residue, which was purified by silica gel column chromatography eluting with 50% ethyl acetate in petroleum ether to afford compound 11. $^1$H NMR: 1H NMR (300 MHz, DMSO-d$_6$) δ 6.62 (d, J=8.4 Hz, 1H), 4.34 (t, J=5.1 Hz, 1H), 3.55 (p, J=7.0 Hz, 1H), 3.40 (ddt, J=10.1, 6.8, 3.4 Hz, 2H), 1.63-1.40 (m, 2H), 1.39 (s, 9H), 1.02 (d, J=6.6 Hz, 3H).

Step 2:

To a stirred solution of 0.70 g (3.7 mmol) compound 11 and 1.3 g (4.8 mmol) of DPPA in 20 mL of toluene was added 0.73 g (4.1 mmol) of DBU dropwise under nitrogen atmosphere. The resulting mixture was stirred at rt for 1 h and then at 80° C. for additional 2 h. It was diluted with 100 mL of water, extracted with three 100 mL portions of CH$_2$Cl$_2$. The combined organic layers were washed with 100 mL of brine, dried over anhydrous Na$_2$SO$_4$. After filtration, the filtrate was concentrated under reduced pressure to afford residue, which was purified by silica gel column chromatography eluting with 5% ethyl acetate in petroleum ether to afford compound 12. $^1$H NMR (300 MHz, DMSO-d$_6$) δ 7.67-7.15 (m, 1H), 6.75 (d, J=8.4 Hz, 1 H), 3.60-3.49 (m, 1H), 3.32 (dd, J=14.2, 1.7 Hz, 1H), 1.60 (qd, J=7.1, 3.5 Hz, 2H), 1.39 (s, 9H), 1.04 (d, J=6.6 Hz, 3H).

8. Synthesis of Intermediate 14:

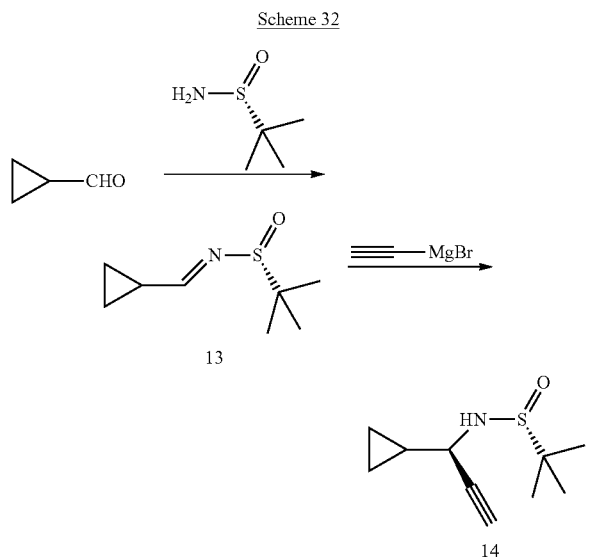

Scheme 32

Step 1:

To a stirred solution of 2.00 g (28.5 mmol) of cyclopropanecarbaldehyde in 120 mL of THF was added 3.80 g (31.4 mmol) of (R)-2-methylpropane-2-sulfinamide and 13.0 g (57.1 mmol) of Ti(OEt)$_4$. The mixture was stirred at 75° C. for 2 h and cooled to rt. It was diluted with 100 mL of ethyl acetate and 100 mL of water, then filtered; the filter cake was washed with 50 mL of ethyl acetate. The filtrate was extracted with three 60 mL portions of ethyl acetate. The combined organic extracts were washed with 100 mL of brine, dried over anhydrous Na$_2$SO$_4$. After filtration, the filtrate was concentrated under reduced pressure to afford a residue, which was purified by chromatography on silica gel column eluting with 20% of ethyl acetate in petroleum ether to afford compound 13. LC-MS: m/e=174 [M+H]$^+$.

Step 2:

To a stirred solution of 200 mg (1.15 mmol) of compound 13 in 3 mL of CH$_2$Cl$_2$ was added 7 mL (0.35 mmol, 0.5 M in THF) of bromo(ethynyl)magnesium dropwise at 0° C. under nitrogen atmosphere. The mixture was stirred at room temperature overnight under nitrogen atmosphere and quenched by addition of 10 mL of saturated NH$_4$Cl solution at 0° C. It was extracted with three 10 mL portions of CH$_2$Cl$_2$. The combined organic extracts were washed with 10 mL of brine, dried over anhydrous Na$_2$SO$_4$. After filtration, the filtrate was concentrated under reduced pressure to afford a residue, which was purified by chromatography on silica gel column eluted with 25% of ethyl acetate in petroleum ether to afford compound 14. LC-MS: m/e=200 [M+H]$^+$.

LC-MS Conditions Used in the Experimental Procedures Described Above:

Condition A: Shimadzu LC20AD/LCMS2020; Column: Shim-pack XR-ODS (50*3.0 mm) 2.2 μm; Mobile phase: A: 0.05% Trifluoroacetic acid in Water, B: 0.05% Trifluoroacetic acid in Acetonitrile; Gradient: 95:5 to 0:100 (A:B) over 1.1 min, 0:100 (A:B) for 0.55 min, Flow Rate: 1.2 ml/min; UV detection: 190-400 nm.

Condition B: Shimadzu LC30AD/LCMS2020, Column: CORTECS-C18 (50*2.1 mm) 2.7 μm; Mobile phase: A: 0.1% Formic acid in Water, B: 0.1% Formic acid in Acetonitrile; Gradient: 90:10 to 0:100 (A:B) over 1.1 min, 0:100 (A:B) for 0.50 min, Flow Rate: 1.0 ml/min. UV detection: 190-400 nm.

Condition C: Shimadzu LC3OAD/LCMS2020, Column: Ascentis Express (50*3.0 mm) 2.7 μm; Mobile phase: A: 0.05% Trifluoroacetic acid in Water, B: 0.05% Trifluoroacetic acid in Acetonitrile; Gradient: 95:5 to 0:100 (A:B) over 1.2 min, 0:100 (A:B) for 0.50 min, Flow Rate: 1.5 ml/min. UV detection: 190-400 nm.

Condition D: Shimadzu LC20ADXR/LCMS2020, Column: Poroshell HPH-C18 (50*3.0 mm) 2.7 μm; Mobile phase: A: 5 mM Ammonium Bicarbonate in Water, B: Acetonitrile; Gradient: 90:10 to 5:95 (A:B) over 1.2 min, 5:95 (A:B) for 0.50 min, Flow Rate: 1.2 mL/min. UV detection: 190-400 nm.

Condition E: Shimadzu LC20ADXR/LCMS2020, Column: Kinextex EVO C18 (50*3.0 mm) 2.6 μm; Mobile phase: A: 5 mM Ammonium Bicarbonate in Water, B: Acetonitrile; Gradient: 90:10 to 5:95 (A:B) over 1.2 min, 5:95 (A:B) for 0.50 min, Flow Rate: 1.2 ml/min. UV detection: 190-400 nm.

Condition F: Shimadzu LC20ADXR/LCMS2020, Column: Kinextex XB-C18 (50*3.0 mm) 2.6 μm; Mobile phase: A: 0.1% Formic acid in Water, B: 0.1% Formic acid in Acetonitrile; Gradient: 90:10 to 0:100 (A:B) over 1.1 min, 0:100 (A:B) for 0.50 min, Flow Rate: 1.5 ml/min. UV detection: 190-400 nm.

ASSAYS

Protocols that may be used to determine the recited potency for the compounds of the disclosure are described below.

The HotSpot assay platform was used to measure kinase/inhibitor interactions as described in Anastassiadis et al., Nat Biotechnol. 29:1039-45, 2011. In brief, for each reaction, kinase and substrate were mixed in a buffer containing 20 mM HEPES (pH 7.5), 10 mM MgCl$_2$, 1 mM EGTA, 0.02% Brij35, 0.02 mg/mL BSA, 0.1 mM Na$_3$VO$_4$, 2 mM DTT, and 1% DMSO. Compounds were then added to each reaction mixture. After a 20-min incubation, ATP (Sigma-Aldrich) and [γ-33P] ATP (PerkinElmer) were added at a final total concentration of 100 μM. Reactions were carried out at room temperature for 2 h and spotted onto P81 ion exchange cellulose chromatography paper (Whatman). Filter paper was washed in 0.75% phosphoric acid to remove unincorporated ATP. The percent remaining kinase activity relative to a vehicle-containing (DMSO) kinase reaction was calculated for each kinase/inhibitor pair. Outliers were identified and removed as described in Anastassiadis et al., Nat Biotechnol. 29:1039-45, 2011. IC$_{50}$ values were calculated using Prism 5 (GraphPad). The testing results for selected compounds are summarized in Table 2, wherein A represents the IC$_{50}$ value of <100 nM; B represents the IC$_{50}$ value of 100-1000 nM; and C represents the IC$_{50}$ value of >1000 nM.

TABLE 2

TRK Inhibitory Activity of Representative Examples

| Compound | TRK A IC$_{50}$ nM |
|---|---|
| LOXO-101* | A (5.9 nM) |
| 1-8 | A |
| 1-17 | A |
| 3-3 | C |
| 4-3 | A |
| 5-6 | B |
| 6-10 | A |
| 7-11 | A |
| 7-12 | C |
| 8-8 | B |
| 9-7 | A |
| 10-5 | A |
| 10-6 | B |
| 11-4 | A |
| 11-5 | C |
| 11-6 | A |
| 12-12 | C |
| 13-11 | A |
| 13-12 | B |
| 14-6 | C |
| 14-7 | C |
| 15-10 | C |
| 16-10 | C |
| 16-11 | C |
| 17-12 | C |
| 17-13 | C |
| 18-11 | A |
| 18-12 | C |
| 19-5 | A |
| 19-6 | C |
| 20-5 | A |
| 20-6 | C |
| 21-4 | A |
| 21-5 | B |
| 22-6 | A |
| 22-7 | C |
| 23-3 | A |
| 23-4 | C |
| 24-10 | A |
| 24-11 | C |

*A reference compound for comparison: CAS No. [1223405-08-0].

Unless otherwise indicated, all numbers expressing quantities of ingredients, properties such as molecular weight, reaction conditions, and etc. used in herein are to be understood as being modified in all instances by the term "about." Each numerical parameter should at least be construed in light of the number of reported significant digits and by applying ordinary rounding techniques. Accordingly, unless indicated to the contrary, the numerical parameters may be modified according to the desired properties sought to be achieved, and should, therefore, be considered as part of the disclosure. At the very least, the examples shown herein are for illustration only, not as an attempt to limit the scope of the disclosure.

The terms "a," "an," "the" and similar referents used in the context of describing embodiments of the present disclosure (especially in the context of the following claims) are to be construed to cover both the singular and the plural, unless otherwise indicated herein or clearly contradicted by context. All methods described herein may be performed in any suitable order unless otherwise indicated herein or otherwise clearly contradicted by context. The use of any and all examples, or exemplary language (e.g., "such as") provided herein is intended merely to better illustrate embodiments of the present disclosure and does not pose a limitation on the scope of any claim. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments are described herein, including the best mode known to the inventors for carrying out the embodiments. Of course, variations on these described embodiments will become apparent to those of ordinary skill in the art upon reading the foregoing description. The inventor expects skilled artisans to employ such variations as appropriate, and the inventors intend for the embodiments of the present disclosure to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A compound represented by a formula:

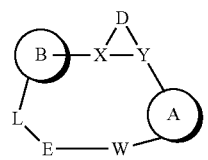

or a pharmaceutically acceptable salt thereof; wherein

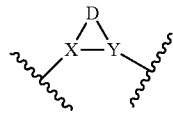

is

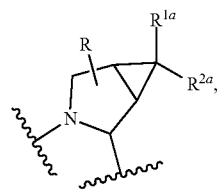

wherein the ring N atom is attached to Ring B:

- Ⓐ (Ring A) is an optionally substituted pyridin-di-yl, which is substituted with 0, 1, 2, or 3 substituents and each substituent is independently $R^A$, F, Cl, Br, I, CN, —$OR^A$, $CF_3$, —$NO_2$, —$NR^AR^B$, —$COR^A$, —$CO_2R^A$, —$OCOR^A$, —$OCONR^AR^B$, —$NR^ACOR^B$, or —$CONR^AR^B$;

- Ⓑ (Ring B) is an optionally substituted pyrazolo[1,5-a]pyrimidin-3,5-di-yl, which is substituted with 0, 1, 2, or 3 substituents and each substituent is independently $R^A$, F, Cl, Br, I, CN, —$OR^A$, $CF_3$, —$NO_2$, —$NR^AR^B$, —$COR^A$, —$CO_2^A$, —$OCOR^A$, —$OCONR^AR^B$, —$NR^ACOR^B$, or —$CONR^AR^B$;

L is —$C(O)NR^A$, wherein the carbon atom is attached to Ring B;

E is $C_{1-3}$ alkylene having, as chemically appropriate, 0, 1, 2, 3, 4, 5, or 6 substituents, wherein the substituents of E are independently F, Cl, Br, I, OH, =O, $C_{1-6}$ alkyl or $C_{1-6}$ cycloalkyl, wherein two of the substituents of E may connect together with the attached carbon atom of E to form a 3-membered saturated ring;

W is a covalent bond, O, $NR^A$, $CR^{A1}R^{B1}$, $CR^{A1}$=$CR^{B1}$, or C=$CR^{A1}R^{B1}$;

$R^{A1}$ and $R^{B1}$ are independently H, F, Cl, Br, I, or $C_{1-6}$ hydrocarbyl;

$R^A$ and $R^B$ are independently H or $C_{1-6}$ hydrocarbyl;

$R^{1a}$ and $R^{2a}$ are independently H, OH, $C_{1-3}$alkyl, F, Cl, or Br; and R represents 0, 1, 2, 3, 4, or 5 substituents at any ring carbon atom of the pyrrolidine ring and each R is independently H, OH, $C_{1-3}$alkyl, F, Cl, or Br.

2. The compound of claim 1, wherein Ring A is optionally substituted pyridin-2,3-di-yl.

3. The compound of claim 1, wherein Ring A is optionally substituted 5-fluoro-pyridin-2,3-di-yl.

4. The compound of claim 1, wherein

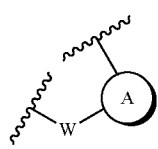

is optionally substituted (pyridin-3-yl)2-oxy-yl.

5. The compound of claim 1, wherein the compound is further represented by a formula:

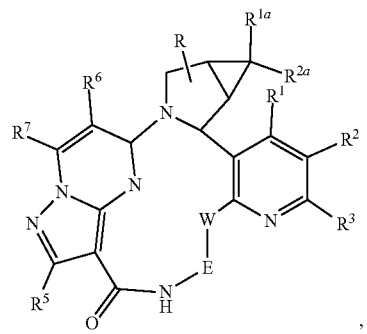

or a pharmaceutically acceptable salt thereof, wherein $R^1$, $R^2$, $R^3$, $R^5$, $R^6$, and $R^7$ are independently $R^A$, F, Cl, Br, I, CN, —$OR^A$, $CF_3$, —$NO_2$, —$NR^AR^B$, —$COR^A$, —$CO_2R^A$, —$OCOR^A$, —$OCONR^AR^B$, —$NR^ACOR^B$, or —$CONR^AR^B$.

6. The compound of claim 5, wherein R, $R^{1a}$, or $R^{2a}$ is independently H or $CH_3$.

7. The compound of claim 1, wherein W is $CH_2$.

8. The compound of claim 1, wherein W is O.

9. The compound of claim 1, wherein W is C=$CH_2$.

10. The compound of claim 1, wherein E is:

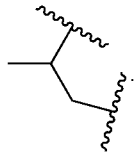 [SMILES: *CC(*)C]

11. The compound of claim 1, wherein E is:

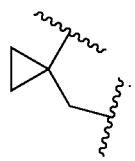 [SMILES: *CC1(*)CC1]

12. The compound of claim 1, wherein E is:

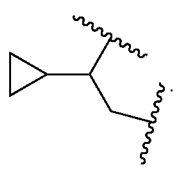

13. The compound of claim 1, wherein E is:

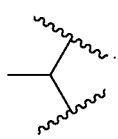

14. The compound of claim 1, wherein E-W is:

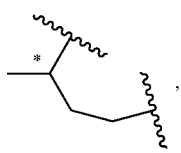 [SMILES: *CCC(*)C]

wherein the asterisk indicates the point of attachment of C atom to L.

15. The compound of claim 1, wherein E-W is:

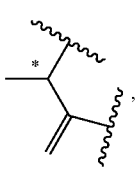 [SMILES: *C(=C)C(*)C]

wherein the asterisk indicates the point of attachment of C atom to L.

16. The compound of claim 1, wherein E-W is:

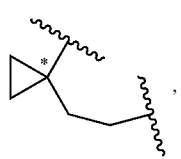 [SMILES: *CCC1(*)CC1]

wherein the asterisk indicates the point of attachment of C atom to L.

17. The compound of claim 1, wherein E-W is:

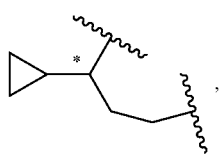 [SMILES: *CCC(*)C1CC1]

wherein the asterisk indicates the point of attachment of C atom to L.

18. The compound of claim 1, wherein E-W is:

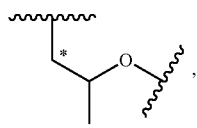 [SMILES: *CC(C)O*]

wherein the asterisk indicates the point of attachment of C atom to L.

19. The compound of claim 1, or a pharmaceutically acceptable salt thereof, wherein the compound is an optionally substituted ($1^3E,1^4E,2^1R,2^2R,2^5S$)-4-methylene-$2^3$,6-diaza-1(5,3)-pyrazolo[1,5-a]pyrimidina-3(3,2)-pyridina-2(3,2)-bicyclo[3.1.0]hexanacycloheptaphan-7-one, optionally substituted, ($1^3E,1^4E,2^1R,2^4S,2^5S$)-4-methylene-$2^3$,6-diaza-1(5,3)-pyrazolo[1,5-a]pyrimidina-3(3,2)-pyridina-2(3,4)-bicyclo[3.1.0]hexanacycloheptaphan-7-one, optionally substituted, ($1^3E,1^4E,2^1R,2^2R,2^5S$)-4-oxa-$2^3$,7-diaza-1(5,3)-pyrazolo[1,5-a]pyrimidina-3(3,2)-pyridina-2(3,2)-bicyclo[3.1.0]hexanacycloheptaphan-8-one, optionally substituted ($1^3E,1^4E,2^1R,2^4S,2^5S$)-4-oxa-$2^3$,7-diaza-1(5,3)-pyrazolo[1,5-a]pyrimidina-3(3,2)-pyridina-2(3,4)-bicyclo[3.1.0]hexanacyclooctaphan-8-one, optionally substituted, ($1^3E,1^4E,2^1R,2^2R,2^5S$)-$2^3$,7-diaza-1(5,3)-pyrazolo[1,5-a]pyrimidina-3(3,2)-pyridina-2(3,2)-bicyclo[3.1.0]hexanacycloheptaphan-8-one, or optionally substituted, ($1^3E,1^4E,2^1S,2^4S,2^5R$)-$2^6$,$2^6$-dimethyl-$2^3$,7-diaza-1(5,3)-pyrazolo[1,5-a]pyrimidina-3(3,2)-pyridina-2(3,4)-bicyclo[3.1.0]hexanacyclooctaphan-8-one.

20. The compound of claim 1, or a pharmaceutically acceptable salt thereof, wherein the compound is:

17-12

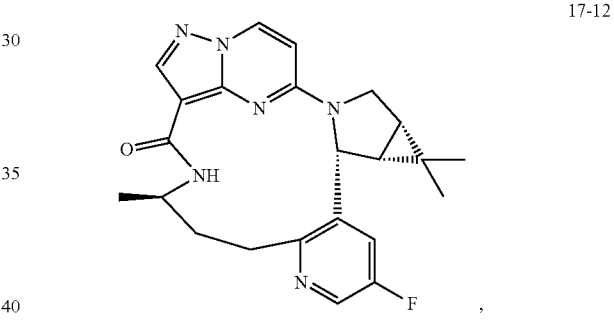

17-13

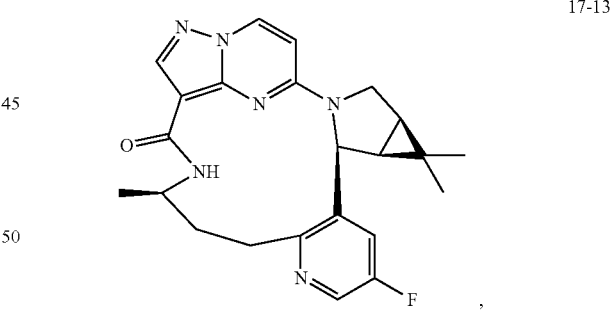

18-11

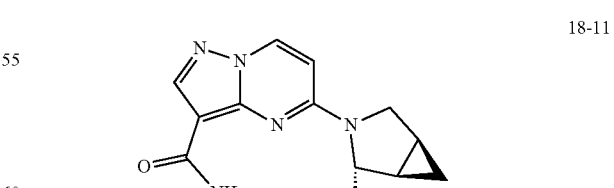

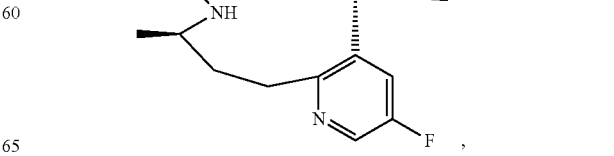

18-12
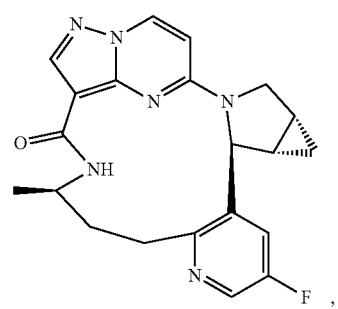,
19-5
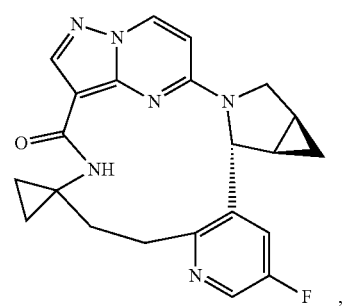,
19-6
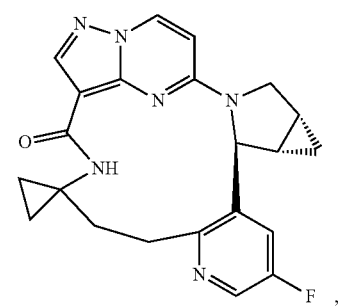,
20-5
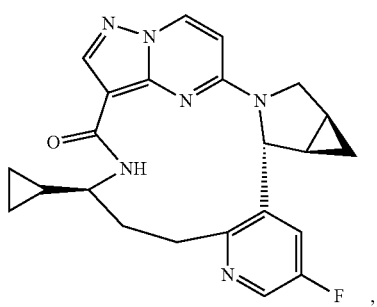,
20-6
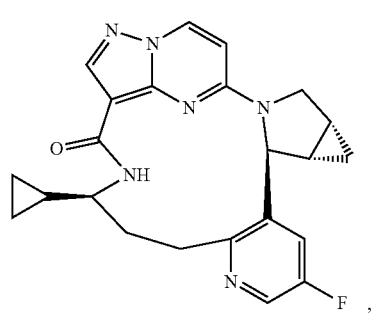,
21-4
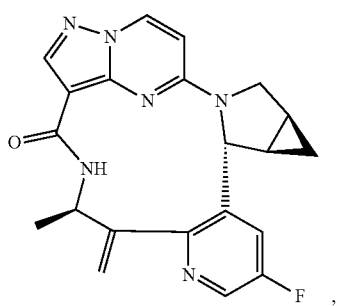,
21-5
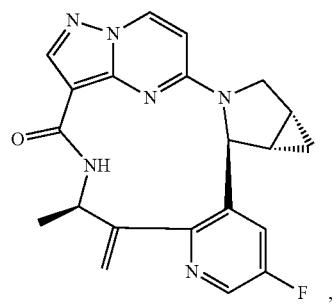,
22-6
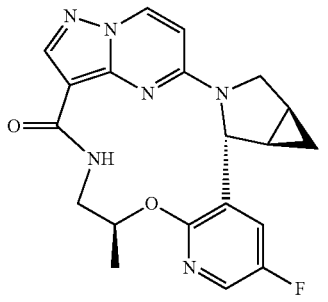,
22-7
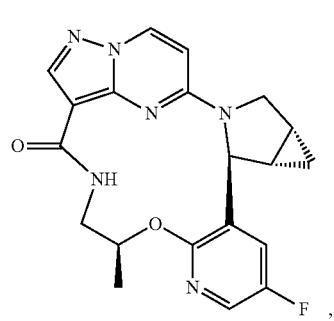,
24-10
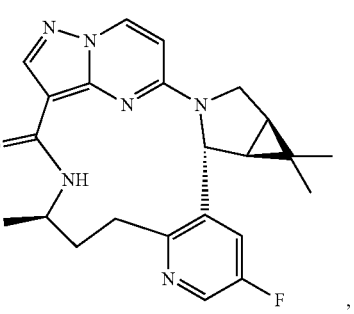, or

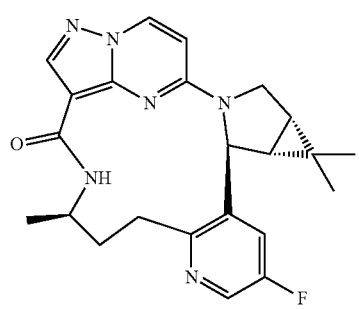
24-11
21. A pharmaceutical composition comprising a compound of claim 1 or a pharmaceutically acceptable salt thereof, and at least one pharmaceutically acceptable carrier.
* * * * *